United States Patent [19]
Besmer et al.

[11] Patent Number: 6,159,461
[45] Date of Patent: *Dec. 12, 2000

[54] USE OF C-KIT LIGAND WITH TNF-α AND HEMATOPOIETIC FACTORS FOR THE EXPANSION OR DIFFERENTIATION OF HEMATOPOIETIC CELLS

[75] Inventors: Peter Besmer; Jochen Buck; Malcolm A. S. Moore, all of New York, N.Y.; Karl Nocka, Harvard, Mass.

[73] Assignee: Sloan-Kettering Institute for Cancer Research, New York, N.Y.

[ * ] Notice: This patent is subject to a terminal disclaimer.

[21] Appl. No.: 08/898,982

[22] Filed: Jul. 23, 1997

Related U.S. Application Data

[63] Continuation of application No. 08/325,240, filed as application No. PCT/US93/03640, Apr. 16, 1993, Pat. No. 6,001,803, which is a continuation-in-part of application No. 07/873,962, Apr. 23, 1992, abandoned.

[51] Int. Cl.[7] .......................... A61K 38/18; A61K 38/19; A61K 38/20
[52] U.S. Cl. .......................... 424/85.1; 424/85.2
[58] Field of Search .................... 514/85.1, 85.2

[56] References Cited

U.S. PATENT DOCUMENTS

| | | |
|---|---|---|
| 5,199,942 | 4/1993 | Gillis . |
| 5,399,493 | 3/1995 | Emerson et al. . |
| 5,409,825 | 4/1995 | Hoffman et al. . |
| 5,767,074 | 6/1998 | Besmer et al. .......................... 424/85.1 |
| 6,001,803 | 12/1999 | Besmer et al. .......................... 514/12 |

FOREIGN PATENT DOCUMENTS

| | | |
|---|---|---|
| 0423980 | 4/1990 | European Pat. Off. . |
| 9114757 | 10/1991 | WIPO . |
| 9200376 | 1/1992 | WIPO . |
| 9206220 | 4/1992 | WIPO . |

OTHER PUBLICATIONS

Anderson, D.M. Molecular Cloning of Mast Cell Growth Factor, a Hematopietin That Is Active In Both Membrane Bound And Soluble Forms. Cell (1990) 63:235–243 (Exhibit 8).

Bazan, J.F. Genetic And Structural Homology Of Stem Cell Factor and Macrophage Colony–Stimulating factor. Cell (1991) 65:9–10 (Exhibit 9).

Besmer, P. A New Acute Transforming Feline Retrovirus and Relationship of its Oncogene v–kit with the Protein Kinase Gene Family. Nature (1986) 320:415–421 (Exhibit 10).

Bischoff, S.C., and Dahinden, C.A. C–Kit Ligand: A Unique Potentiator Of Mediator Release by Human Lung Mast Cells. J. Exp. Med. (1992) 175:237–244 (Exhibit 11).

Chabot, B. The Proto–Oncogene C–Kit Encoding A Transmembrane Tyrosine Kinase Receptor Maps To The Mouse W Locus. Nature (1988) 335:88–89 (Exhibit 12).

Copeland, N.G. Mast Cell Growth Factor Maps near the steel Locus On Mouse Chromosome 10 and Is Deleted In A Number OfSteel Alleles. Cell (1990) 63:175–183 (Exhibit 13).

Flanagan, J.G. and Leder, P. The Kit–Ligand: A Cell Surface Molecule Altered In Steel Mutant Fibroblasts. Cell (1990) 63:185–194 (Exhibit 14).

Flanagen, J.G., et al. Transmembrane Form Of The Kit Ligand Growth Factor Is Determined By Alternative Splicing And Is Missing in the SId Mutant. Cell (1991) 64:1025–1035 (Exhibit 15).

Huang, E., et al. The Hematopoietic Growth Factor KL Is Encoded by SI Locus and is the Ligand of the C–Kit Receptor, the Gene Product of the W Locus. Cell (1990) 63:225–233 (Exhibit 17).

Karhumaki, E. An Improved Enrichment Method For Functionally Competent, Highly Purified Peripheral Blood Dendritic Cells And its Application To HIV–Infected Blood Samples. Clin. Exp. Immunol. (1993) (Exhibit 18).

Martin, F.H., et al. Primary Structure and Functional Expression of rat and human Stem Cell Factor DNAs. Cell (1990)63:203–211 (Exhibit 19).

Majumder, S., et al. C–Kit Protein, a Transmembrane Kinase: Identification In Tissues and Characterization. Molecular and Cellular Biology. (1988) 8:4896–4903 (Exhibit 20).

Metcalf, D. and Nicola, N.A., Direct Proliferative Actions Of STem Cell Factor On Murine Bone Marrow Cells In Vitro: effects of Combination With Colony–Stimulating Factors. Proc. Natl. Acad. Sci. USA 886239–6243 (Exhibit 21).

Moore, M.A.S., Clinical Implications of Positive and Negative Hematopoietic Stem Cell Regulators. The Journal of The American Society of Hematology (1991) 78:1–19 (Exhibit 22).

Moore, M.A.S., and Warren, D.J. Synergy of Interleukin 1 and Granulocyte Colony–Stimulating Factor: In Vivo stimulation of Stem Cell Recovery and Hematopoietic Regeneration Following 5–Fluorouracil Treatment of Mice. Proc. Natl. Acad. Sci. USA (1987) 84:7134–7138 (Exhibit 23).

Muench, M.O., et al. Interactions Among Colony–Stimulating Factors, IL–1b, IL–6, and Kit–Ligand In The Regulation Of Primitive,Murine Hematopoietic Cells. Exp. Hematol. (1992) 20:339–349 (Exhibit 24).

Nocka, K.H., et al. Candidate Ligand For C–Kit: Purification of a Fibroblast–Derived Mast Cell Growth Factor. Experimental Hematology (1990) 18:253 (Exhibit 25).

Nocka, K. et al. Expression of C–Kit Gene Products In Known Cellular Targets Of W Mutations In Normal And W Mutant Mice–Evidence For An Impaired C–Kit Kinase In Mutant Mice. Genes & Development (1989) 3:816–826 (Exhibit 26).

(List continued on next page.)

Primary Examiner—David L. Fitzgerald
Attorney, Agent, or Firm—John P. White; Cooper & Dunham LLP

[57] ABSTRACT

Compositions comprising c-kit ligand, TNF-α, and a hematopoietic factor are useful to promote the expansion of peripheral blood cells or the expansion and differentiation of hematopoietic progenitor cells.

19 Claims, 60 Drawing Sheets

OTHER PUBLICATIONS

Nocka, K, et al. Molecular Bases Of Dominant Negative and Loss Of Function Mutations At the Murine C–Kit/White Spotting Locus: W37, WV, W41, and W. The EMBO Journal (1990) 9:1805–1813 (Exhibit 27).

Nocka, K, et al. Candidate Ligand For The C–Kit Transmembrane Kinase Receptor: KL, A Fibroblast Derived Growth Factor Stimulates Mast Cells And Erythroid Progenitors. The EMBO Journal (1990) 9:3287–3294 (Exhibit 28).

Orr–Urtreger, A. et al. Development Expression of C–Kit, A Proto–Oncogene Encoded By The W Locus. Development (1990) 109:911–923 (Exhibit 29).

Qiu,F., et al. Primary Structure C–Kit: Relationship With The CSF–1/PDGF Receptor Kinase Family–Oncogene Activation Of V–Kit Involves Deletion Of Extracellular Domain and C Terminus. IRL Press Limited, Oxford, England. (Exhibit 30).

Reith, A.D., et al. W Mutant Mice With Mild Or Severe Developmental Defects Contain Distinct Point Mutations In The Kinase Domain Of The C–Kit Receptor. Genes & Development (1990) 4:390–400 (Exhibit 31).

Tan, J.C., et al. The Dominant W42 Spotting Phenotype Results From A Missense Mutation In The C–Kit Receptor Kinase. Science Reports (1990) 209–212. (Exhibit 32).

Taxi, A., et al. Evidence That Granulocyte Macrophage–Colony Stimulating Factor Regulates The Distribution And Differentiated State Of Dendritic Cells/Langerhans Cells In Human Lung And Lung Cancers. (1993) 91:566–576 (Exhibit 33).

Thomas, R., et al. Isolation and Characterization of Human Peripheral Blood Dendritic Cells. The Journal of Immunology (1993) 150:821–834 (Exhibit 34).

Williams, D.E., et al. Identification of a Ligand for the C–Kit Proto Oncogene. Cell (1990) 63:167–174 (Exhibit 35).

Yarden, Y., et al. Human Proto–Oncogene C–Kit: A New Cell Surface Recept Tyrosine Kinase For An Unidentified Ligand. The EMBO Journal (1987) 6:3341–3351 (Exhibit 36).

Zsebo, K.M., et al. Identification, Purification, and Biological Characterization of Hematopoietic Stem Cell Factor From Buffalo Rat Liver–Conditioned Medium. Cell (199) 63:195–201 (Exhibit 37).

Zsebo, K.M., et al. Stem Cell Factor Is Encoded At The SI Locuse of the Mouse and is the Ligand for the C–Kit Tyrosine Kinase Receptor. Cell (1990) 63:213–224 (Exhibit 38).

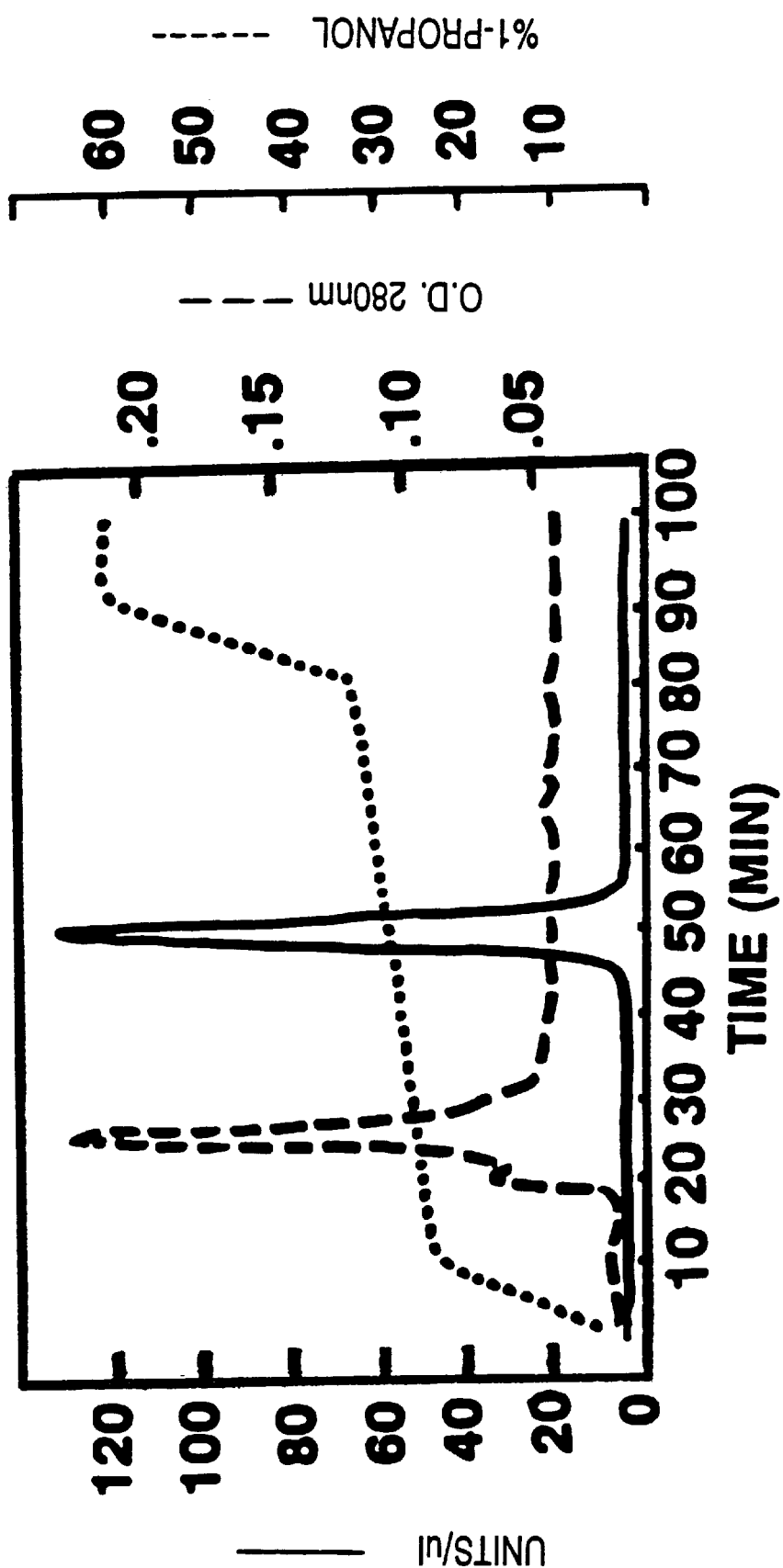

ANALYTICAL C 18

FIGURE 3A
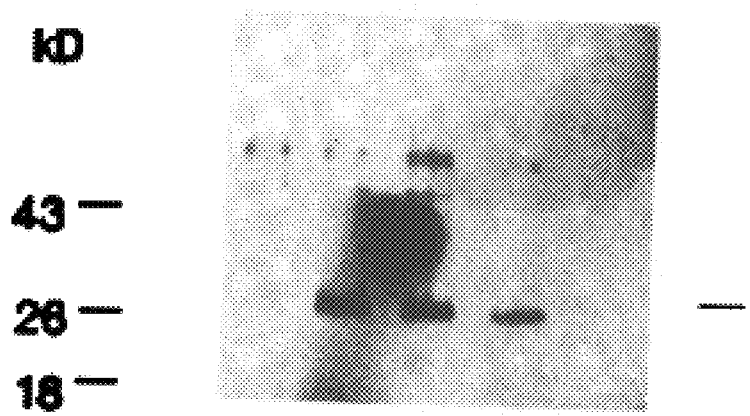
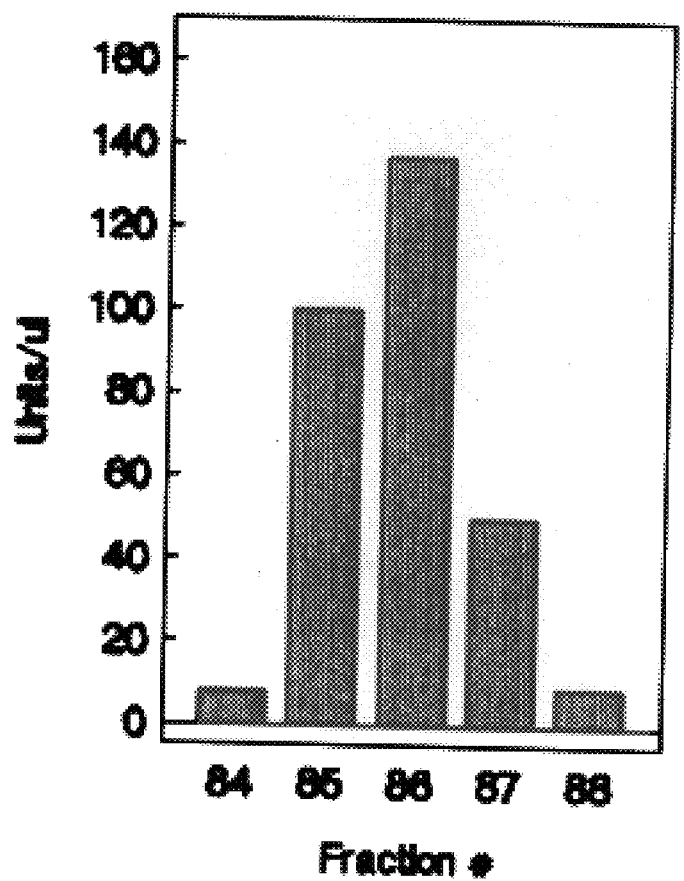

FIGURE 3B
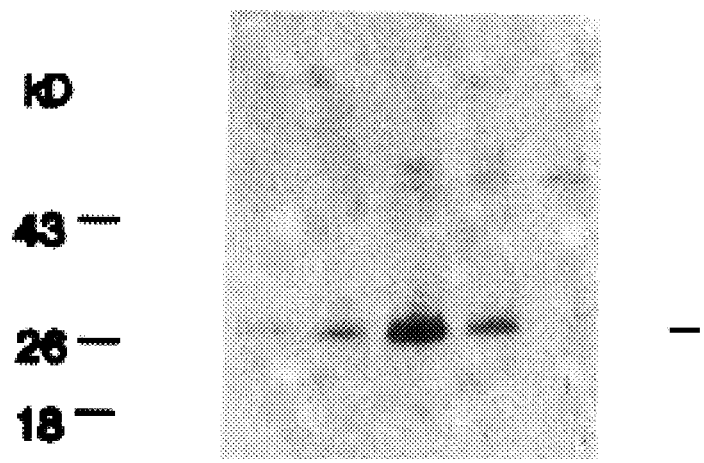
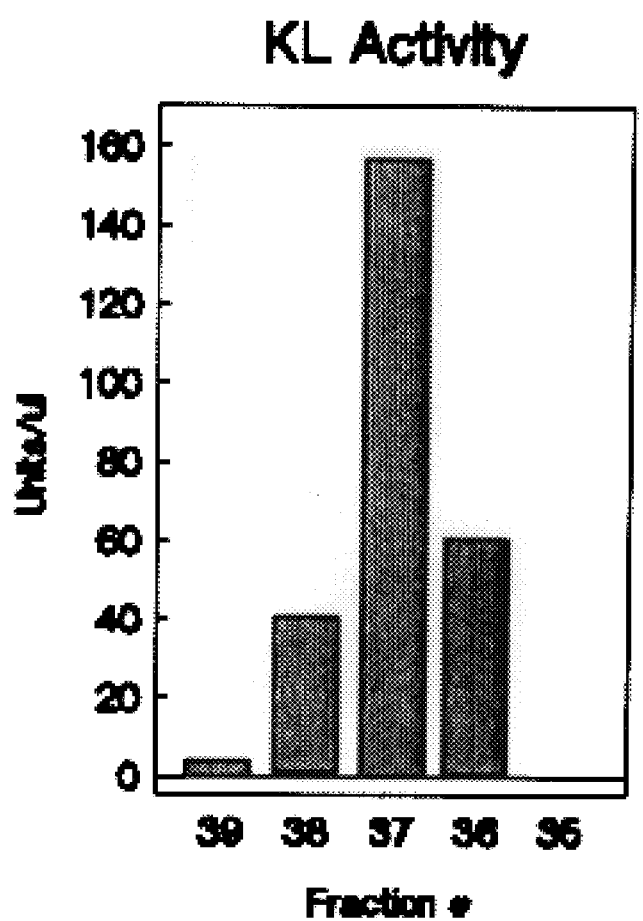

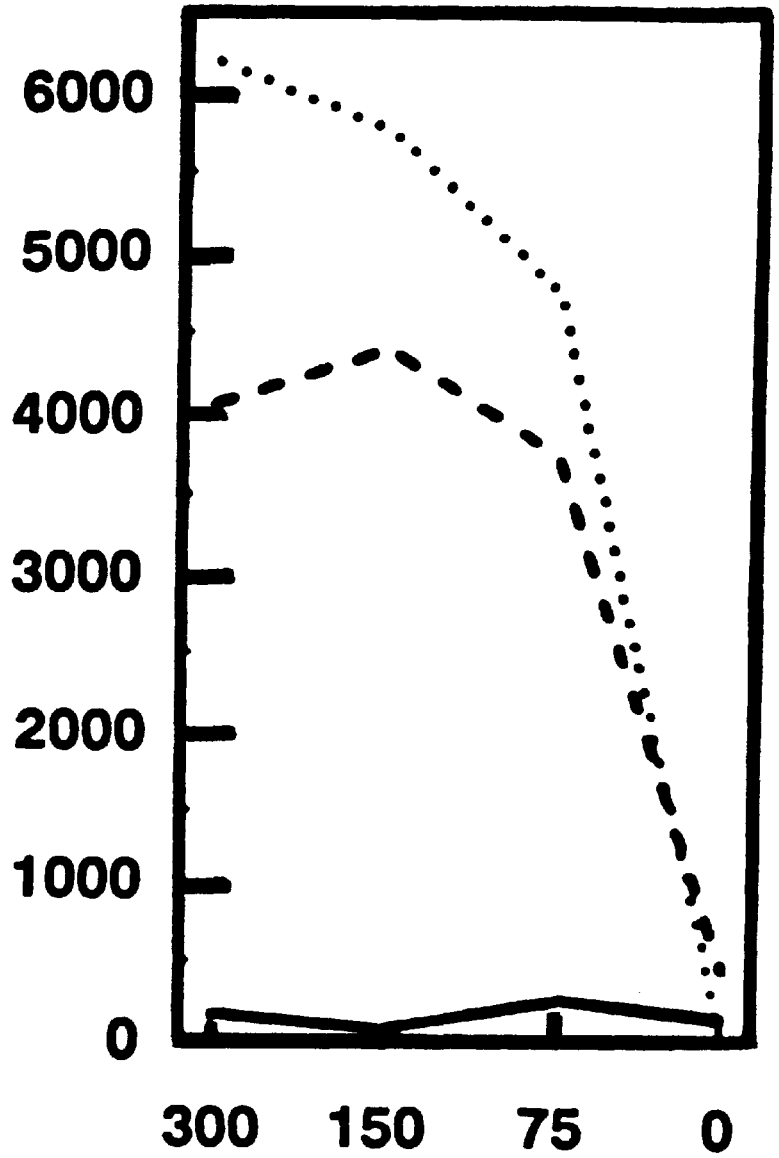

Berberine Sulfate Staining

Bone Marrow Derived Mast Cells

Peritoneal Mast Cells

C-KIT SURFACE EXPRESSION

BONE MARROW DERIVED MAST CELLS

PERITONEAL MAST CELLS

FIGURE 8

```
                    10                              20
KEIXGNPVT  D  N  V  K  D  I  T  K  L  V  A  N  L
              C  G     T  C
5' aagcttGATAATGTAAAGACATTACAAAACTGGTGGCAAATCTT
              T     A cgccaagcttGATAATGTAAAGATATTAC    3'
5'            C  C  G  G  C  C
                 T        A
                 C
                        30
P  N  O  Y  N  I  T  L  N  Y  V  A  G  N    XVLP
                                        G  C         3'
CCAAATGACTATATGATAACCCTCAATTACGTGGCCCGGAATGgggatcc
                              C     A     C
                              C  A
3'  TTAATACAGCGGCCGTACcctaggggcc
              G  G  T  T  T
                    C  C  C
                    A  A  A                5'
```

FIGURE 11A

```
                                                                                        .SP.........
    .  .  .  .  .  .  .  .  .  .  M  K  K  T  Q  T  W  I  I  T  C  I  Y  L  Q    15
    |------                                                             
GCGGTGCCTTTCCTTATGAAGAAGACACAAACTTGGATTATCACTTGCATTTATCTTCAA

L  L  F  N  P  L  V  K  T  K  E  I ⓒ G  N  P  V  T  Q    35
            |--|
CTGCTCCTATTTAATCCTCTCGTCAAAACCAAGGAGATCTGCGGGAATCCTGTGACTGAT

M  V  K  Q  I  T  K  L  V  A  N  L  P  N  D  Y  N  I  T  L    55
AATGTAAAAGACATTACAAAACTGGTGGCAAATCTTCCAAATGACTATATGATAACCCTC

M  Y  V  A  G  N  D  V  L  P  S  N ⓒ W  L  R  D  N  V  I    75
AACTATGTCGCCGGGATGGATGTTTTGCCTAGTCATTGTTGGCTACGACATATGGTAATA
```

FIGURE 11B

```
    Q   L   S   L   S   L   T   T   L   L   D   K   F   S   N   I   S   E   G   L    95
    CAATTATCACTCAGCTTGACTACTCTTCTGGACAAGTTCTCAAATATTTCTGAAGGCTTG

S   M   Y   S   I   I   D   K   L   G   K   I   V   D   Q   L   V   L  (C)  M   115
    AGTAATTACTCCATATCATAGACAAACTTGGGAAAATAGTGGATCAGCTCGTGTATGCATG

E   E   N   A   P   K   N   I   K   E   S   P   K   R   P   E   T   R   S   F   135
    GAAGAAAACGCACCGAAGAATCTCCGAAGAGGCCAGAAACTAGAAACTAGATCCTTT

T   P   E   E   F   F   S   I   F   N   R   S   I   D   A   F   K   D   F   M   155
    ACTCCTGAAGAATTCTTTAGTATTTCAATAGATCCATTGATGCCTTTAAGGACTTTATG

V   S   S   D   T   S  (D)  V   L   S   S   T   L   G   P   E   K   D   S    175
    GTGGCATCTGACACTAGTGACTGACTGTGCTCTTCAACATTAGGTCCCGAGAAAGATTCC
```

FIGURE 11C

```
  R   V   S   V   T   K   P   F   M   L   P   P   V   A   A   S   S   L   R   N    195
AGAGTCAGTGTCACAAAACCATTTATGTTACCCCCTGTTGCAGCCAGCTCCCTTAGGAAT

D   S   S   S   N   R   K   A   A   K   S   P   E   D   S   G   L   Q   W        215
GACAGCAGTAGCAGTGATAGGAAAAGCCGCAAAGTCCCCTGAAGACTCGGGCCTACAATGG

|·········································TMS······················|
  T   A   N   A   L   P   A   L   I   S   L   V   I   G   F   A   F   G   A   L    235
ACAGCCAATGGCATTGCCGGCTCTCATTTCGCTTGTAATTGGCTTTGCTTTTGGAGCCTTA
```

```
  ....|
      Y   W   K   K   K   Q   S   S   L   T   R   A   V   E   N   I   Q   I   N   E   255
TACTGGAAGAAGAAACAGTCAAGTCTTACAAGGGCAGTTGAAAATATACAGATTAATGAA

E   C   N   E   I   S   M   L   Q   Q   K   E   R   E   F                           270
GAGGATAATGAGATAAGTATGCTGCAACAGAAAGAGAGAGAATTT
```

Silver

```
GGGACTATCTGCAGCCCGCTGCTGGTGCAATATGCTGGAGCTCCAGAACAGCTAAACGGAG        60

TCGCCACACCGCTGCCTGGGCTGGATCGCCAGCCCTGCCTTCCTTATGAAGAAGACACAA       120
                                              M  K  K  T  Q          5
             SP
ACTTGGATTATCACTTGCATTTATCTTCAACTGCTCCTATTTAATCCTCTGTCAAAACC        180
 T  W  I  T  C  I  Y  L  Q  L  L  F  N  P  L  V  K  T              25
AAGGAGATCTGCGGGAATCCTGTGACTGATATGTAAAAGACATTACAAAACTGGTGGCA        240
 K  E  I  C  G  N  P  V  T  D  N  V  K  D  I  T  K  L  V  A        45
AATCTTCCAAATGACTATATGATAACCCTCAACTATGTCGCGGGATGGATGTTTTGCCT        300
 N  L  P  N  D  Y  M  I  T  L  N  Y  V  A  G  M  D  V  L  P        65
AGTCATTGTTGGCTACGAGATATGGTAATACAATTATCACTCAGCTTGACTACTCTTCTG        360
 S  H  C  W  L  R  D  M  V  I  Q  L  S  L  T  T  L  L              85
GACAAGTTCTCAAATATTTCTGAAGGCTTGAGTAATTACTCCATCATAGACAAACTTGGG        420
 D  K  F  S  N  I  S  E  G  L  S  N  Y  S  I  I  D  K  L  G       105
AAAATAGTGATGATGACCTCGTTATGCATGGAAGAAAACGCACCGAAGAATTCTTTAGTATTTCAAT    480
 K  I  V  D  D  L  V  L  C  M  E  E  N  A  P  K  N  I  K  E       125
TCTCCGAAGAGGCCAGAAACTAGATCCTTTACTCCTGAAGAATTCTTTAGTATTTCAAT        540
 S  P  K  R  P  E  T  R  S  F  T  P  E  E  F  F  S  I  F  N       145
AGATCCATTGATGCCTTTAAGGACTTTATGGTGGCATCTGACTAGTGACTGTGTGCTC        600
 R  S  I  D  A  F  K  D  F  M  V  A  S  D  T  S  D  C  V  L       165
```

FIGURE 17(CONT)

```
                                                          ▽
TCTTCAACATTAGTCCCGAGAAAGATTCCAGAGTCAGTGTCACAAAACCATTTATGTTA  660
 S  S  T  L  G  P  E  K  D  S  R  V  S  V  T  K  P  F  M  L   185
                                                              ▼
CCCCCTGTTGCAGCTCCCTTAGGAATGACAGCAGTAGCAGTAATAGAAAGCCCGCA     720
 P  P  V  A  A  S  L  R  N  D  S  S  S  S  N  R  K  A  A      205
            ▲  ▲                                             ▽
GTCTCTCTTGACAA----                                                sl^d
AAGGCCCCTGAAGACTCGGGCCTACAATTGACAGCCATTGCCGGCTCTCATTTCG      780
 K  A  P  E  D  S  G  L  Q  W  T  A  M  A  L  P  A  L  I  S   225
 A  S  L  -                                                      sl^d
 TMS
CTTGTAATTGGCTTTGCTTTTGGAGCCTTATACTGGAAGAAGAAACAGTCAAGTCTTACA  840
 L  V  I  G  F  A  F  G  A  L  Y  W  K  K  K  Q  S  S  L  T   245
AGGGCAGTTGAAAATATACAGATTAATGAAGAGGATAAGTATGTTGCAACAG         900
 R  A  V  E  N  I  Q  I  N  E  E  D  N  E  I  S  M  L  Q  Q   265
                                                                 sl^d
----GGTGGAGAAGTCACTGATGACTGGAGAAAGGCTTGGCTCTATCATTGACA       960
                                                                 273
AAGAGAGAGAATTTCAAGAGGTGTAATTGTGGACGTATCAACATTGTTACCTTCGCACA
 K  E  R  E  F  F  Q  E  V  *
```

FIGURE 17(CONT)

```
         ▶
         GA
         GTGGCTGGTAACAGTTCATGTTGCTTCATAAATGAAGCAGCCTTAAACAAATTCCCATT  1020
         CTGTCTCAAGTGACAGACCTCATCCTTACCCGTCTTCTGCTACCCGTGACCCTGTGTGGAT  1080
         GATTCAGTTGTTGGAGCAGAGTGCTTCGCTGTGTGAACCCTGCACTGAATTATCATCTGTAA  1140
         AGAAAAATCTGCACGGAGGAGCAGGACTCTGGAGGTTTGCAAGTCTGGAGTTTGCAAGAAC  1200
         ATGTGTCCAGTCTACTTGCACCGTTTGCATGGCTTGGAAACGTCTGAGTGCTGAAAACC  1260
         CACCCAGCTTTGTCTTCAGTCACAACCTGCAGCCTGTGTTAATTATGTCTCTGCAAG  1320
         TAGATTTCAGCCCTGGATGGTGGGG                                    1344
```

COS-1

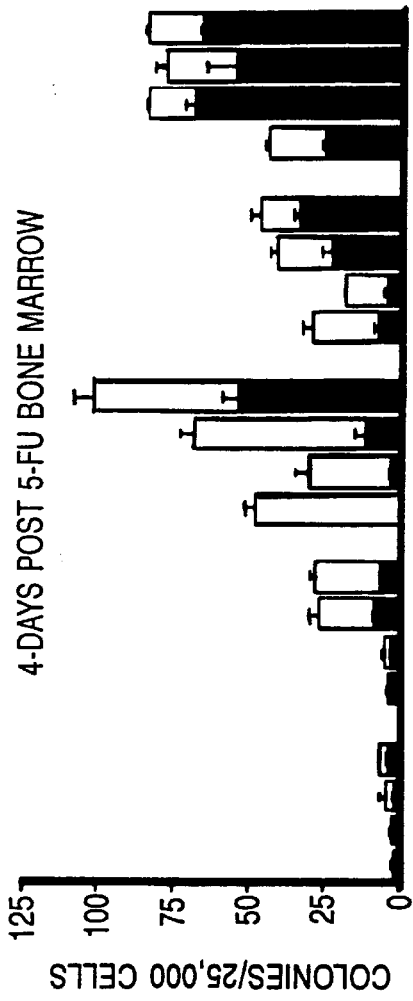
FIGURE 29C
FIGURE 29D

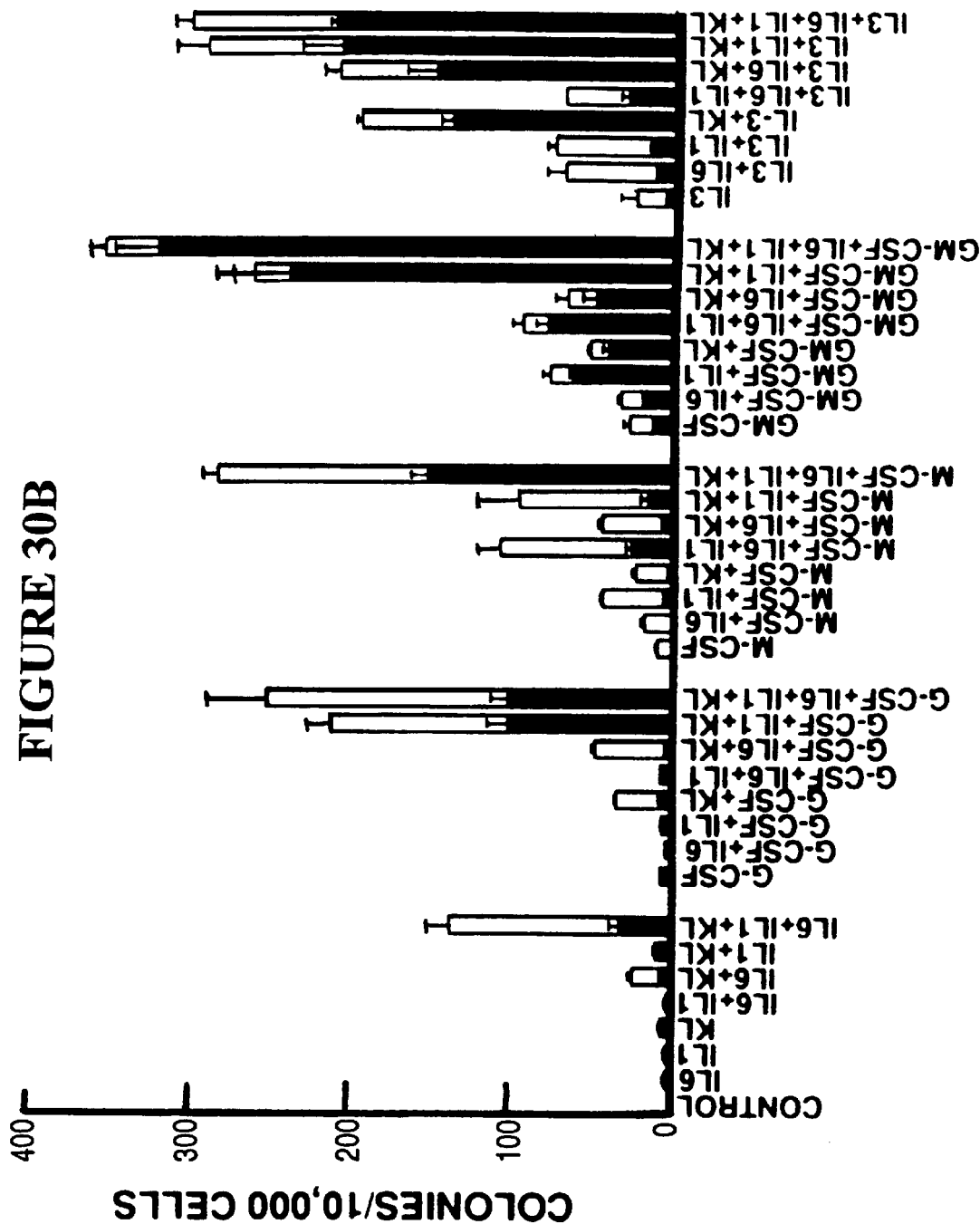

USE OF C-KIT LIGAND WITH TNF-α AND HEMATOPOIETIC FACTORS FOR THE EXPANSION OR DIFFERENTIATION OF HEMATOPOIETIC CELLS

This application is a continuation of application Ser. No. 08/325,240 filed Oct. 20, 1994, now U.S. Pat. No. 6,001,803, which was filed as international application PCT/US93/03640 on Apr. 16, 1993, and which entered the U.S. national stage under 35 U.S.C. §371 on Oct. 20, 1994; which is in turn a continuation-in-part of application Ser. No. 07/873,962, filed Apr. 23, 1992, and now abandoned. The contents of the prior applications are incorporated by reference herein.

The invention described herein was made in the course of work under Grant No. RO1-CA 32926 and ACS MV246D from the National Institute of Health and American Cancer Society, respectively. The United States Government has certain rights in this invention.

BACKGROUND OF THE INVENTION

Throughout this application various publications are referred by arabic numerals to within parenthesis. Full bibliographic citations for these references may be found at the end of the specification immediately preceding the claims. The disclosures for these publications in their entireties are hereby incorporated by reference into this application to more fully describe the state of the art to which this invention pertains.

The c-kit proto-oncogene encodes a transmembrane tyrosine kinase receptor for an unidentified ligand and is a member of the colony stimulating factor-1 (CSF-1)—platelet-derived growth factor (PDGF)—kit receptor subfamily (7, 41, 57, 23). c-kit was recently shown to be allelic with the white-spotting (W) locus of the mouse (9, 17, 35). Mutations at the W locus affect proliferation and/or migration and differentiation of germ cells, pigment cells and distinct cell populations of the hematopoietic system during development and in adult life (47, 51). The effects on hematopoiesis are on the erythroid and mast cell lineages as well as on stem cells, resulting in a macrocytic anemia which is lethal for homozygotes of the most severe W alleles (46), and a complete absence of connective tissue and mucosal mast cells (72). W mutations exert their effects in a cell autonomous manner (28, 46), and in agreement with this property, c-kit RNA transcripts were shown to be expressed in targets of W mutations (35). High levels of c-kit RNA transcripts were found in primary bone marrow derived mast cells and mast cell lines. Somewhat lower levels were found in melanocytes and erythroid cell lines.

The identification of the ligand for c-kit is of great significance and interest because of the pleiotropic effects it might have on the different cell types which express c-kit and which are affected by W mutations in vivo. Important insight about cell types which may produce the c-kit ligand can be derived from the knowledge of the function of c-kit/W. The lack of mast cells both in the connective tissue and the gastrointestinal mucosa of $W/W^V$ mice indicated a function for c-kit in mast cell development. Mast cells derived from bone marrow (BMMC) are dependent on interleukin 3 (IL-3) and resemble mast cells found in the gastrointestinal mucosa (MMC) (92, 93). Connective tissue mast cells derived from the peritoneal cavity (CTMC) in vitro require both IL-3 and IL-4 for proliferation (79, 75). The interleukins IL-3 and IL-4 are well characterized hematopoietic growth factors which are produced by activated T-cells and by activated mast cells (92, 94, 95, 96, 97). An additional mast cell growth factor has been predicted which is produced by fibroblasts (47). In the absence of IL-3, BMMC and CTMC derived from the peritoneal cavity can be maintained by co-culture with 3T3 fibroblasts (98). However, BMMC from $W/W^V$ mice as well as mice homozygous for a number of other W alleles are unable to proliferate in the fibroblast co-culture system in the absence of IL-3 (99, 100, 38). This suggested a function for the c-kit receptor in mature mast cells and implied that the ligand of the c-kit receptor is produced by fibroblasts. Huff and coworkers recently reported the stimulation of mast cell colonies from lymph node cells of mice infected with the nematode *Nippostronglyus brasiliensis* by using concentrated conditioned medium from NIH 3T3 fibroblasts (84). A short term mast cell proliferation assay was developed which means to purify a fibroblast derived activity (designated KL) which, in the absence of IL-3, supports the proliferation of normal BMMC's and peritoneal mast cells, but not $W/W^V$ BMMC's. In addition, KL was shown to facilitate the formation of erythroid bursts (BFU-E). The biological properties of KL are in agreement with those expected of the c-kit ligand with regard to mast cell biology and aspects of erythropoiesis. The defect W mutations exert is cell autonomous; in agreement with this property, there is evidence for c-kit RNA expression in cellular targets of W mutations (35, 39). The recent characterization of the molecular lesions of several mutant alleles indicated that they are loss-of-function mutations that disrupt the normal activity or expression of the c-kit receptor (35, 100, 101, 36).

Mutations at the steel locus (Sl) on chromosome 10 of the mouse result in phenotypic characteristics that are very similar to those seen in mice carrying W mutations, i.e., they affect hematopoiesis, gametogenesis, and melanogenesis (5, 47, 51). Many alleles are known at the Sl locus; they are semidominant mutations, and the different alleles vary in their effects on the different cell lineages and their degree of severity (47, 51). The original Sl allele is a severe mutation. Sl/Sl homozygotes are deficient in germ cells, are devoid of coat pigment, and die perinatally of macrocytic anemia (5, 50). Mice homozygous for the Sl allele, although viable, have severe macrocytic anemia, lack coat pigment, and are sterile. Both $Sl^+$ and $Sl^d/+$ heterozygotes have a diluted coat color and a moderate macrocytic anemia but are fertile, although their gonads are reduced in size. In contrast to W mutations, Sl mutations are not cell autonomous and are thought to be caused by a defect in the micro-environment of the targets of these mutations (28, 30, 12). Because of the parallel and complementary characteristics of mice carrying Sl and W mutations, we and others had previously hypothesized that the Sl gene product is the ligand of the c-kit receptor (51, 9).

The proto-oncogene c-kit is the normal cellular counterpart of the oncogene v-kit of the HZ4—feline sarcoma virus (7). c-kit encodes a transmembrane tyrosine kinase receptor which is a member of the platelet derived growth factor receptor subfamily and is the gene product of the murine white spotting locus (9, 17, 23, 35, 41, 57). The demonstration of identity of c-kit with the W locus implies a function for the c-kit receptor system in various aspects of melanogenesis, gametogenesis and hematopoiesis during embryogenesis and in the adult animal (47,51). In agreement with these predicted functions c-kit mRNA is expressed in cellular targets of W mutations (3, 24, 25, 35, 39).

The ligand of the c-kit receptor, KL, has recently been identified and characterized, based on the known function of c-kit/W in mast cells (2, 14, 37, 38, 56, 58, 59). In agreement with the anticipated functions of the c-kit receptor in hematopoiesis KL stimulates the proliferation of bone marrow derived and connective tissue mast cells and in erythropoiesis, in combination with erythropoietin, KL promotes the formation of erythroid bursts (day 7–14 BFU-E). Furthermore, recent in vitro experiments with KL have demonstrated enhancement of the proliferation and differentiation of erythroid, myeloid and lymphoid progenitors when used in combination with erythropoietin, GM-CSF, G-CSF and IL-7 respectively suggesting that there is a role for the c-kit receptor system in progenitors of several hematopoietic cell lineages (27, 37).

Mutations at the steel locus on chromosome 10 of the mouse result in phenotypic characteristics that are very similar to those seen in mice carrying W mutations, i.e., they affect hematopoiesis, gametogenesis and melanogenesis (5, 47, 51). The ligand of the c-kit receptor, KL, was recently shown to be allelic with the murine steel locus based on the observation that KL sequences were found to be deleted in several severe Sl alleles (11, 38, 59). In agreement with the ligand receptor relationship between KL and c-kit, Sl mutations affect the same cellular targets as W mutations, however, in contrast to W mutations, Sl mutations are not cell autonomous and they affect the microenvironment of the c-kit receptor (12, 28, 30). Mutations at the steel locus are semidominant mutations and the different alleles vary in their effects on the different cell lineages and their degree of severity (47, 51). The original Sl allele is an example of a severe Sl mutation. Sl/Sl homozygotes are deficient in germ cells, are devoid of coat pigment and they die perinatally of macrocytic anemia (5,50). Mice homozygous for the $Sl^d$ allele, although viable, have severe macrocytic anemia, lack coat pigment and are sterile (6). Both Sl/+ and $Sl^d$/+ heterozygotes have a diluted coat color and a moderate macrocytic anemia, but they are fertile, although their gonads are reduced in size. Southern blot analysis of Sld/+ DNA by using a KL cDNA as a probe indicated an EcoR1 polymorphism, suggesting that this mutation results from a deletion, point mutation or DNA rearrangement of the KL gene (11).

SUMMARY OF INVENTION

A pharmaceutical composition which comprises the c-kit ligand (KL) purified by applicants or produced by applicants' recombinant methods in combination with other hematopoietic factors and a pharmaceutically acceptable carrier is provided as well as methods of treating patients which comprise administering to the patient the pharmaceutical composition of this invention. This invention provides combination therapies using c-kit ligand (KL) and a purified c-kit ligand (KL) polypeptide, or a soluble fragment thereof and other hematopoietic factors. It also provides methods and compositions for ex-vivo use of KL alone or in combination therapy. A mutated KL antagonist is also described. Such an antagonist may also be a small molecule. Antisense nucleic acids to KL as therapeutics are also described. Lastly, compositions and methods are described that take advantage of the role of KL in germ cells, mast cells and melanocytes.

This invention provides a nucleic acid molecule which encodes an amino acid sequence corresponding to a c-kit ligand (KL) and a purified c-kit ligand (KL) polypeptide.

BRIEF DESCRIPTION OF THE FIGURES

FIGS. 2A–2D. Chromatographic profiles of the purification of KL.
  A. Gel filtration chromatography on ACA 54 Ultrogel. Absorbance at 280 nm is shown by a broken line and bio-activity by a solid line. The position of the elution of protein size markers is indicated in kD.
  B. Anion exchange FPLC on a DEAE-5PW column. The NaCl gradient is indicated by a dotted line.
  C. Separation on semi-preparative C18 column. The 1-propanol gradient is indicated by a dotted line.
  D. Separation on analytical C18 column.

FIGS. 3A–3C. Electrophoretic analysis of KL. Material from individual fractions was separated by SDS/PAGE (12%) and stained with silver. The position of KL (28–30 kD) is indicated by an arrow. KL activity of corresponding fractions is shown below.
  Analysis of 0.5 ml fractions from analytical C18 column eluted with ammonium acetate buffer and 1-propanol gradient.
  Analysis of 0.5 ml fractions from analytical C4 column eluted with aqueous 0.1% TFA and absence of 2-mercapto-ethanol.

FIGS. 4A–4C. Proliferation of W* mutant mast cells in response to KL. Mast cells were derived from individual fetal livers from W/+×W/+ mating, or bone marrow of wildtype, $W^V$ and $W^{41}$ heterozygotes and homozygoses. The proliferation characteristics of mutant mast cells was determined by using increasing concentrations of KL in a proliferation assay. Homozygous mutant mast cells are indicated by a solid line, heterozygotes mutant mast cells by a broken line and wildtype mast cells by a dotted line, except for W where normal fetuses may be either +/+ or W/+.

FIG. 8. N-terminal amino acid sequence of KL and deduction of the corresponding nucleic acid sequence by PCR. Top line: N-terminal amino acid sequence (residues 10–36) of KL. Middle Line: Nucleotide sequences of three cDNAs obtained by cloning the 101 bp PCR product (see FIG. 10) into M13 and subsequent sequence determination. Bottom Line: sequences of the degenerate sense and anti-sense primers used for first-strand cDNA synthesis and PCR. The amino acid sequence also is identified as SEQ ID:NO:2.

FIG. 17. Nucleotide and predicted amino acid sequence of KL-1, KL-2 and KL-Sl$^d$ cDNAs. The nucleotide sequence of the KL cDNA obtained from the Balb3T3 cell plasmid cDNA library is shown. The RT-PCT products from different tissues and Sl$^d$/+ total RNA, KL-1, KL-2 and KL-Sl$^d$, were subcloned and subjected to sequence analysis. Open triangles indicate the 5' and 3' boundaries of the exon which is spliced out in KL-2; the closed triangles indicate the deletion endpoints in the Sl$^d$ cDNA. The 67 nucleotide inset sequence of the Sl$^d$ cDNA is shown above the KL cDNA sequence. Arrows indicate the putative proteolytic cleavage sites in the extracellular region of KL-1. The signal peptide (SP) and transmembrane segment (TMS) are indicated with overlying lines.

containing the phorbol ester PMA (1 μM and c) containing the calcium ionophore A23187 (1 μM). Supernatants and cell lysates were immunoprecipitated with anti-KL rabbit serum. Immunoprecipitates were analyzed by SDS-PAGE (12%). Migration of molecular weight markers is indicated in kilo daltons (kD).

Figure 23A:
Figure 23B:
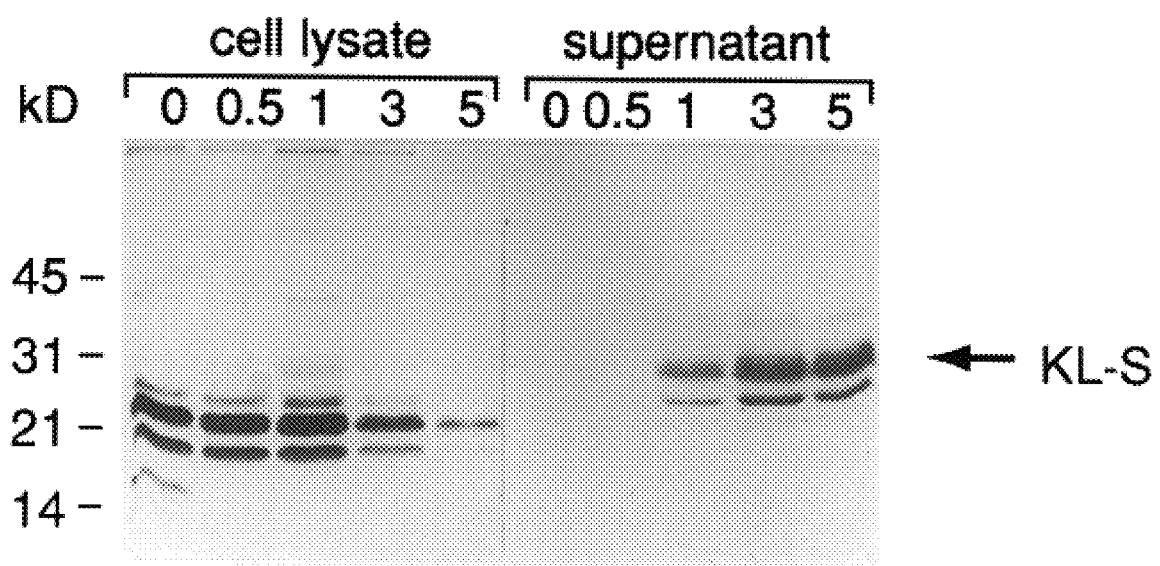

FIGS. 23A–23B. Biosynthetic characteristics of KL-Sl$^d$ and KL-S protein products in COS cells.

Figure 24:
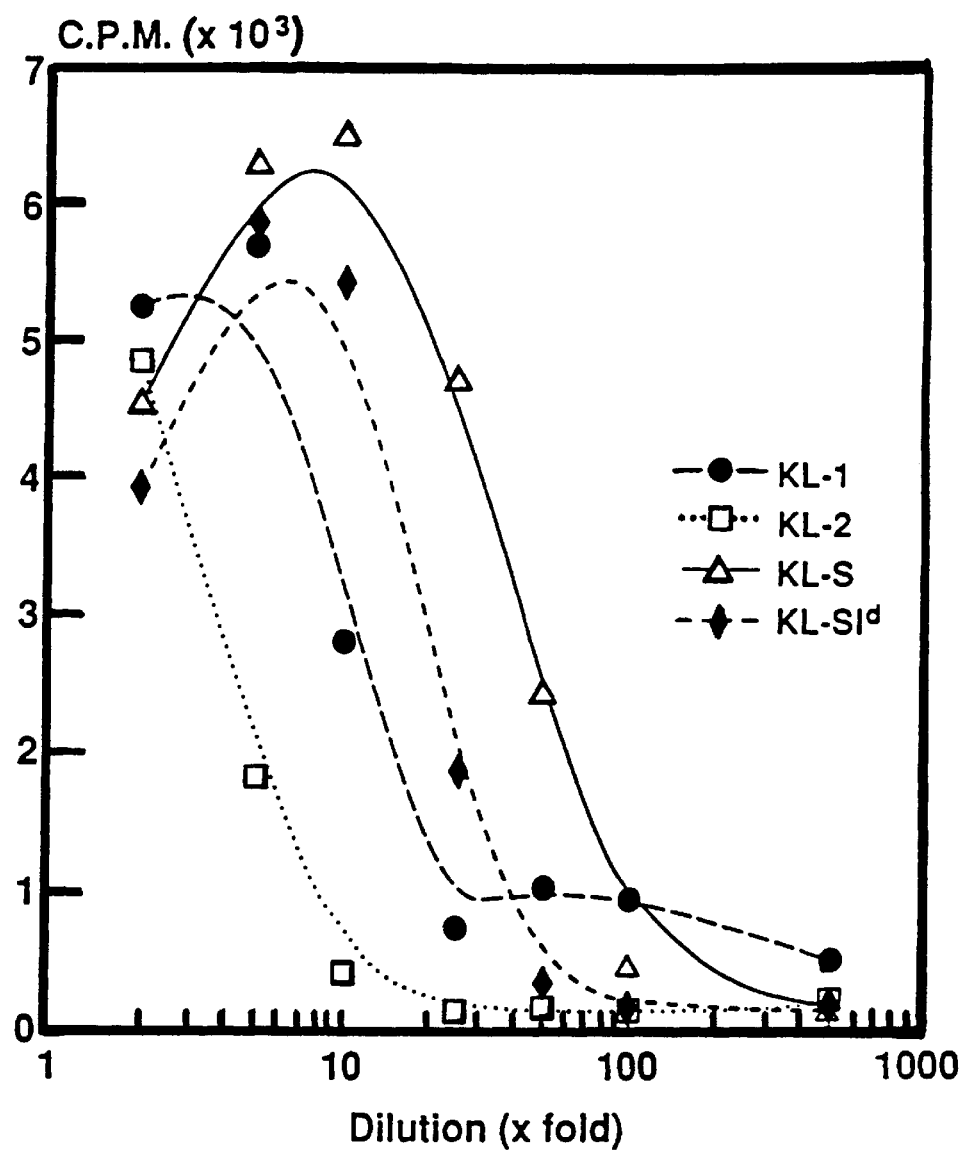

FIG. 24. Determination of biological activity in COS cell supernatants. Supernatants from COS cells transfected with the KL-1, KL-2, KL-Sl$^d$ and KL-S expression plasmids were assayed for activity in the mast cell proliferation assay. Serial dilutions of supernatant were incubated with BMMCs and incorporation of $^3$H-thymidine was determined from 24–30 hours of culture.

Figure 25:
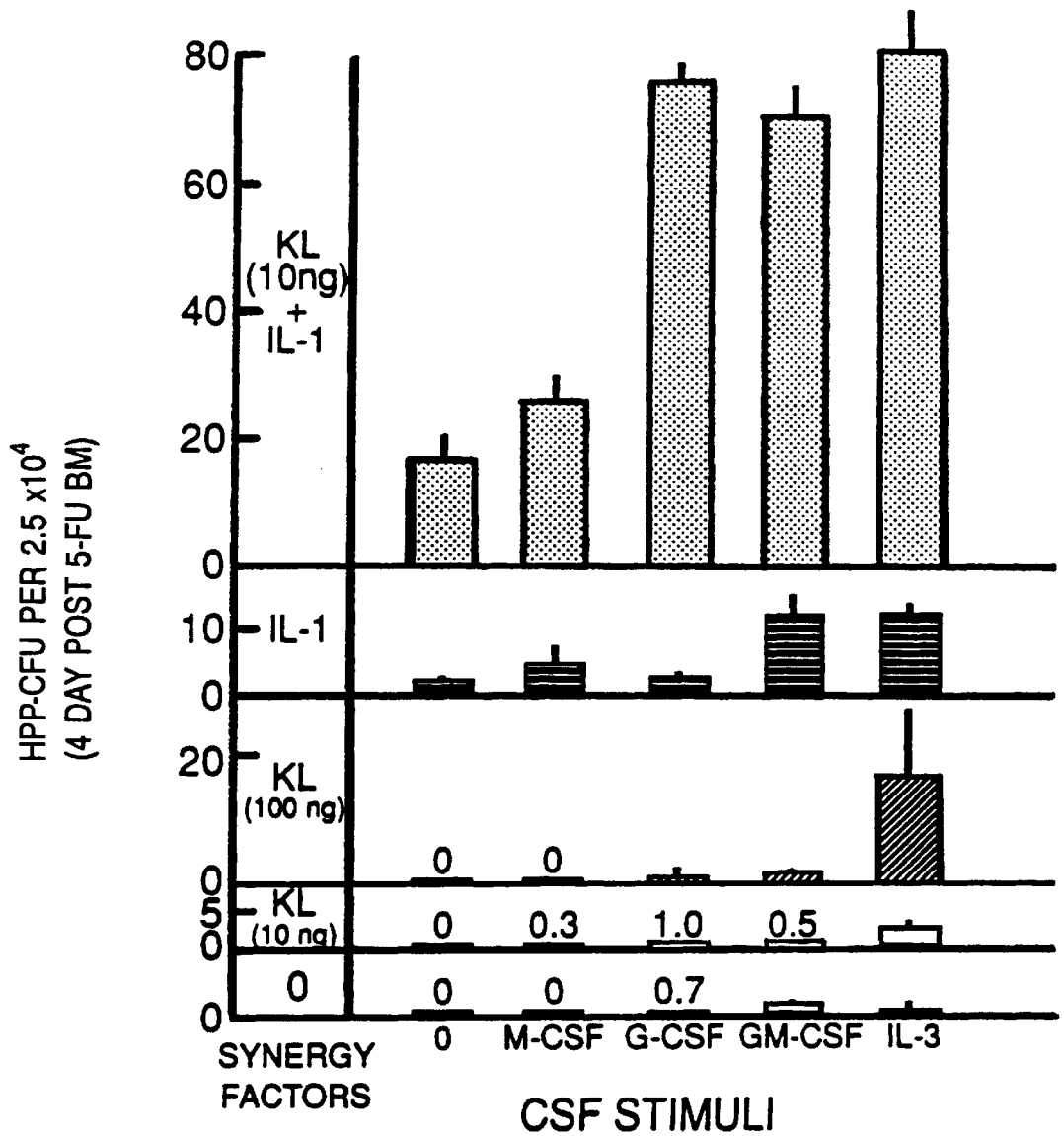

FIG. 25. Synergism between recombinant human (rh) IL-1β (100 U/mL, rmKL (10 to 100 ng/mL), and rhM-CSF, rhG-CSF, and rmIL-3 (all at 1,000 U/mL) in the HPP-CFU assay. Four-day post-5-FU murine bone marrow was cultured in 60-mm Petri dishes with a 2 mL 0.5% agarose underlayer containing cytokines, overlayed with 1 mL of 0.36% agarose containing $2.5 \times 10^4$ marrow cells. Following a 12-day incubation under reduced oxygen conditions, cultures were scored from colonies of greater than 0.5 mm diameter.

Figure 26:
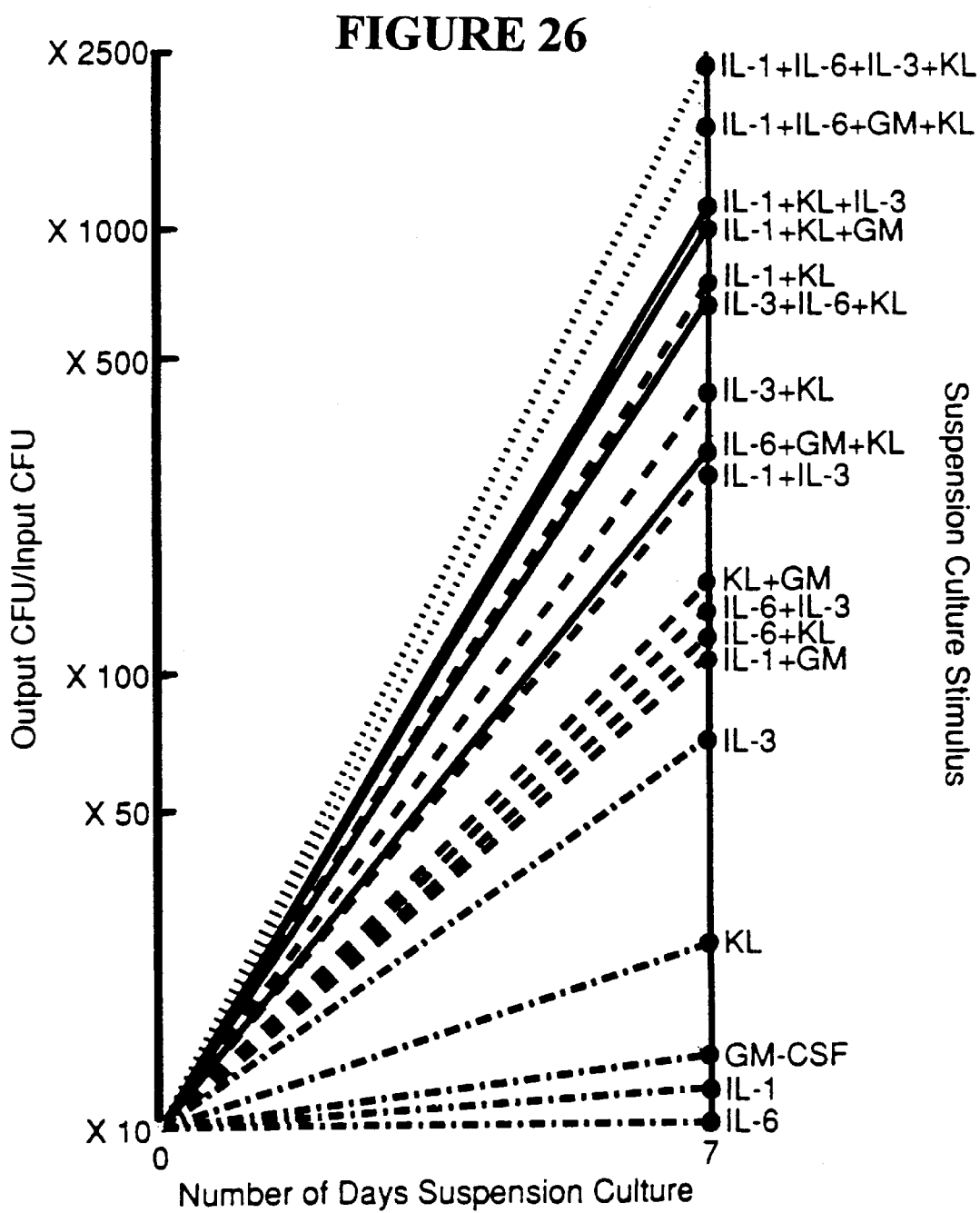

FIG. 26. Secondary CFU-GM or delta assay showing the fold increase of GM-CSF-responsive CFU-GM in a 7-day suspension culture of 24-hour post 5-FU murine bone marrow. Marrow cells ($2/5 \times 10^5$ /mL) were cultured for 7 days with the cytokine combinations indicated and recovered cells recloned in a GM-CSF-stimulated colony assay. The fold increase is the ratio of the number of CFU-GM recovered in the secondary clonogenic assay over the input number of CFU-GM determined in the primary clonogenic assay over the input number of CFU-GM determined in the primary clonogenic assay with GM-CSF, rmKL was used as 20 ng.mL, rhIL-6 at 50 ng/mL, rhIL-1β at 100 U/mL, and rhGM-CSF or rmIL-3 at 1,000 U/mL.

Figure 27:

FIG. 27. Amplification of hematopoiesis in cultures of 24 hours post 5-FU bone marrow cultured for 7 days in suspension in the presence of IL-1+IL-3+KL. Cells, $10^4$, (after substraction of granulocytes and lymphocytes) and containing 2.5% HPP-CFU responsive to IL-1+IL-3+KL in primary clonogenic assay, were incubated in suspension and the total cells and HPP-CFU responsive to IL-1+IL-3+KL, or CFU-GM responsive to rmGM-CSF were determined after 7 days in secondary clonogenic assays. The calculations are based on the ratio of output cells to input HPP-CFU.

Figure 28:
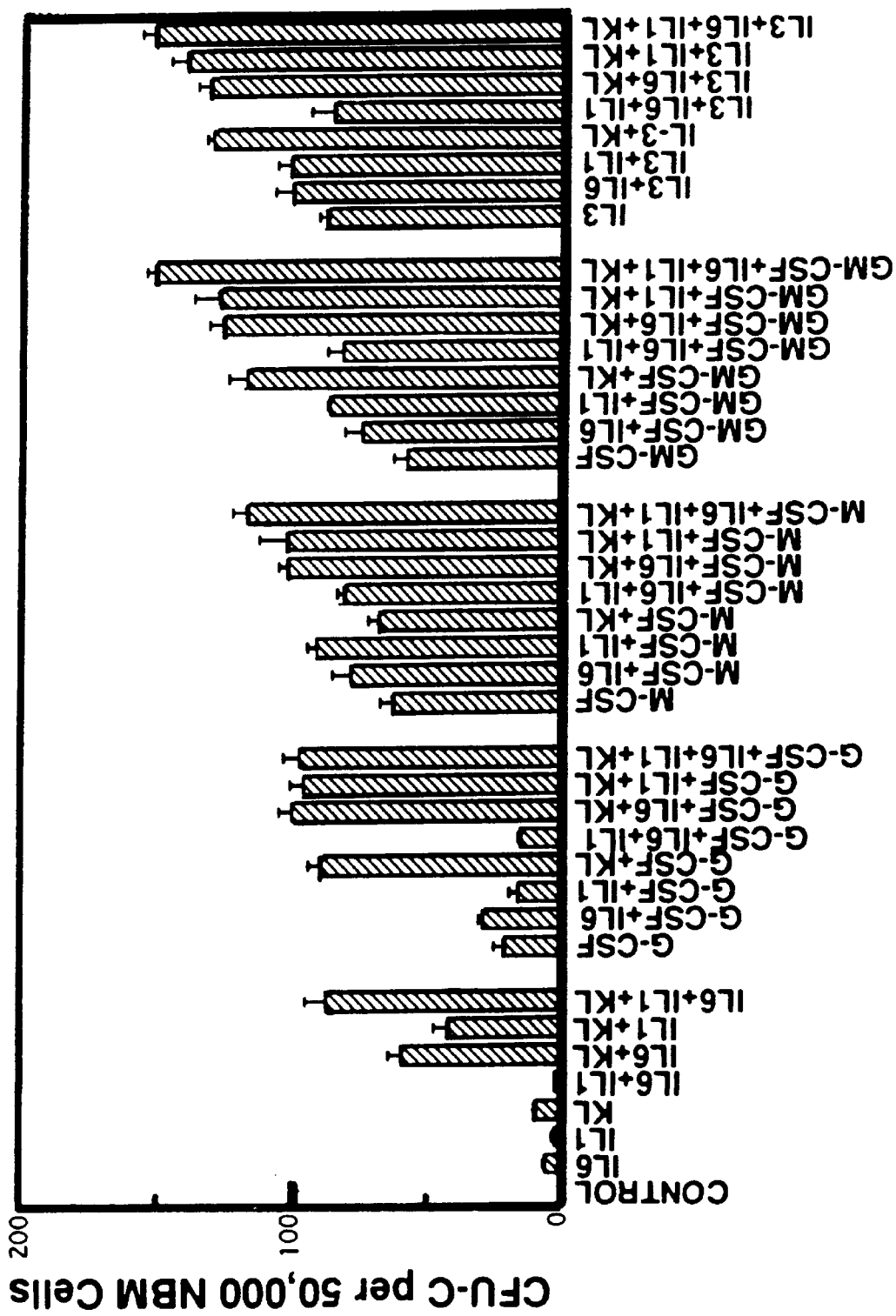
Figure 29A:
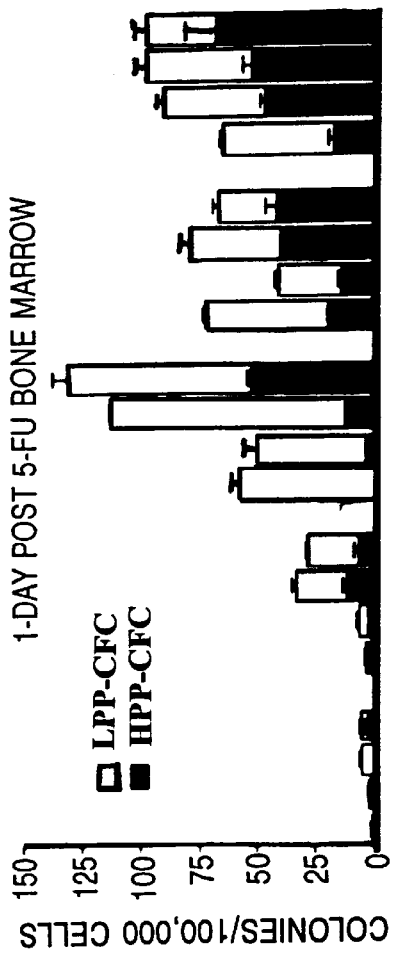
Figure 29B:
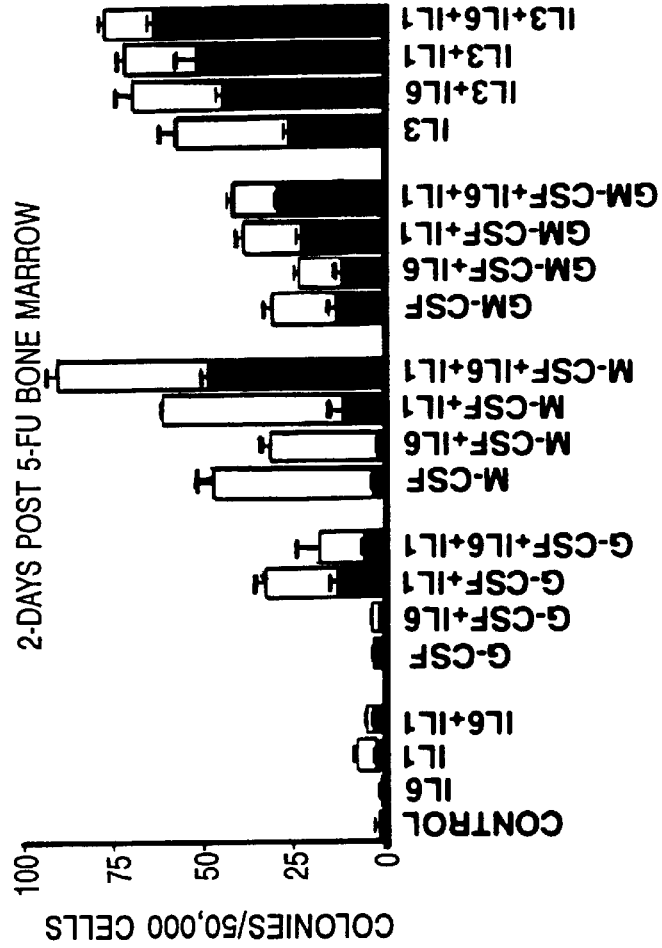

FIG. 28. The effects of IL-6, IL-1, and KL alone or in combination on colony growth from normal murine bone marrow. Control cultures were grown in the absence of any growth factors. The seven combinations or IL-6, IL-1, and KL were tested alone or in combination with the CSF's G-CSF, M-CSF, GM-CSF, and IL-3. The data are presented as the mean plus the SE of triplicate cultures.

FIGS. 29A–29D. Synergism among IL-6, IL-1 and CSF's in the stimulation of HPP-CFC from 5-FU-purged bone marrow. Bone marrow was harvested 1–7 days after the administration of 5-FU (top to bottom) and grown in the presence of G-CSF, M-CSF, and IL-3±IL-6, IL-1 or IL-6 plus IL-1. The data are presented as total CFU-C (HPP-CFC plus LPP-CFC) per $1 \times 10^5$ to $1 \times 10^4$ (d1 5-FU to d7 5-FU) bone marrow cells. The data represent the man plus SE of triplicate cultures.

Figure 30A:
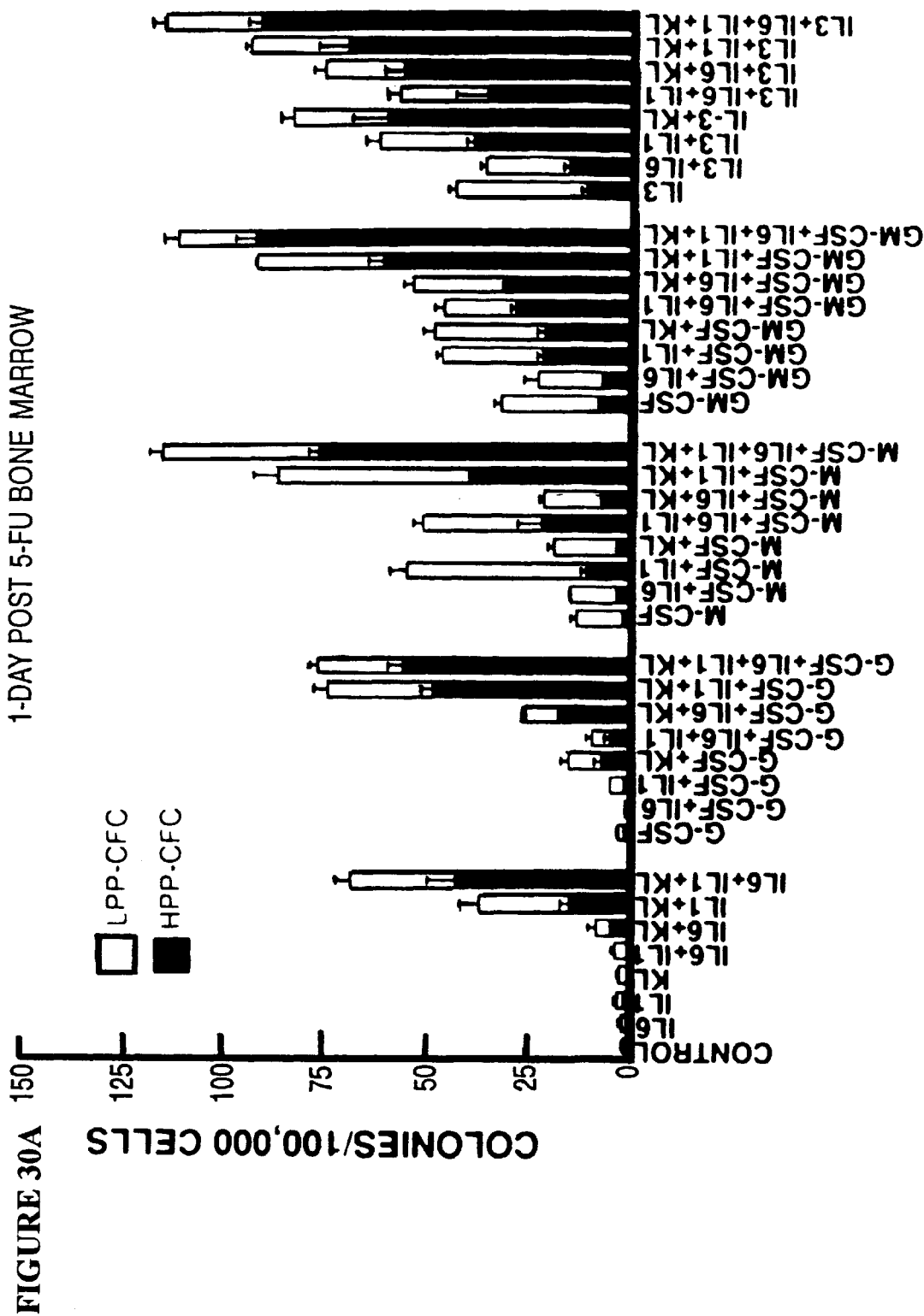

FIGS. 30A–30B. KL synergistically stimulates HPP-CFC in combination with other cytokines. As in FIG. 28, 40 combinations of cytokines were tested for their ability to stimulate CFU-C (HPP-CFC plus LPP-CFC) from BM harvested after 5-FU injection. Colony numbers represent the mean plus SE of triplicate cultures of $1 \times 10^5$ d1 5-FU BM or $1 \times 10^4$ d7 5-FU BM cells.

Figure 31:
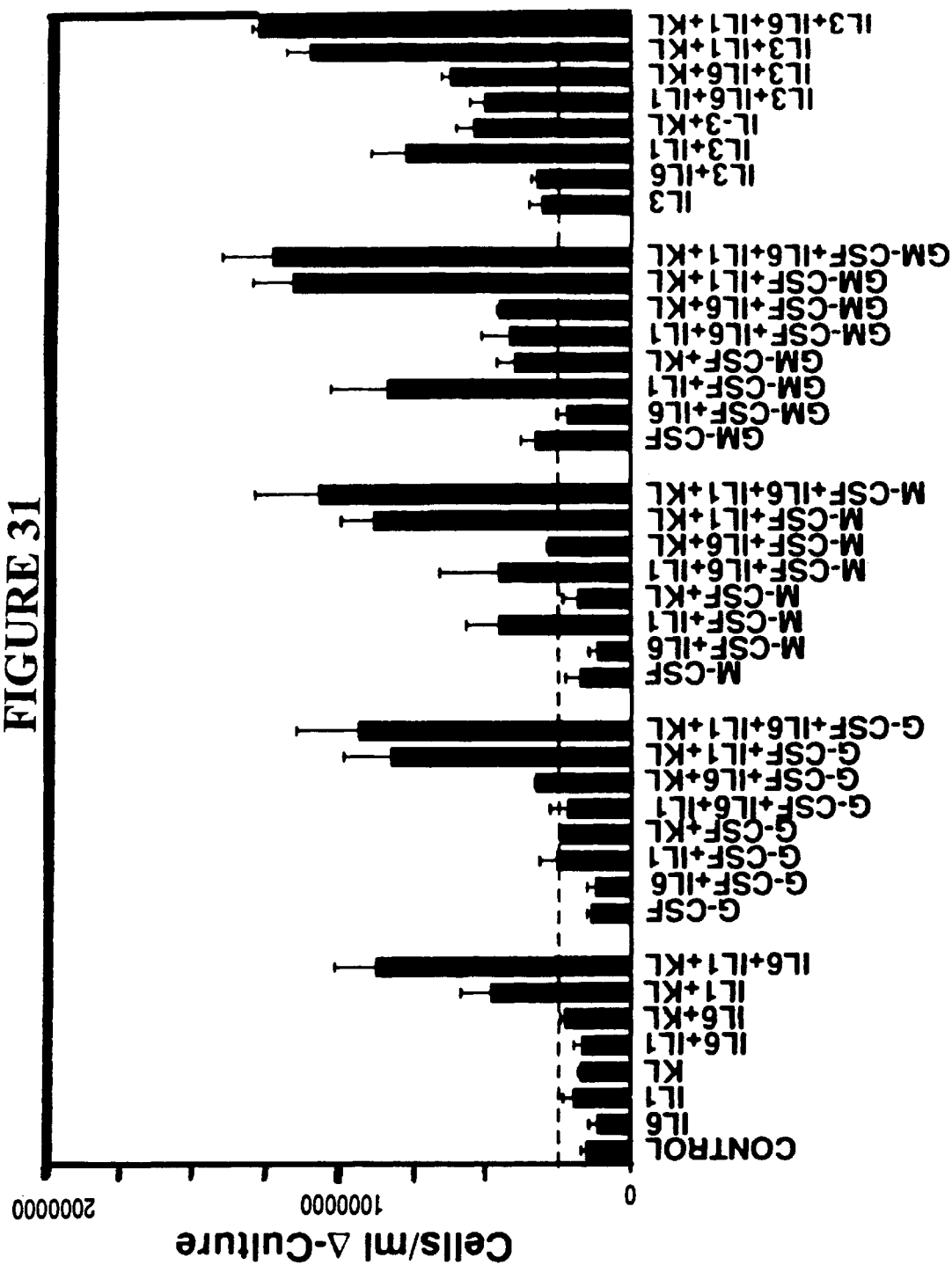

FIG. 31. The expansion of total cell numbers in $^\Delta$-cultures requires the combined stimulation of multiple growth factors. The numbers of nonadherent cells present in $^\Delta$-cultures after 7 days of growth were determined as described in the materials and methods. The dashed line represents the $2.5 \times 10^5$ d1 5-FU BM cells used to inoculate the cultures. The morphologies of the recovered cells are discussed in the text. The data are presented as the mean plus SE 2–16 experiments.

Figure 32:
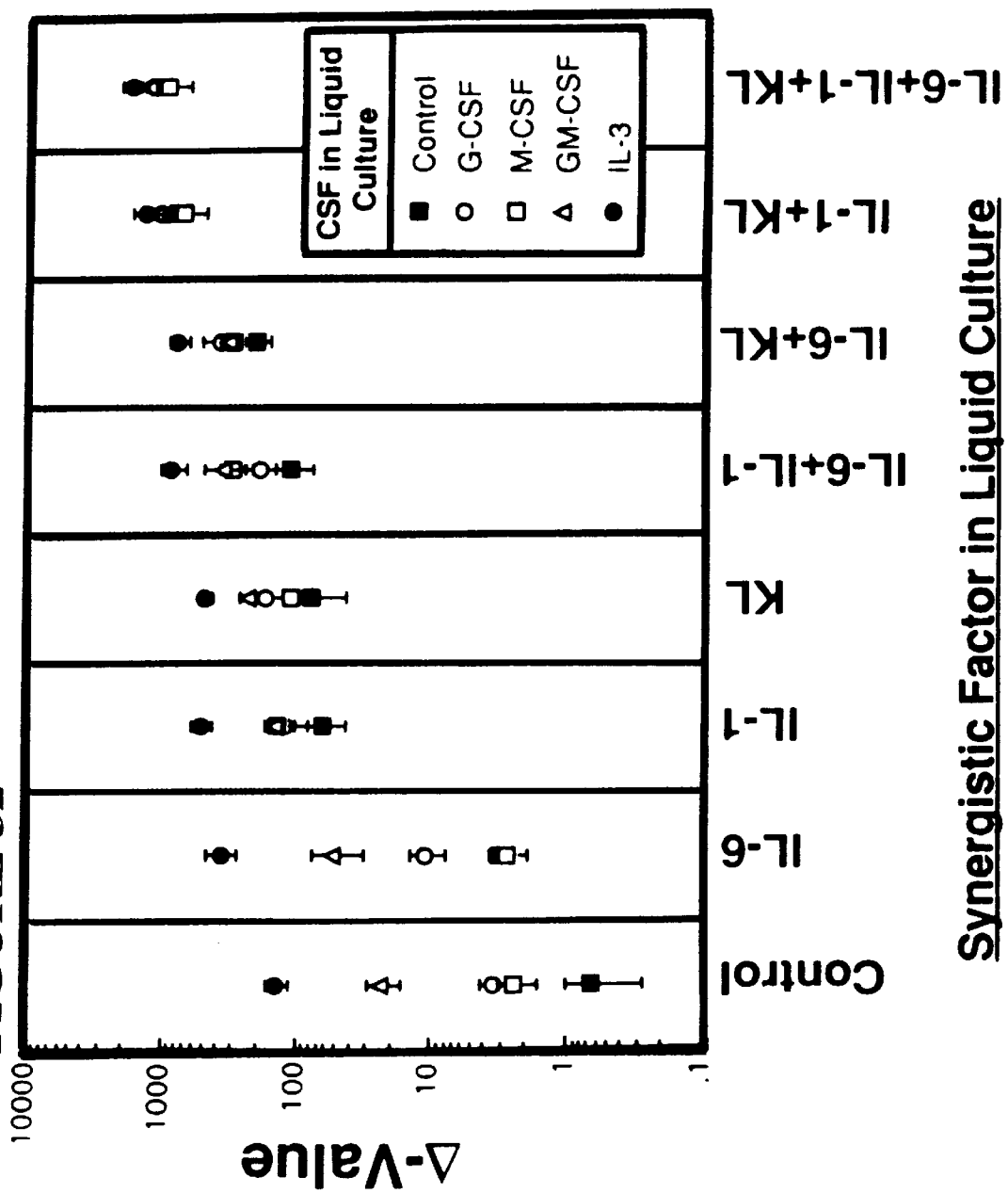

FIG. 32. IL-6, IL-1, and KL, alone or in combination, are synergistic with CSF's in the expansion of LPP-CFC in $^\Delta$-cultures. The for LPP-CFC grown in the presence of G-CSF, M-CSF, GM-CSF, IL-3 or IL-1 plus IL-3 were calculated as described in the materials and methods. The $^\Delta$-values were calculated from the average of triplicate primary and secondary colony counts. The results are presented as the mean±SE of 6–11 $^\Delta$-values pooled from two or three experiments. Note that the LPP-CFC $^\Delta$-values are on a log scale.

Figure 33:
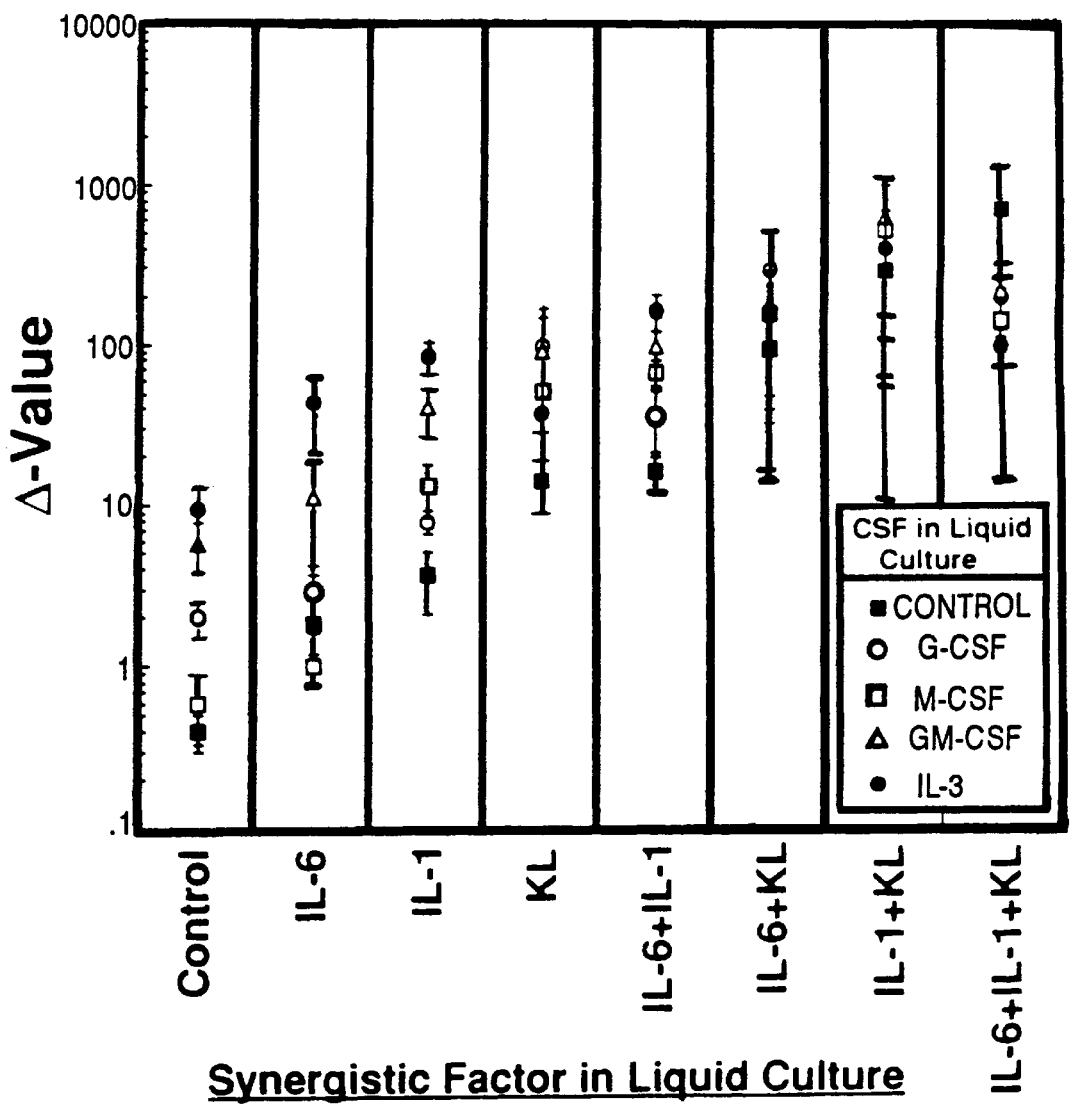

FIG. 33. IL-6, IL-1 and KL alone or in combination, act with CSF's in the expansion of HPP-CFC in $^\Delta$-cultures. All HPP-CFC were grown in the presence of IL-1 plus IL-3. The $^\Delta$-values were calculated from the average of triplicate primary and secondary colony counts. The results are presented as the mean±SE of 2–11 experiments. Note that the HPP-CFC $^\Delta$-values are on a log scale.

Figure 34:
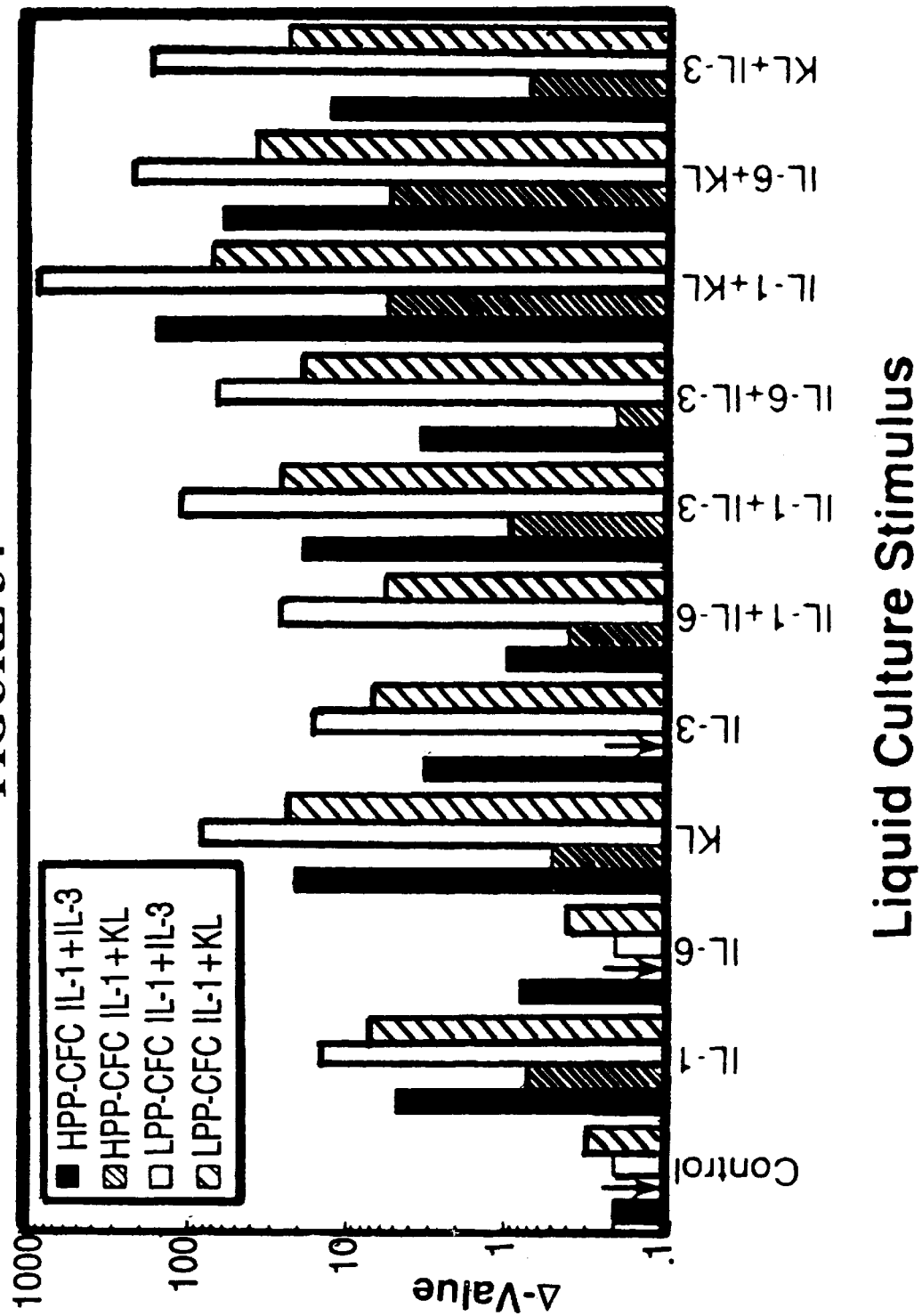

FIG. 34. Progenitors responsive to IL-1 plus KL are not expanded in $^\Delta$-cultures. IL-1 plus IL-3 was compared to IL-1 plus KL for effectiveness in stimulating primary and secondary HPP-CFC and LPP-CFC in the $^\Delta$-assay. The $^\Delta$-values were calculated from the average of triplicate CFU-C assays. The data shown represent the results from one experiment. Note that the $^\Delta$-values are on a log scale.

Figure 35:
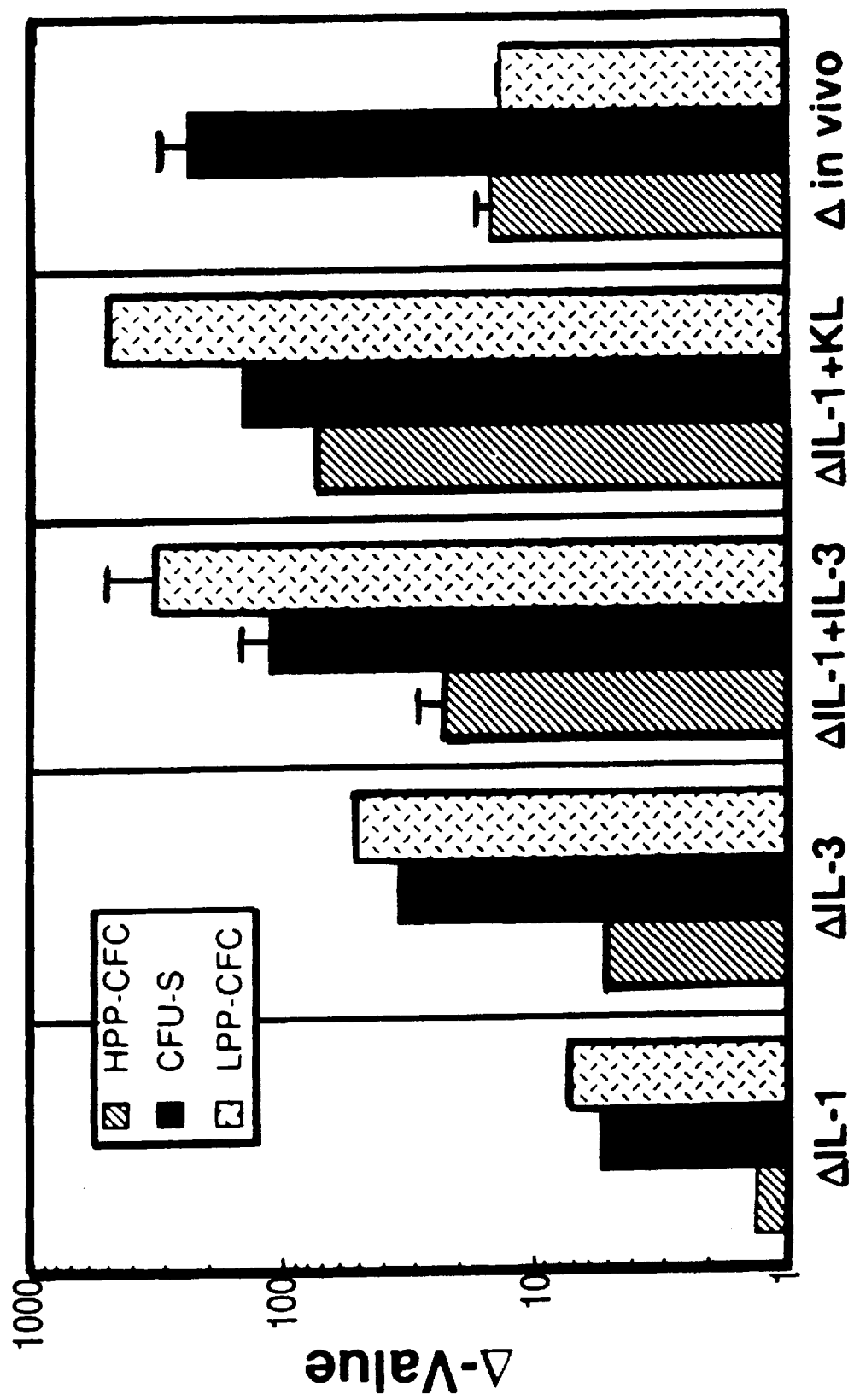

FIG. 35. The numbers CFU-S are expanded in $^\Delta$-cultures. The $^\Delta$-values for the expansion of HPP-CFC, LPP-CFC, and CFU-S that occur in the in vitro $^\Delta$-assay or in vivo after 5-FU administration were compared. The $^\Delta$-values for the in vivo expansion of progenitor cells were measured by dividing the numbers of progenitors per femur observed 8 days after 5-FU administration by the numbers observed 1 day following 5-FU treatment. The data represent the mean plus SE of one to three experiments.

DETAILED DESCRIPTION OF THE INVENTION

The relationship of KL to the c-kit receptor has now been defined, and it is shown that KL is the ligand of c-kit based on binding and cross-linking experiments. N-terminal protein sequence of KL was used to derive KL-specific cDNA clones. These cDNA clones were used to investigate the relationship of the KL gene to the Sl locus, and it was demonstrated that KL is encoded by the Sl locus.

The hematopoietic growth factor KL was recently purified from conditioned medium of BALB/c 3T3 fibroblasts, and it has the biological properties expected of the c-kit ligand (37). KL was purified based on its ability to stimulate the proliferation of BMMC from normal mice but not from W mutant mice in the absence of IL-3. The purified factor stimulates the proliferation of BMMC and CTMC in the absence of IL-3 and therefore appears to play an important role in mature mast cells. In regard to the anticipated function of c-kit in erythropoiesis, KL was shown to facilitate the formation of erythroid bursts (day 7–14 BFU-E) in combination with erythropoietin. The soluble form of KL, which has been isolated from the conditioned medium of Balb/3T3 cells has a molecular mass of 30 kD and a pI of 3.8; it is not a disulfide-linked dimer, although the characteristics of KL upon gel filtration indicate the formation of noncovalently linked dimers under physiological conditions.

The predicted amino acid sequence of KL, deduced from the nucleic acid sequence cDNAs, indicates that KL is synthesized as a transmembrane protein, rather than as a secreted protein. The soluble form of KL then may be generated by proteolytic cleavage of the membrane-associated form of KL. The ligand of the CSF-1 receptor, the closest relative of c-kit, shares the topological characteristics of KL and has been shown to be proteolytically cleaved to produce the soluble growth factor (44, 45). A recent analysis of the presumed structural characteristics of KL, furthermore indicates a relationship of KL and CSF-1 based on amino acid homology, secondary structure and exon arrangements indicating an evolutionary relationship of the two factors and thus strengthening the notion that the two receptor systems evolved from each other (4).

Alternatively spliced KL mRNAs which encode two different forms of the KL protein, i.e., KL-1 and KL-2, have recently been described (15). The KL encoded protein products have been defined and characterized in COS cells transfected with the KL cDNAs and extended the findings of Flanagan et al. in several ways. As noted hereinabove, KL is synthesized as a transmembrane protein which is proteolytically cleaved to produce the soluble form of KL. The protein product of the alternatively spliced transcript of KL, KL-2, which lacks the exon that encodes the presumptive proteolytic cleavage site was shown to display turnover characteristics that are distinct from those of KL-1. In addition, the proteolytic cleavage of both KL-1 and KL-2 can be regulated by agents such as PMA and the calcium ionophore A23187. The relative abundance of KL-1 and KL-2 has been determined in a wide variety of different mouse tissues. This indicates that the expression of KL-1 and KL-2 is controlled in a tissue specific manner.

The gene products of the $Sl^d$ allele have also been defined (15). $Sl^d$ results from a deletion within KL which includes the sequences encoding the transmembrane and cytoplasmic domains of the protein resulting in a biologically active, secreted mutant KL protein. The respective roles of the soluble and cell-associated forms of KL in the proliferative and migratory functions of c-kit are discussed in the light of these results.

This invention provides a purified mammalian protein corresponding to a ligand for the c-kit which comprises a homodimer of two polypeptides, each polypeptide having a molecular weight of about 30 kD and an isoelectric point of about 3.8. As used herein, the term "c-kit ligand" is to mean a polypeptide or protein which has also been defined as stem cell factor, mast cell factor and steel factor. As used herein, c-kit ligand protein and polypeptide encompasses both naturally occurring and recombinant forms, i.e., non-naturally occurring forms of the protein and the polypeptide which are sufficiently identically to naturally occurring c-kit to allow possession of similar biological activity. Examples of such polypeptides includes the polypeptides designated KL-1.4 and S-KL, but are not limited to them. Such protein and polypeptides include derivatives and analogs. In one embodiment of this invention, the purified mammalian protein is a murine protein. In another embodiment of this invention, the purified mammalian protein is a human protein.

Also provided by this invention is a purified mammalian protein corresponding to a c-kit ligand, wherein the purified protein is glycosolated. However, this invention also encompasses unglycosylated forms of the protein. This invention also encompasses purified mammalian proteins containing glycosolation sufficiently similar to that of naturally occurring purified mammalian protein corresponding to c-kit ligand. This protein may be produced by the introduction of a cysteine cross-link between the two homodimer polypeptides described hereinabove by methods known to those of skill in the art.

Also provided by this invention is a pharmaceutical composition which comprises an effective amount of the purified mammalian protein corresponding to c-kit ligand described hereinabove and a pharmaceutically acceptable carrier.

Further provided is a pharmaceutical composition for the treatment of leucopenia in a mammal comprising an effective amount of the above mentioned pharmaceutical composition and an effective amount of a hemopoietic factor, wherein the factor is selected from the group consisting of G-CSF, GM-CSF and IL-3, effective to treat leucopenia in a mammal.

Also provided by this invention is a pharmaceutical composition for the treatment of anemia in a mammal, which comprises an effective amount of the pharmaceutical composition described hereinabove and an effective amount of EPO (erythropoietin) or IL-3, effective to treat anemia in a mammal. Anemia encompasses, but is not limited to Diamond Black fan anemia and aplastic anemia. However, for the treatment of Black fan anemia and aplastic anemia, a pharmaceutical composition comprising an effective amount of the composition described hereinabove and an effective amount of G-CSF and GM-CSF, effective to treat anemia is preferred. A method of treating anemia in mammals by administering to the mammals the above composition is further provided by this invention. A pharmaceutical composition effective for enhancing bone marrow during transplantation in a mammal which comprises an effective amount of the pharmaceutical composition described hereinabove, and an effective amount of IL-1 or IL-6, effective to enhance engraphment of bone marrow during transplantation in the mammal is also provided. A pharmaceutical composition for enhancing bone marrow recovery in the treatment of radiation, chemical or chemotherapeutic induced bone marrow, aplasia or myelosuppression is provided by this inventions which comprises an effective amount of the pharmaceutical composition described hereinabove and an effective amount of IL-1, effective to enhance bone marrow recovery in the mammal. Also provided by this invention is a pharmaceutical composition for treating acquired immune deficiency syndrome (AIDS) in a patient which comprises an effective amount of the pharmaceutical composition described hereinabove and an effective amount of AZT or G-CSF, effective to treat AIDS in the patient.

A composition for treating nerve damage is provided by this invention which comprises an effective amount of the pharmaceutical composition described hereinabove in an amount effective to treat nerve damage in a mammal.

Also provided is a composition for treating infants exhibiting symptoms of defective lung development which comprises an effective amount of the purified mammalian protein and a pharmaceutically acceptable carrier, effective to treat infants exhibiting symptoms of defective lung development.

Further provided is a composition for the prevention of hair loss in a subject which comprises an effective amount of the purified mammalian protein corresponding to c-kit ligand and a pharmaceutically acceptable carrier, effective to prevent the loss of hair in the subject. Also provided by this invention is a pharmaceutical composition for inhibiting the loss of pigment in a subject's hair which comprises an effective amount of the purified mammalian protein corresponding to c-kit ligand and a pharmaceutically acceptable carrier, effective to inhibit the loss of pigment in the subject's hair.

Methods of treating the above-listed disorders by the administration of the effective composition, in an amount effective to treat that disorder, also is provided.

As used herein, the terms "subject" shall mean, but is not limited to, a mammal, animal, human, mouse or a rat. "Mammal" shall mean, but is not limited to meaning a mouse (murine) or human.

This invention provides an isolated nucleic acid molecule which encodes an amino acid sequence corresponding to a c-kit ligand (KL). Examples of such nucleic acids include, but are not limited to the nucleic acids designated KL 1.4, Kl-1, KL-2 or S-KL. The invention also encompasses nucleic acids molecules which differ from that of the nucleic acid molecule which encode these amino acid sequences, but which produce the same phenotypic effect. These altered, but phenotypically equivalent nucleic acid molecules are referred to as "equivalent nucleic acids". And this invention also encompasses nucleic acid molecules characterized by changes in non-coding regions that do not alter the phenotype of the polypeptide produced therefrom when compared to the nucleic acid molecule described hereinabove. This invention further encompasses nucleic acid molecules which hybridize to the nucleic acid molecule of the subject invention. As used herein, the term "nucleic acid" encompasses RNA as well as single and double-stranded DNA and cDNA. In addition, as used herein, the term "polypeptide" encompasses any naturally occurring allelic variant thereof as well as man-made recombinant forms.

For the purposes of this invention, the c-kit ligand (KL) is a human c-kit ligand (KL) or a murine c-kit ligand (KL).

Also provided by this invention is a vector which comprises the nucleic acid molecule which encodes an amino acid sequence corresponding to a c-kit ligand (KL). This vector may include, but is not limited to a plasmid, viral or cosmid vector.

This invention also provides the isolated nucleic acid molecule of this invention operatively linked to a promoter of RNA transcription, as well as other regulatory sequences. As used herein, the term "operatively linked" means positioned in such a manner that the promoter will direct the transcription of RNA off of the nucleic acid molecule. Examples of such promoters are SP6, T4 and T7. Vectors which contain both a promoter and a cloning site into which an inserted piece of DNA is operatively linked to that promoter are well known in the art. Preferable, these vectors are capable of transcribing RNA in vitro. Examples of such vectors are the pGEM series [Promega Biotec, Madison, Wis.].

A host vector system for the production of the c-kit ligand (KL) polypeptide is further provided by this invention which comprises one of the vectors described hereinabove in a suitable host. For the purposes of this invention, a suitable host may include, but is not limited to an eucaryotic cell, e.g., a mammalian cell, or an insect cell for baculovirus expression. The suitable host may also comprise a bacteria cell such as *E. coli*, or a yeast cell.

To recover the protein when expressed in *E. coli*, *E. coli* cells are transfected with the claimed nucleic acids to express the c-kit ligand protein. The *E. coli* are grown in one (1) liter cultures in two different media, LB or TB and pelleted. Each bacterial pellet is homogenized using two passages through a French pressure cell at 20,000 lb/in$^2$ in 20 ml of breaking buffer (below). After a high speed spin 120 k rpm×20 minutes) the supernatants were transferred into a second tube. The c-kit protein or polypeptide is located in the particulate fraction. This may be solubilized using 6M guanidium-HCI or with 8M urea followed by dialysis or dilution.

Breaking Buffer 50 mM hepes, pH 8.0
20% glycerol
150 mM NaCl
1 mM Mg So$_4$
2 mM DTT
5 mM EGTA
20 µg/ml DNAse I.

A purified soluble c-kit ligand (KL) polypeptide as well as a fragment of the purified soluble c-kit ligand (KL) polypeptide is further provided by this invention.

In one embodiment of this invention, the c-kit ligand polypeptide corresponds to amino acids 1 to 164. In other embodiments of this invention, the c-kit ligand polypeptide corresponds to amino acids 1 to about 148, or fusion polypeptides corresponding to amino acids 1 to about 148 fused to amino acids from about 165 to about 202 or 205, as well as a fusion polypeptide corresponding to amino acids 1 to about 164 fused to amino acids 177 to about amino acid 202 or about amino acid 205.

In another embodiment of this invention, the c-kit ligand polypeptide may comprise a polypeptide corresponding to amino acids 1 to about 164 linked to a biologically active binding site. Such biological active binding sites may comprise, but are not limited to an amino acids corresponding to an attachment site for binding stromal cells, the extracellular matrix, a heparin binding domain, a hemonectin binding site or cell attachment activity. For example, see U.S. Pat. Nos. 4,578,079, 4,614,517 and 4,792,525, issued Mar. 25, 1986; Sep. 30, 1986 and Dec. 20, 1988, respectively.

In one embodiment of this invention, the soluble, c-kit ligand (KL) polypeptide is conjugated to an imageable agent. Imageable agents are well known to those of ordinary skill in the art and may be, but are not limited to radioisotopes, dyes or enzymes such as peroxidase or alkaline phosphate. Suitable radioisotopes include, but are not limited to $^{125}$I, $^{32}$P, and $^{35}$S.

These conjugated polypeptides are useful to detect the presence of cells, in vitro or in vivo, which express the c-kit receptor protein. When the detection is performed in vitro, a sample of the cell or tissue to be tested is contacted with the conjugated polypeptide under suitable conditions such that the conjugated polypeptide binds to c-kit receptor present on the surface of the cell or tissue; then removing the unbound conjugated polypeptide, and detecting the presence of conjugated polypeptide, bound; thereby detecting cells or tissue which express the c-kit receptor protein.

Alternatively, the conjugated polypeptide may be administered to a patient, for example, by intravenous administration. A sufficient amount of the conjugated polypeptide must be administered, and generally such amounts will vary depending upon the size, weight, and other characteristics of the patient. Persons skilled in the art will readily be able to determine such amounts.

Subsequent to administration, the conjugated polypeptide which is bound to any c-kit receptor present on the surface of cells or tissue is detected by intracellular imaging.

In the method of this invention, the intracellular imaging may comprise any of the numerous methods of imaging, thus, the imaging may comprise detecting and visualizing radiation emitted by a radioactive isotope. For example, if the isotope is a radioactive isotope of iodine, e.g., $^{125}$I, the detecting and visualizing of radiation may be effected using a gamma camera to detect gamma radiation emitted by the radioiodine.

In addition, the soluble, c-kit ligand (KL) polypeptide fragment may be conjugated to a therapeutic agent such as toxins, chemotherapeutic agents or radioisotopes. Thus, when administered to a patient in an effective amount, the conjugated molecule acts as a tissue specific delivery system to deliver the therapeutic agent to the cell expressing c-kit receptor.

A method for producing a c-kit ligand (KL) polypeptide is also provided which comprises growing the host vector system described hereinabove under suitable conditions permitting production of the c-kit ligand (KL) polypeptide and recovering the resulting c-kit ligand (KL) polypeptide.

This invention also provides the c-kit ligand (KL) polypeptide produced by this method.

This invention further provides c-kit ligand antagonists. These could be small molecule antagonists found by screening assays on the c-kit receptor. Alternatively, they could be antisense nucleic acid molecules, DNA, RNA based on ribose or other sugar backbone, with thiophosphate, methyl phosphate, methyl phosphonate linkages between the sugars. These antisense molecules would block the translation of c-kit ligand in vivo.

A soluble, mutated c-kit ligand (KL) antagonist is also provided, wherein this mutated polypeptide retains its ability to bind to the c-kit receptor, but that the biological response which is mediated by the binding of a functional ligand to the receptor is destroyed. Thus, these mutated c-kit ligand (KL) polypeptides act as antagonists to the biological function mediated by the ligand to the c-kit receptor by blocking the binding of normal, functioning ligands to the c-kit receptor. The KL antagonist may be prepared by random mutagenesis. A mutated or modified KL molecule that was incapable of dimerizing might be an effective antagonist. KL shows a great deal of homology with M-CSF, which contains several α-helices which are believed to be important for dimerization (102). Site directed mutagenesis in these helical regions could block the ability to dimerize. Alternatively, a mutated KL could form a heterodimer with normal, functioning KL, but the heterodimer would not be able to activate the c-kit receptor. Because the c-kit receptor itself needs to dimerize to be become an active kinase, a soluble, mutated KL that bind to the c-kit receptor yet blocks the receptor dimerization would be an effective antagonist.

A pharmaceutical composition which comprises the c-kit ligand (KL) purified by applicants or produced by applicants' recombinant methods and a pharmaceutically acceptable carrier is further provided. The c-kit ligand may comprise the isolated soluble c-kit ligand of this invention, a fragment thereof, or the soluble, mutated c-kit ligand (KL) polypeptide described hereinabove. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Included in these pharmaceutical carriers would be a nebulized aerosol form.

The KL antagonists described above could be used in a variety of treatments including asthma, allergies, anaphylaxis, allergic asthma, arthritis including rheumatoid arthritis, papillary conjunctivitis, leukemia, melanoma, dermal allergic reactions, scleroderma.

This invention further provides a substance capable of specifically forming a complex with the c-kit ligand protein, the soluble, c-kit ligand (KL) polypeptide, or a fragment thereof, described hereinabove. This invention also provides a substance capable of specifically forming a complex with the c-kit ligand (KL) receptor protein. In one embodiment of this invention, the substance is a monoclonal antibody, e.g., a human monoclonal antibody.

A method of modifying a biological function associated with c-kit cellular activity is provided by this invention. This method comprises contacting a sample of the cell, whose function is to be modified, with an effective amount of a pharmaceutical composition described hereinabove, effective to modify the biological function of the cell. Biological functions which may be modified by the practice of this method include, but are not limited to cell-cell interaction, propagation of a cell that expresses c-kit and in vitro fertilization. This method may be practiced in vitro or in vivo. When the method is practice in vivo, an effective amount of the pharmaceutical composition described hereinabove is administered to a patient in an effective amount, effective to modify the biological function associated with c-kit function.

A further aspect of this invention are ex-vivo methods and compositions containing KL in a suitable carrier for ex-vivo use. These aspects include:

1. a method for enhancing transfection of early hematopoietic progenitor cells with a gene by first contacting early hematopoietic cells with the composition containing KL and a hematopoietic factor and then transfecting the cultured cells of step (a) with the gene.
2. a method of transferring a gene to a mammal which comprises a) contacting early hematopoietic progenitor cells with the composition containing KL b) transfecting the cells of (a) with the gene; and c) administering the transfected cells of (b) to the mammal. In these methods the gene may be antisense RNA or DNA.

Compositions containing KL can be used for expansion of peripheral blood levels ex-vivo and an effective amount of a hematopoietic growth factor or factors. The hematopoietic growth factor IL-1, IL-3, IL-6, G-CSF, GM-CSF or combination thereof are particularly suited (see FIG. 26). A method for the expansion of peripheral blood is also provided.

Methods and compositions containing KL are provided for boosting platelet levels or other cell types (IL-6 seems particularly suited).

This invention further provides a method of modifying a biological function associated with c-kit cellular activity by contacting a cell with KL. The cell may express c-kit or may be a hematopoietic cell or may be involved in vitro fertilization.

This invention also provides a method of stimulating the proliferation of mast cells in a patient which comprises administering to the patient the pharmaceutical composition described hereinabove in an amount which is effective to stimulate the proliferation of the mast cells in the patient. Methods of administration are well known to those of ordinary skill in the art and include, but are not limited to administration orally, intravenously or parenterally. Administration of the composition will be in such a dosage such that the proliferation of mast cells is stimulated. Administration may be effected continuously or intermittently such that the amount of the composition in the patient is effective to stimulate the proliferation of mast cells.

A method of inducing differentiation of mast cells or erythroid progenitors in a patient which comprises administering to the patient the pharmaceutical composition described hereinabove in an amount which is effective to induce differentiation of the mast cells or erythroid progenitors is also provided by this invention. Methods of administration are well known to those of ordinary skill in the art and include, but are not limited to administration orally, intravenously or parenterally. Administration of the composition will be in such a dosage such that the differentiation of mast cells or erythroid progenitors is induced. Administration may be effected continuously or intermittently such that the amount of the composition in the patient is effective to induce the differentiation of mast cells or erythroid progenitors.

This invention further provides a method of boosting or stimulating levels of progenitors cells when using c-kit ligand alone or in combination. Particularly effective combinations were with G-CSF, GM-CSF, IL-1, IL-3, IL-6, IL-7 and MIP1α. The combination KL plus IL-1, IL-3 and IL-6 was maximally effective. However, IL-1, IL-3, IL-6 and GM-CSF were moderately effective alone. Particularly as shown in the growth of high proliferative potential colony forming assay (HPP-CFU) of bone treated with 5-fluorouracil (5-FU). Such combinations can be used in vivo, in vitro and ex-vivo.

This invention also provides a method of facilitating bone marrow transplantation or treating leukemia in a patient which comprises administering to the patient an effective amount of the pharmaceutical composition described hereinabove in an amount which is effective to facilitate bone marrow transplantation or treat leukemia. Methods of administration are well known to those of ordinary skill in the art and include, but are not limited to administration orally, intravenously or parenterally. Administration of the composition will be in such a dosage such that bone marrow transplantation is facilitated or such that leukemia is treated. Administration may be effected continuously or intermittently such that the amount of the composition in the patient is effective. This method is particularly useful in the treatment of acute myelogenous leukemia and modifications of chronic myelogenous leukemia. The c-kit ligand would increase the rate of growth of the white blood cells and thereby make them vulnerable to chemotherapy.

This invention also provides a method of treating melanoma in a patient which comprises administering to the patient an effective amount of a pharmaceutical composition described hereinabove in an amount which is effective to treat melanoma. Methods of administration are well known to those of ordinary skill in the art and include, but are not limited to administration orally, intravenously or parenterally. Administration of the composition will be in such a dosage such that melanoma is treated. Administration may be effected continuously or intermittently such that the amount of the composition in the patient is effective.

The soluble, c-kit ligand (KL) polypeptide may also be mutated such that the biological activity of c-kit is destroyed while retaining its ability to bind to c-kit. Thus, this invention provides a method of treating allergies in a patient which comprises administering to the patient an effective amount of the soluble, mutated c-kit ligand described hereinabove and a pharmaceutically acceptable carrier, in an amount which effective to treat the allergy. Such a composition could be delivered in aerosol form with a nebulizing an aqueous form of the mutated c-kit ligand antagonist. The KL antagonist described hereinabove would also be an effective against allergies, once again in aerosol form.

A topical pharmaceutical composition of the c-kit ligand antagonist would be an effective drug for use with arthritis, rheumatoid arthritis, scleroderma, acute dermal allergic reactions. The c-kit ligand antagonist could also be effective against allergic conjunctivitis, post-allergic tissue damage or as a prophylactic against anaphylactic shock. Because mast cells mediate histamine response, a c-kit antagonist or an antisense molecule complementary to c-kit ligand would be effective in blocking histamine mediated responses including allergies and gastric acid secretion.

The c-kit antagonist would be effective as a treatment of melanoma because melanocytes are very dependent on KL for growth. In a similar manner the KL antagonist could be used against leukemia.

As is well known to those of ordinary skill in the art, the amount of the composition which is effective to treat the allergy will vary with each patient that is treated and with the allergy being treated. Administration may be effected continuously or intermittently such that the amount of the composition in the patient is effective.

Furthermore, this invention provides a method for measuring the biological activity of a c-kit (KL) polypeptide which comprises incubating normal bone-marrow mast cells with a sample of the c-kit (KL) polypeptide which comprises incubating normal bone-marrow mast cells with sample of the c-kit ligand (KL) polypeptide under suitable conditions such that the proliferation of the normal bone-marrow mast cells are induced; incubating doubly mutant bone-marrow mast cells with a sample of the c-kit ligand (KL) polypeptide under suitable conditions; incubating each of the products thereof with $^3$H-thymidine; determining the amount of thymidine incorporated into the DNA of the normal bone-marrow mast cells and the doubly mutant bone marrow mast cells; and comparing the amount of incorporation of thymidine into the normal bone-marrow mast cells against the amount of incorporation of thymidine into doubly mutant bone-marrow mast cells, thereby measuring the biological activity of c-kit ligand (KL) polypeptide.

Throughout this application, references to specific nucleotides in DNA molecules are to nucleotides present on the coding strand of the DNA. The following standard abbreviations are used throughout the specification to indicate specific nucleotides:

C - cytosine      A - adenosine
T - thymidine     G - guanosine
U - uracil

EXPERIMENT NUMBER 1—PURIFICATION OF C-KIT LIGAND

Experimental Materials

Mice and embryo identification

WBB6 +/+ and W/W$^V$, C57B16 W$^V$/+ and WB W/+ mice were obtained from the Jackson Laboratory (Bar Harbor, Me.). Heterozygous W$^{41}$/+ mice were kindly provided by Dr. J. Barker from the Jackson Laboratory and maintained in applicants' colony by brother sister mating. Livers were removed at day 14–15 of gestation from fetuses derived by mating W/+ animals. W/W fetuses were identified by their pale color and small liver size relative to other W/+ and +/+ fetuses in the litter. Their identity was confirmed by analysis of the c-kit protein in mast cells derived from each fetus (38).

Mast cell cultures, preparation of peritoneal mast cell and flow cytometry

Mast cells were grown from bone marrow of adult mice and fetal liver cells of day 14–15 fetuses in RPMI-1640 medium supplemented with 10% fetal calf serum (FCS), conditioned medium from WEHI-3B cells, non-essential amino acids, sodium pyruvate, and 2-mercapto-ethanol (RPMI-Complete (C)) (60). Non-adherent cells were harvested, refed weekly and maintained at a cell density less than $7 \times 10^5$ cells/ml. Mast cell content of cultures was determined weekly by staining cytospin preparations with 1% toluidine blue in methanol. After 4 weeks, cultures routinely contained greater than 95% mast cells and were used from proliferation assays. Peritoneal mast cells were obtained from C57B1/6 mice by lavage of the peritoneal cavity with 7–10 ml of RPMI-C. Mast cells were purified by density gradient centrifugation on 22% Metrizamide (Nycomed, Oslo, Norway) in PBS without $Ca^{++}$ and $Mg^{++}$, essentially as previously described (61). Mast cells were stained with 1% toluidine blue in methanol for 5 minutes and washed for 5 minutes in $H_2O$, and berberine sulfate by standard procedures (62). Mast cells were labeled with c-kit specific rabbit antisera which recognizes extracellular determinants of c-kit as previously described and analyzed on a FACSCAN (Becton Dickinson) (38).

Mast cell proliferation assay

Mast cells were washed three times in RPMI to remove IL-3 and cultured at a concentration of $5 \times 10^4$ c/ml in RPMI-C in a volume of 0.2 ml in 96 well plates with two fold serial dilutions of test samples. Plates were incubated for 24 hours at 37° C., 2.5 $\mu$C of $^3$H-TdR was added per well and incubation was continued for another 6 hours. Cells were harvested on glass fiber filters and thymidine incorporation into DNA was determined.

Preparation of fibroblast conditioned medium

Balb/3T3 cells (1) were grown to confluence in Dulbecco's Modified MEM (DME) supplemented with 10% calf serum (CS), penicillin and streptomycin in roller bottles. Medium was removed and cells washed two times with phosphate buffered saline (PBS). DME without CS was added and conditioned medium was collected after three days. Cells were refed with serum containing medium for one to two days, then washed free of serum, and refed with serum free medium and a second batch of conditioned medium was collected after three days. Conditioned medium (CM) was centrifuged at 2500 rpm for 15 minutes to remove cells, filtered through a 0.45 u filter and frozen at 4° C. The conditioned medium was then concentrated 100–200 fold with a Pellicon ultrafiltration apparatus followed by an Amicon stirred cell, both with membranes having a cut off of 10,000 kD.

Column chromatography

Blue Agarose chromatography (BRL, Gaithersburg, Md.) was performed by using column with a bed volume of 100 ml equilibrated with PBS. 50–80 ml of FCM concentrate was loaded onto the column and after equilibration for one hour the flow through which contained the active material was collected and concentrated to 15–20 ml in dialysis tubing with PEG 8000.

Gel filtration chromatography was performed on a ACA54 Ultrogel (LKB, Rockland, Md.) column (2.6×90 cm) which was equilibrated with PBS and calibrated with molecular weight markers; bovine serum albumin (Mr 68,000), chymotrypsinogen (Mr 25,700), and ribonuclease A (Mr 14,300), all obtained from Pharmacia, Piscataway, N.J. The concentrate from the Blue Agarose column was loaded onto the gel filtration column, the flow rate adjusted to 37.5 ml/hour and 7.5 ml fractions collected.

Anion exchange and reverse-phase HPLC (RP-HPLC)

High performance liquid chromatography was performed using a Waters HPLC system (W600E Powerline controller, 490E programmable multiwavelength detector, and 810 Baseline Workstation, Waters, Bedford, Mass.). Active fractions from gel filtration were dialyzed in 0.05 M Tris-HCl pH 7.8 and loaded onto a Protein-Pak™ DEAE-5PW HPLC column (7.5 mm×7.5 cm, Waters), equilibrated with 0.05 M Tris-HCl pH 7.8. Bound proteins were eluted with a linear gradient from 0 to 0.05 M Tris-HCl pH 7.8. Bound proteins were eluted with a linear gradient from 0 to 0.4M NaCl in 0.02 M Tris-HCl pH 7.8. The flow rate was 1 ml/minute and 2 ml fractions were collected.

RP-HPLC was performed using a semi-preparative and an analytical size $C_{18}$ column from Vydac. For both columns buffer A was 100 mM ammonium acetate pH 6.0, and buffer B was 1-propanol. The biologically active fractions from anion exchange were pooled and loaded onto the semi-preparative $C_{18}$ column. Bound proteins were eluted with a steep gradient of 0%–23% 1-propanol within the first 10 minutes and 23–33% 1-propanol in 70 minutes. The flow rate was adjusted to 2 ml/min and 2 ml fractions were collected. Biologically active fractions were pooled and diluted 1:1 with buffer A and loaded on the analytical $C_{18}$ reverse phase column. Proteins were eluted with a steep gradient from 0%–26% 1-propanol in 10 minutes and then a shallow gradient from 26%–33% 1-propanol in 70 minutes. The flow rate was 1 ml/min and 1 ml fractions were collected. Separation on an analytical C4 reverse phase column was performed with a linear gradient of acetonitrile from 0–80% in aqueous 0.1% TFA.

Isolectric focusing (IEF)

One ml of partially purified KL was supplemented with 20% glycerol (v/v) and 2% ampholine (v/v) at pH 3.5–10 (LKB, Gaithersburg, Md.). A 5 to 60% glycerol density gradient containing 2% ampholine (pH 3.5–10) was loaded onto an IEF column (LKB 8100). The sample was applied onto the isodense region of the gradient, followed by IEF (2000 V, 24 h, 4° C.). Five ml fractions were collected and the pH determined in each fraction. The fractions were dialyzed against RPMI-C and then tested for biological activity.

Erythroid progenitor assays

Adult bone marrow, spleen and day 14 fetal liver cells were plated at $10^5$, $10^6$, and $10^7$ cells/ml, respectively, in Iscove's modified Dulbecco's medium with 1.2% methylcellulose, 30% FCS, 100 uM 2-mercaptoethanol, human recombinant erythropoietin (2 units/ml, Amgen, Thousand Oaks, Calif.) (Iscove, 1978; Nocka and Pelus, 1987). Cultures were incubated for 7 days at 37° C. and hemoglobinized colonies and bursts scored under an inverted microscope. 0.1 mM hemin (Kodak) was added to cultures of bone marrow cells for optimum growth. Purified KL, IL-3 either as WEHI-3 CM (10%, vol/vol) or recombinant murine IL-3 (50 u/ml, Genzyme, Cambridge) was added where indicated.

Experimental Methods

Short term mast cell proliferation assay detects a fibroblast derived activity

In order to identify and measure a fibroblast derived growth factor activity which facilitates the proliferation of normal but not $W/W^V$ mast cells, BMMC were washed free of IL-3 containing medium, incubated with medium containing 20 fold concentrated fibroblast conditioned medium (FCM) or WEHI-3 CM (IL-3) and after 24 hours of incubation $^3$H-thymidine incorporation was determined. The response of BMMC derived from normal +/+ and mutant W/W$^V$ mice to IL-3 was similar (FIG. 1); in contrast, 20 fold concentrated fibroblast conditioned medium facilitated the proliferation of +/+ mast cells, but little proliferation was seen with W/W$^V$ mast cells. Concentrated FCM was also tested for its ability to stimulate the proliferation of other IL-3 dependent cells. The myeloid 32D cells are known to lack c-kit gene products (35). No proliferation of the 32D cells was observed with FCM, although normal proliferation was obtained with WEHI-3 CM (not shown). Taken together these results and the known defects in c-kit for both the W and W$^V$ alleles (38), suggested that FCM activity was dependent on the expression of a functional c-kit protein in mast cells (BMMC) and therefore might be the ligand of the c-kit receptor. In addition the FCM activity was distinct from IL-3. Therefore, normal and W mutant mast cells provide a simple, specific assay system for the purification of the putative c-kit ligand (KL) from fibroblast conditioned medium.

Purification of the mast cell stimulating activity KL

Figure 2A:
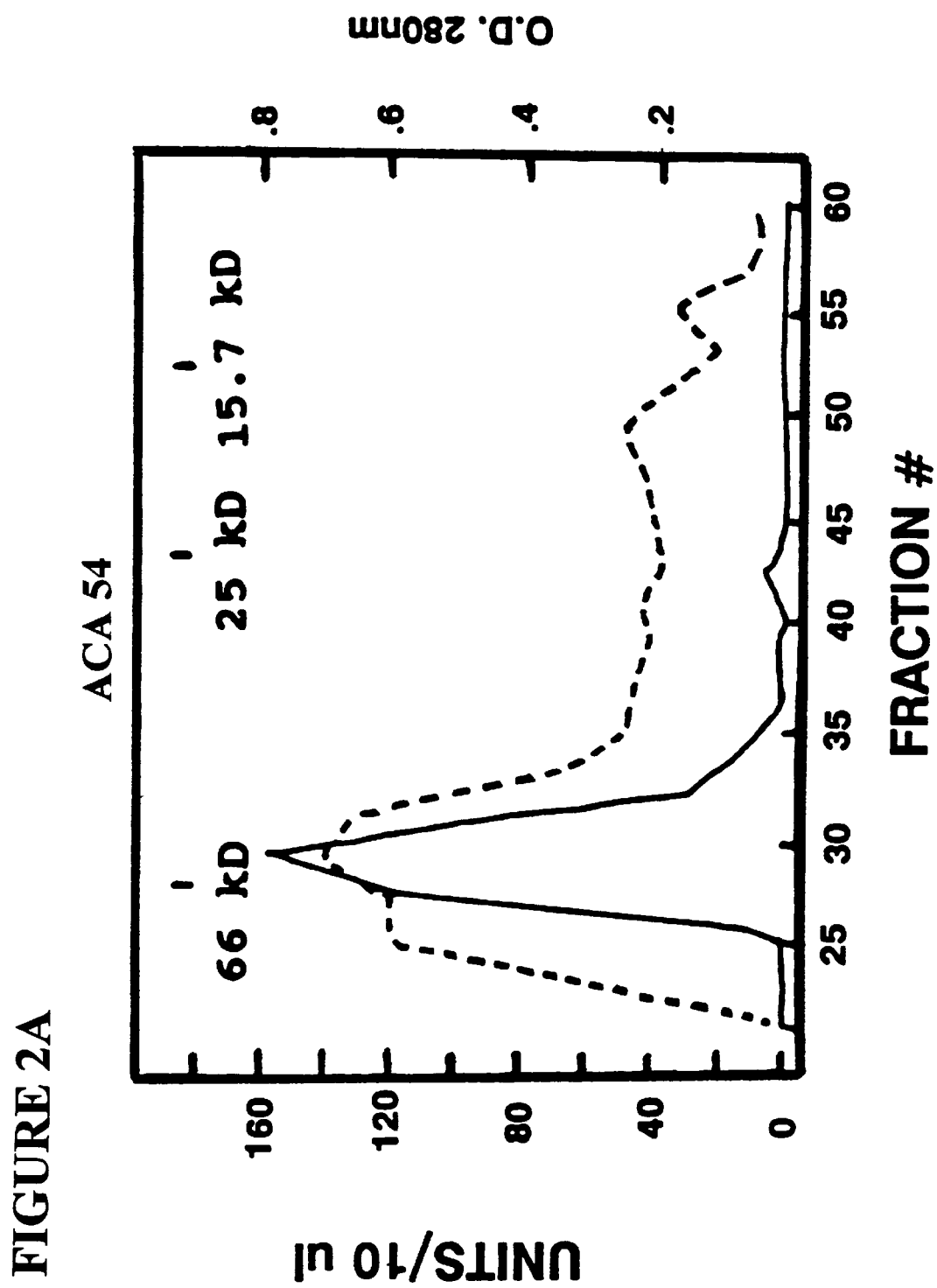
Figure 2B:
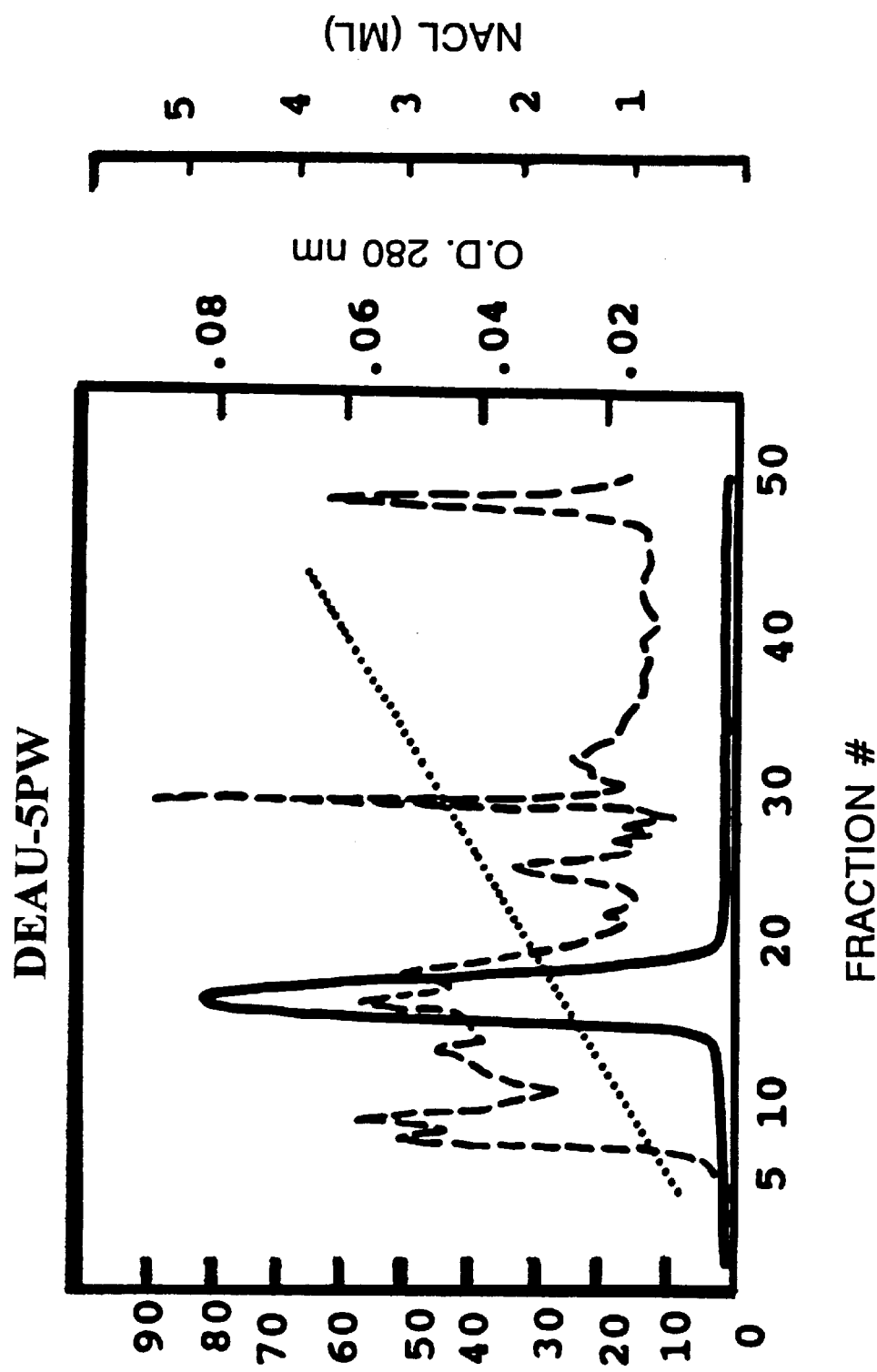
Figure 2D:
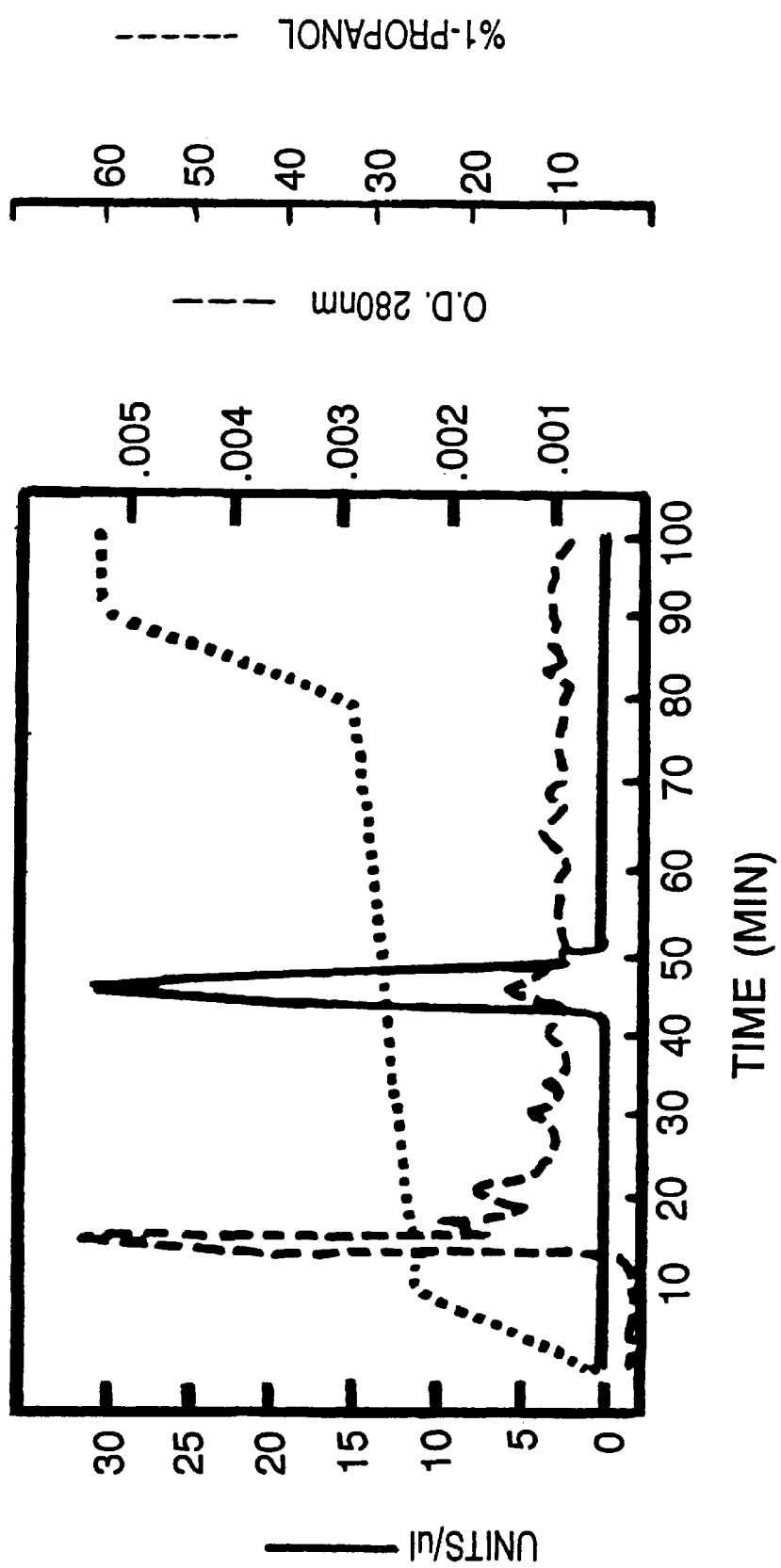
Figure 3C:
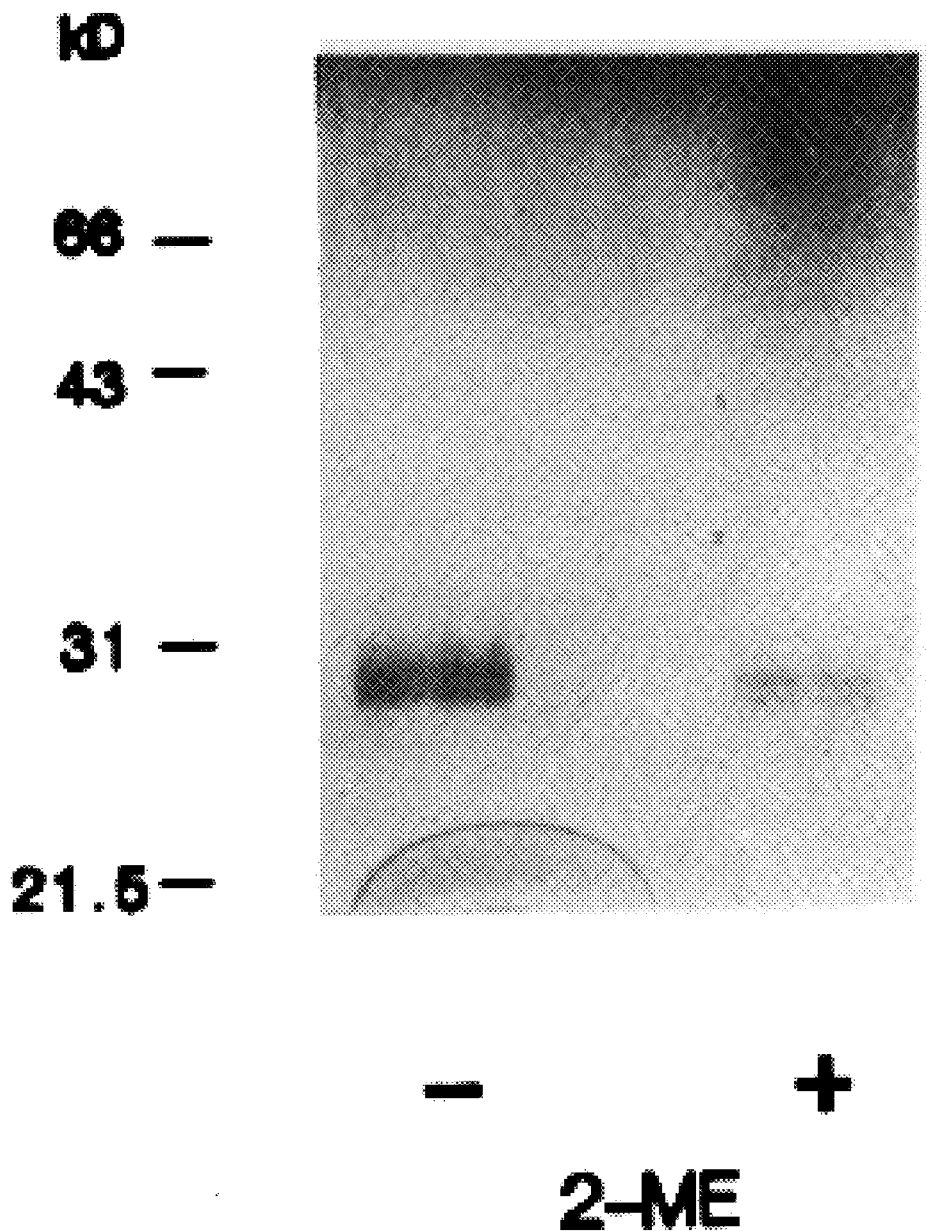

To purify KL, five liters of serum free conditioned medium from Balb/3T3 fibroblasts was concentrated 50 fold by ultrafiltration. The concentrate was passed through a Blue Agarose column equilibrated with PBS and the flow through, which contained the mast cell stimulating activity, was collected and concentrated with polyethylene glycol. In addition to the determination of the bio-activity by using normal mast cells, peak fractions throughout the purification were also tested with W/W$^V$ mast cells where little activity was observed. The material from the Blue Agarose column was fractionated by gel filtration using a ACA 54 column (FIG. 2A). The biological activity eluted as a major and a minor peak corresponding to 55–70 kD and 30 kD, respectively. The fractions of the main peak were pooled, dialyzed and fractionated by FPLC chromatography on a DEAE-5PW column with a NaCl gradient (FIG. 2B). The activity eluted at 0.11 M NaCl from the FPLC column. Peak fractions were pooled and subjected to HPLC chromatography with a semi-preparative C18 column and an ammonium acetate/n-propanol gradient (FIG. 2C). The active material eluted at 30% n-propanol from the semi-preparative C18 column was diluted 1:1 with buffer A and rechromatographed by using an analytical C18 column (FIG. 2D). A single peak of activity eluted again at 30% n-propanol which corresponded to a major peak of absorbance (280 nm) in the eluant profile. Similar results were obtained by using a C4 column with H$_2$O and acetonitrile containing 0.1% TFA as solvents (FIG. 3B). SDS-PAGE analysis of the active fractions from the separations with both solvent systems and silver staining revealed one major band with a mobility corresponding to a molecular mass of 28–30 kD. The presence and magnitude of this band correlated well with the peak of biological activity (FIG. 3). There was no significant difference in the migration of this band under reduced and non-reduced conditions, indicating that KL was not a disulfide linked dimer (FIG. 3C). Three discrete species were observed on both reduced and non-reduced SDS-PAGE indicating size heterogeneity of the purified material. The total amount of protein estimated by absorbance at 280 nm correlated with the amount detected by silver stain relative to BSA as a reference standard. As indicated in Table 1, the purification of KL from conditioned medium of Balb/3T3 cells was more than 3000 fold and the recovery of the initial total activity 47%. Half maximal proliferation of +/+ mast cells in applicants' assay volume of 0.2 ml is defined as 50 units of activity and corresponds to approximately 0.5 ng of protein. Isoelectric focusing of partially purified material (after ion exchange) revealed a major peak of activity in the pH range of 3.7–3.9 indicating an isoelectric point for KL of 3.7–3.9.

TABLE 1

Purification of KL from Balb/3T3 Conditioned Medium

| Purification Step | Total Protein (mg) | Total Activity (U × 10$^{-5}$) | Specific Activity (U/mg) | Purification (Fold) | Yield (%) |
| --- | --- | --- | --- | --- | --- |
| FCM (5L), 50X Concentrated | 152 | — | — | — | — |
| Blue Agarose | 32 | 720 | 2.2 × 10$^4$ | 1 | 100 |
| Gel Filtration | 28 | 480 | 1.7 × 10$^4$ | .77 | 67 |
| DEAE-5PW | 3 | 720 | 2.4 × 10$^5$ | 11 | 100 |
| C18-Semiprep | .079 | 600 | 7.6 × 10$^6$ | 345 | 83 |
| C18-Analytical | .004 | 340 | 8.5 × 10$^7$ | 3863 | 47 |

Proliferative response to KL of mast cells with different c-kit/W mutations

Figure 4B:
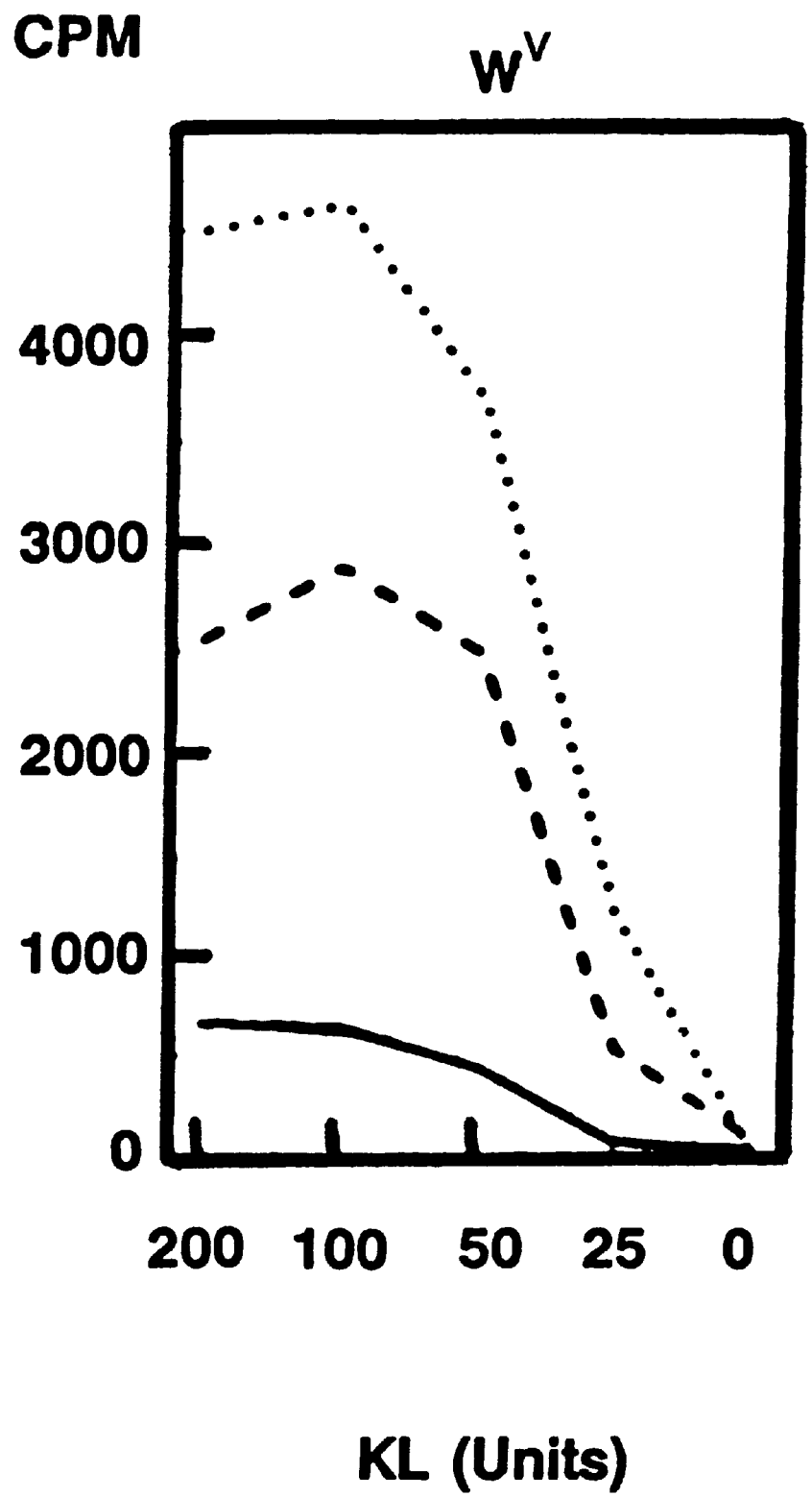
Figure 4C:
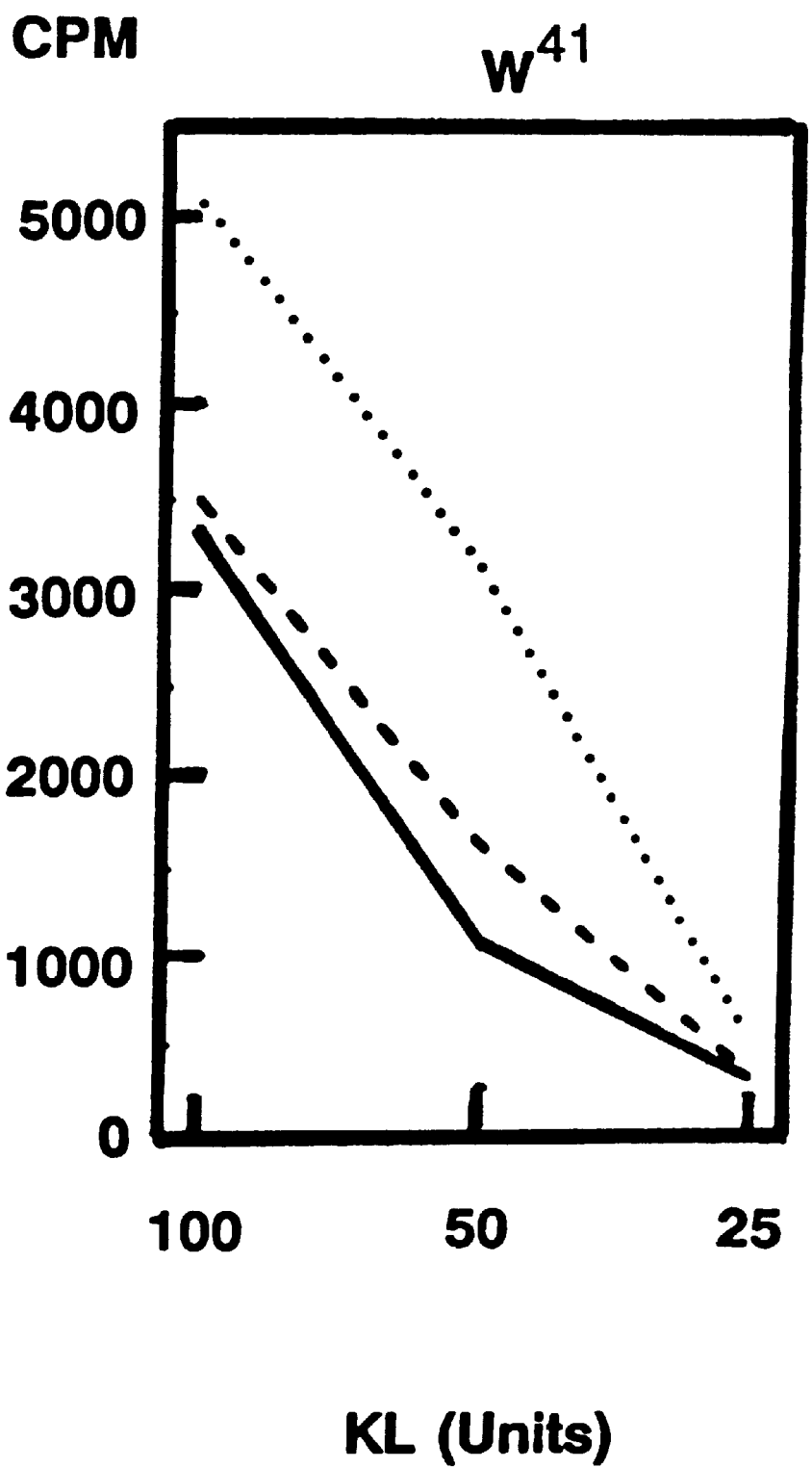

Purified KL was tested for its ability to stimulate the proliferation of mast cells derived from wildtype animals as well as homozygotes and heterozygotes of W, W$^V$, and W$^{41}$ alleles. The original W allele specifies a nonfunctional c-kit receptor and animals homozygous for the W allele die perinatally, are severely anemic and mast cells derived from W/W fetuses do not proliferate when co-cultured with Balb/3T3 fibroblasts (63, 38). The W$^V$ and W$^{41}$ alleles both specify a partially defective c-kit receptor and homozygous mutant animals are viable (64, 65, 38). Homozygous W$^V$ animals have severe macrocytic anemia and their mast cells display a minor response in the co-culture assay, and homozygotes for the less severe W$^{41}$ allele have a moderate anemia and their mast cells show an intermediate response in the co-culture assay. Homozygous and heterozygous mutant and +/+ mast cells were derived from the bone marrow for the W$^V$ and W$^{41}$ alleles and from day 14 fetal livers for the W allele as described previously (38). Fetal liver derived W/W mast cells did not proliferate in response to KL whereas both heterozygous (W/+) and normal (+/+) mast cells displayed a similar proliferative response to KL (FIGS. 4A–4C). Bone marrow derived mast cells from W$^V$/W$^V$ mice were severely defective in their response to KL, although some proliferation, 10% of +/+ values, was observed at 100 U/ml (FIGS. 4A–4C). W$^V$/+ mast cells in contrast to heterozygous W/+ mast cells showed an intermediate response (40%) in agreement with the dominant characteristics of this mutation. W$^{41}$/W$^{41}$ and W$^{41}$/+ mast cells were also defective in their ability to proliferate with KL, although less pronounced than mast carrying the W and the W$^V$ alleles, which is consistent with the in vivo phenotype of this mutation (FIGS. 4A–4C). These results indicate a correlation of the responsiveness of mast carrying the W, W$^V$ and W$^{41}$ alleles to KL with the severity and in vivo characteristics of these mutations. In contrast, the proliferative response of mutant mast cells to WEHI-3CM (IL-3) was not affected by the different W mutations.

KL stimulates the proliferation of peritoneal mast cells

Figure 5A:
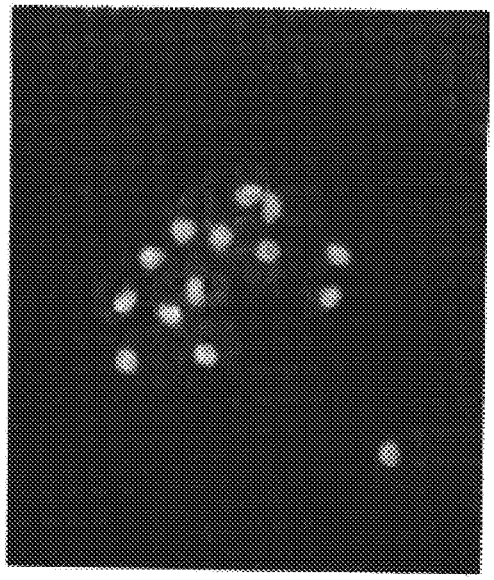
FIGS. 5A–5F. Comparison of c-kit expression and growth factor responsiveness in BMMC and peritoneal mast cells (CTMC/PMC).
  Fluorescent staining of heparin proteoglycans in purified PMC and BMMC by using berberine sulfate.
  Determination of c-kit cell surface expression in PMC and BMMC by FACS using c-kit antibodies. Anti-c-kit serum is indicated by a solid line and non-immune control serum by a dotted line.
  Determination of the proliferation potential of PMC to KL. 5000 cells were plated in 0.5 ml, in the presence of 1000 U/ml of KL, 10% Wehi-3CM or RPMI-C alone and the number of viable cells was determined two weeks later.
Figure 5B:
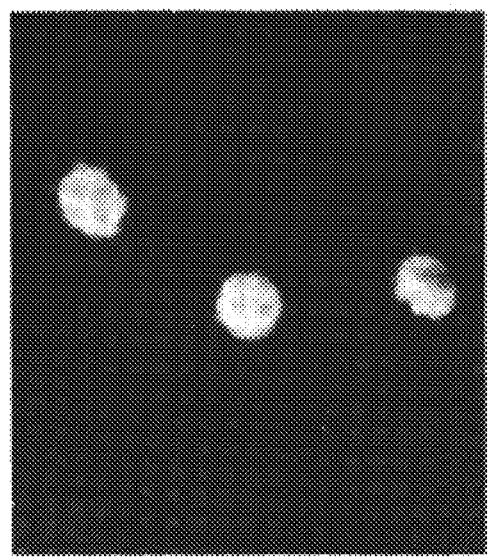
Figure 5C:
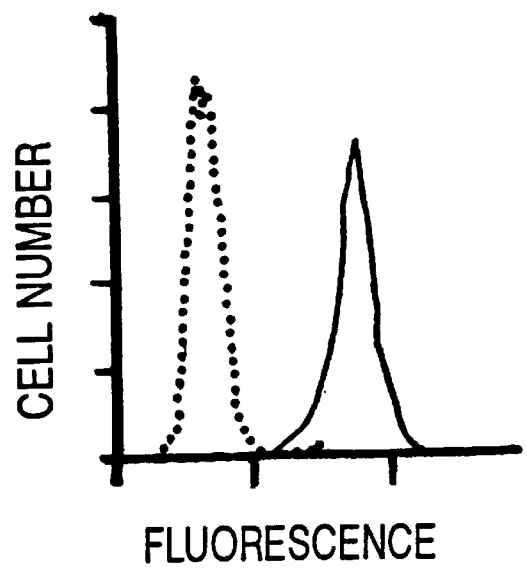
Figure 5D:
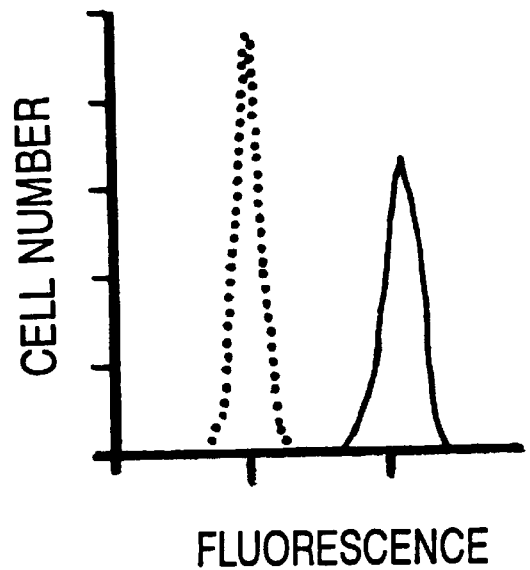
Figure 5E:
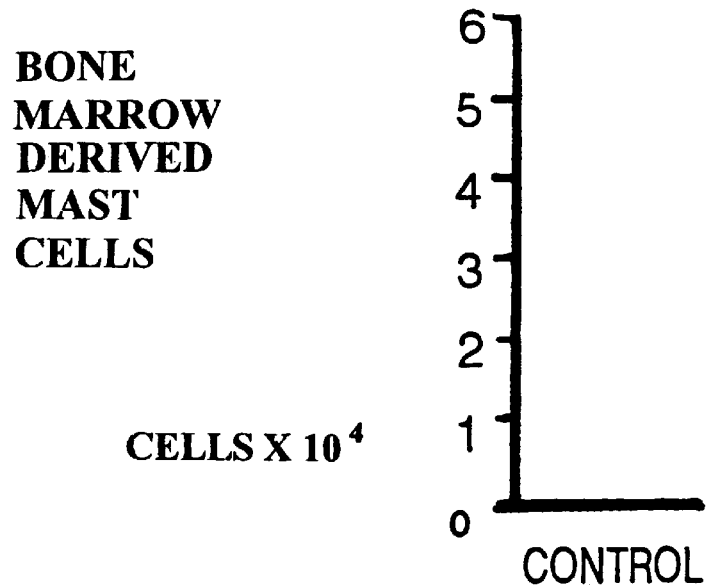
Figure 5F:
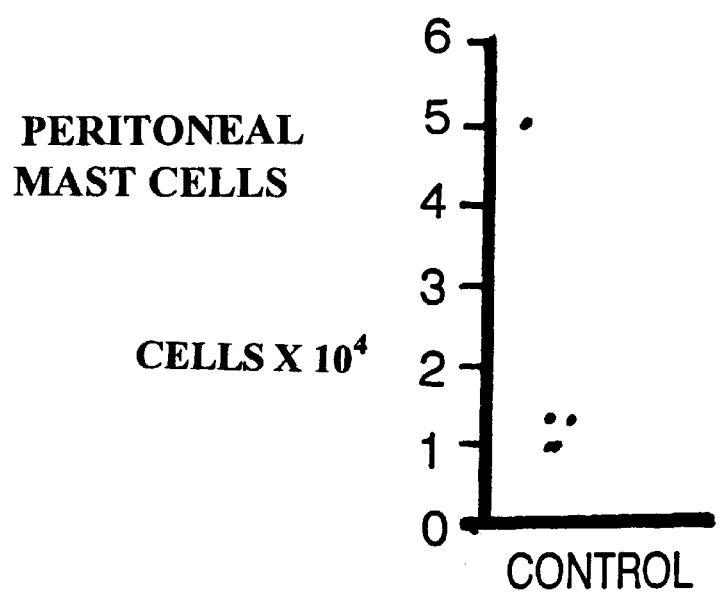

Mast cells of the peritoneal cavity (PMC) have been well characterized and in contrast to BMMC represent connective tissue-type mast cells (66). PMC do not proliferate in response to IL-3 alone; however, their mature phenotype and viability can be maintained by co-culture with NIH/3T3 fibroblasts (67). Thus, it was of interest to determine whether KL could stimulate the proliferation of PMC. First, c-kit was examined to determine if it is expressed in PMC. Peritoneal mast cells were purified by sedimentation in a metrizamide gradient and c-kit expression on the cell surface analyzed by immunofluorescence with anti-c-kit sera or normal rabbit sera. The PMC preparation was 90–98% pure based on staining with toluidine blue and berberine sulfate. Berberine sulfate stains heparin proteoglycans in granules of connective tissue mast cells and in addition the dye is also known to stain DNA (FIGS. 5A–5F) (62). BMMC and mucosal mast cells contain predominantly chondroitin sulfate di-B/E proteoglycans rather than heparin proteoglycans (67); berberine sulfate therefore did not stain the granules in BMMC (FIG. 5A). Analysis of c-kit expression by flow-cytometry indicated that virtually all PMC expressed c-kit at levels similar to those observed in BMMC (FIG. 5B). KL was then examined to determine if it would effect the survival or stimulate the proliferation of PMC (FIG. 5C). Culture of PMC in medium alone, or by the addition of WEHI-3CM at concentrations optimal for BMMC, results in loss of viability of PMC within 3–4 days although a few cells survived in WEHI-3CM for longer periods. Culture of PMC in the presence of KL sustained their viability and after two weeks the cell number had increased from 5000 to 60,000. A similar increase in the number of BMMC was observed in response to KL. In contrast to the lack of a proliferative response of PMC to WEHI-3CM, BMMC's proliferated with WEHI-3CM as expected. After one and two weeks in culture, cells were stained with toluidine blue and berberine sulfate. The mature phenotype of PMC was maintained in culture with 100% of cells staining with both dyes, although the staining with berberine sulfate was somewhat diminished when compared with freshly isolated PMC.

KL stimulates the formation of erythroid bursts (BFU-E)

Figure 6:
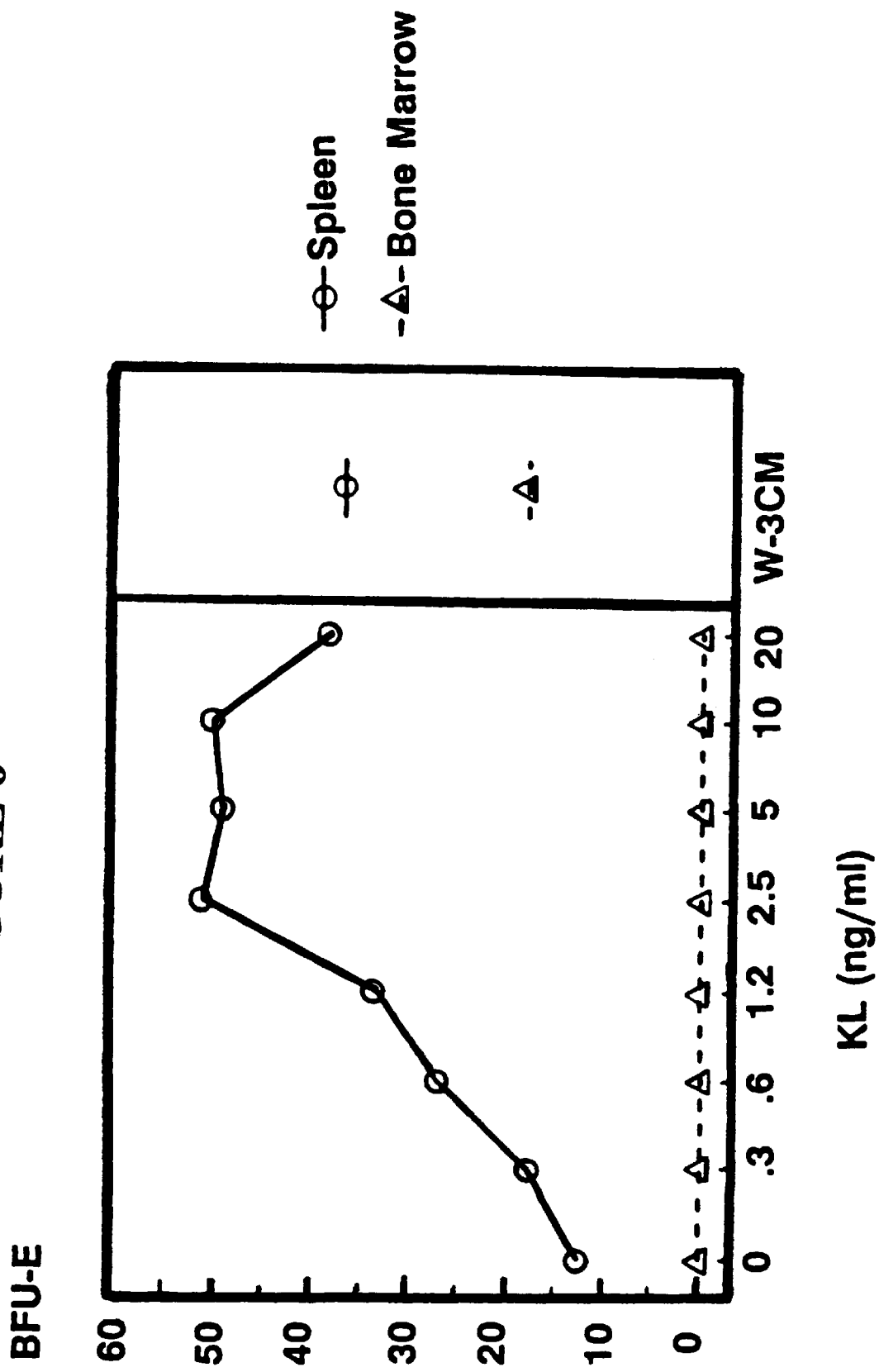
FIG. 6. Determination of burst promoting activity of KL. Bone marrow and spleen cells were plated in the presence of erythropoietin (2U/ml) and pure KL was added at the concentrations shown. The number of BFU-E was determined on day 7 of culture. This data represents the mean of two separate experiments, each with two replicates per concentration of KL.

An important aspect of W mutations is their effect on the erythroid cell lineage. The in vivo consequences of this defect are macrocytic anemia which is lethal for homozygotes of the most severe alleles (47, 65). Analysis of erythroid progenitor populations in the bone marrow of $W/W^V$ mice indicates a slight decrease of BFU-E and CFU-E (68, 69). In livers of W/W fetuses the number of BFU-E is not affected but a large decrease in the number of CFU-E is seen suggesting a role for c-kit at distinct stages of erythroid maturation presumably prior to the CFU-E stage (35). In order to evaluate a role for KL in erythropoiesis and to further define its relationship to the c-kit receptor, the effect of KL on BFU-E formation was determined. Bone marrow, spleen and fetal liver cells were plated, by using standard culture conditions, in the presence and absence of KL, erythropoietin and WEHI-3CM. BFU-E were then scored on day 7 of culture. In the absence of erythropoietin, no erythroid growth was observed with either WEHI-3 CM or KL. In the presence of erythropoietin, BFU-E from spleen cells were stimulated by KL in a dose dependent manner, from 12 BFU-E/$10^6$ cells with erythropoietin alone to 50 BFU-E/$10^6$ cells with maximal stimulation at 2.5 ng of KL/ml (FIG. 6). In addition to the effect on the number of BFU-E, the average size of the bursts was dramatically increased by KL. The number of BFU-E obtained by using spleen cells with KL+erythropoietin was similar to the number observed with WEHI-3 CM+erythropoietin. In contrast, KL+erythropoietin did not stimulate the proliferation of BFU-E from bone marrow cells, whereas WEHI-3 CM+erythropoietin induced the formation of 18 BFU-E from $10^5$ bone marrow cells. The effect of KL on day 14 fetal liver cells was also examined and similar results were observed as with spleen cells. A significant number of BFU-E from fetal liver cells were observed with erythropoietin alone; however, this number increased from 6±2 to 20±5 with 2.5 ng/ml of KL. In the presence of WEHI-3 CM+erythropoietin 18±3 BFU-E were observed with fetal liver cells.

Figure 7:
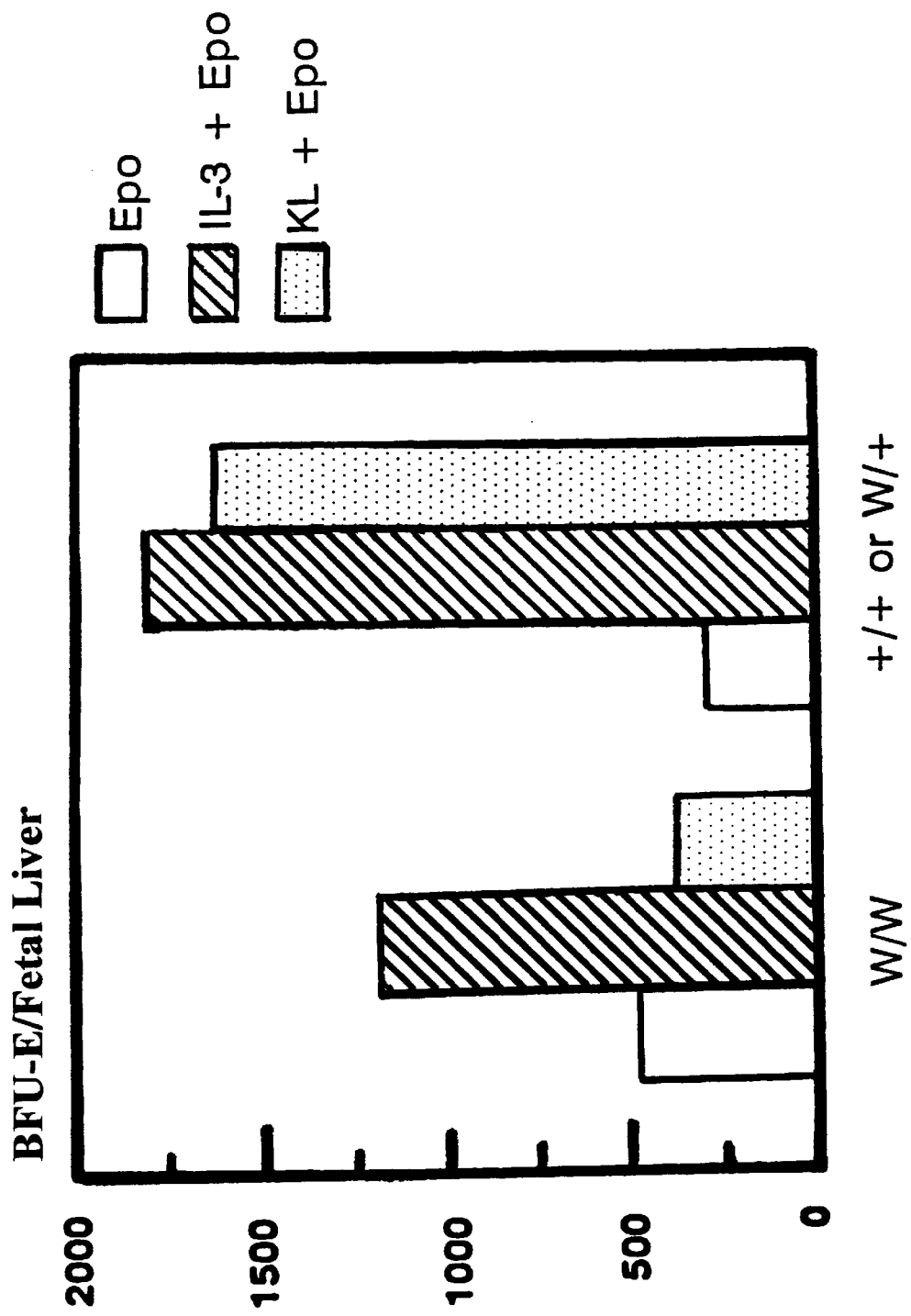
FIG. 7. Determination of KL dependent BFU-E formation from W/W fetal livers. Fetuses from mating W/+ animals were collected at day 16.5 of gestation. One fetus out of four was a W/W homozygote. Liver cells were plated at $10^5$ cells/ml in the presence of either control medium, IL-3 (50 U/ml) or KL (2.5 ng/ml). All cultures contained erythropoietin (2U/ml). Data is expressed as the number of BFU-E/liver and is the mean of 2 replicate plates. The data for +/+ or W/+ fetuses is the mean from the three normal fetuses in the liver.
Figure 9:
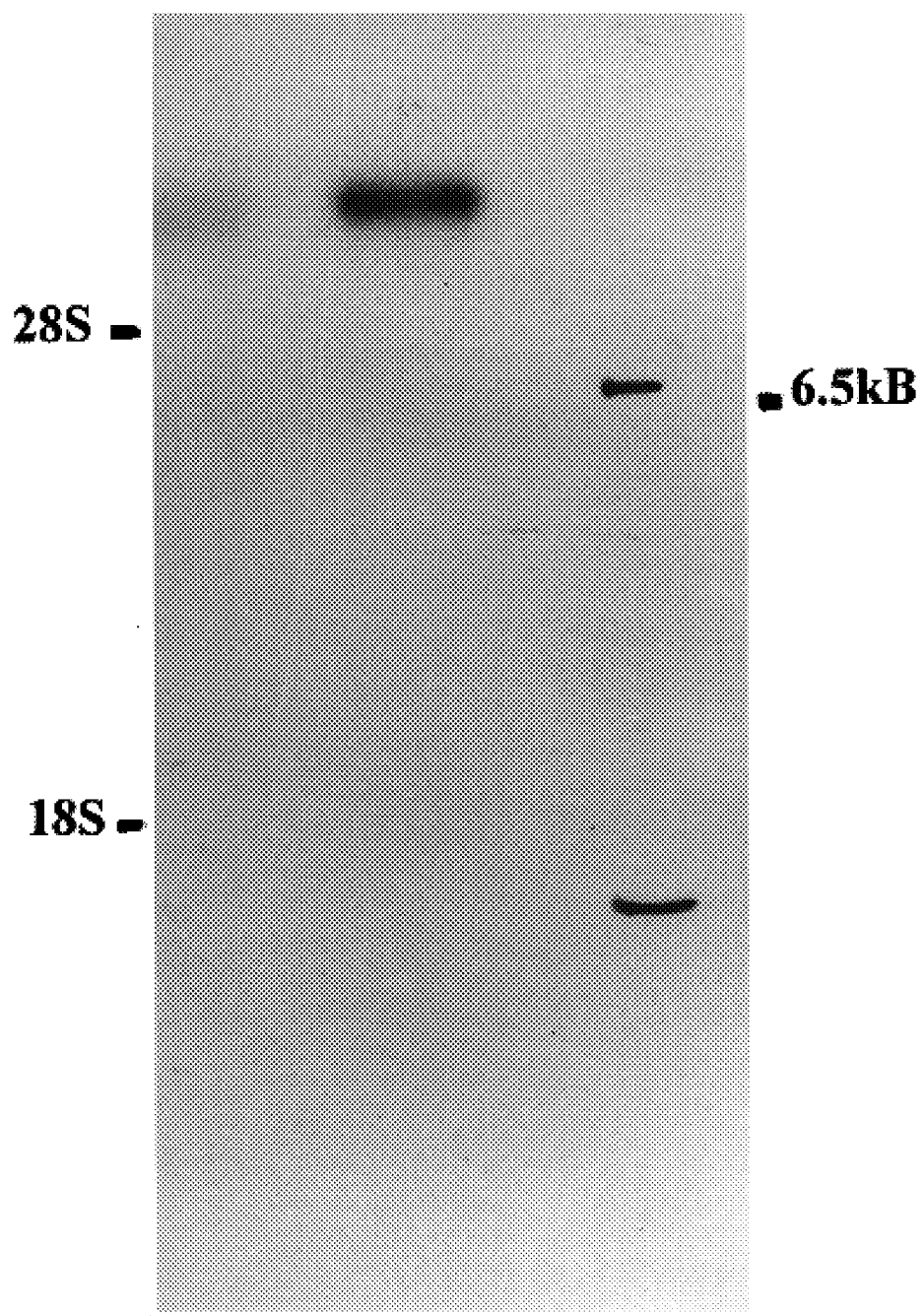
FIG. 9. Northern blot analysis using the PCR generated oligonucleotide probes corresponding to the isolated c-kit ligand polypeptide. A 6.5 kb mRNA was isolated with labelled probes.
Figure 10:
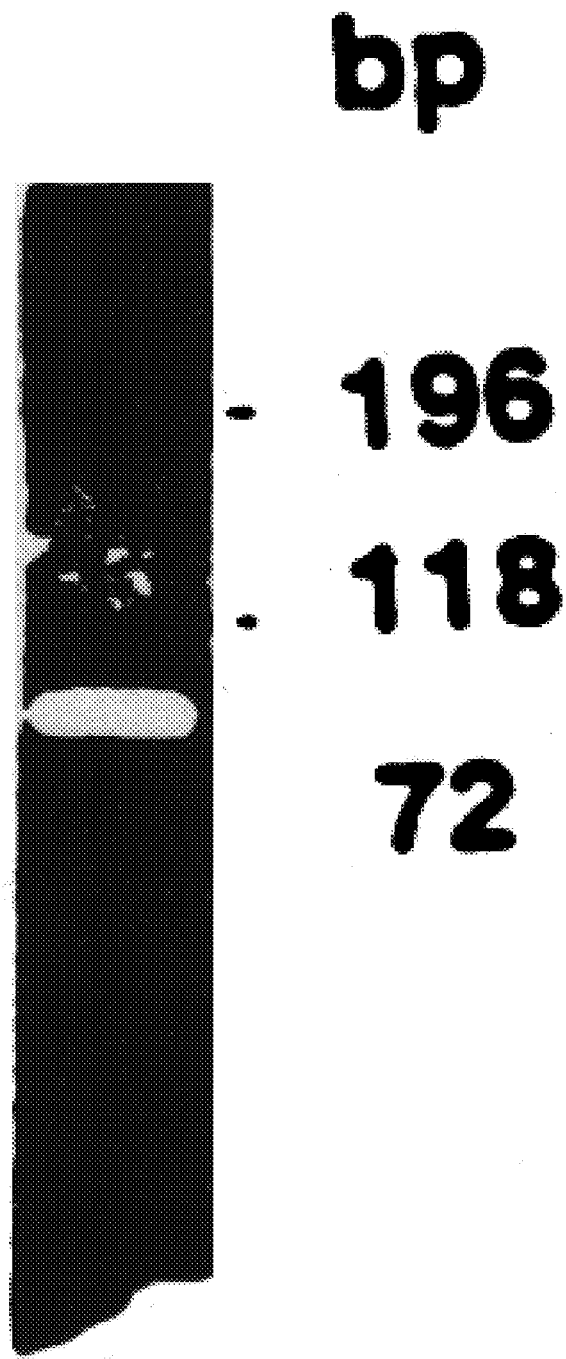
FIG. 10. Derivation of cDNAs corresponding to the N-terminal amino acids 10–36 of KL by RT-PCR. One microgram of poly(A)$^+$RNA from BALB/c 3%3 cells was used as template for cDNA synthesis and subsequent PCR amplification in combination with the two degenerate oligonucleotide primers. Electrophoretic analysis of the 101 bp PCR product in agarose is shown.

To further evaluate the relationship of KL to c-kit in the erythroid lineage, it was assessed whether KL facilitates the formation of erythroid bursts (BFU-E) from fetal liver cells of W/W mice. W/W and W/+ or +/+ liver cells were prepared from fetuses at day 16.5 of gestation from mating w/+ mice. The total number of nucleated cells was reduced eight fold in the liver of the W/W mutant embryo as compared to the healthy fetuses. The number of BFU-E from W/W and W/+ or +/+ fetal liver was similar in cultures grown with IL-3+ erythropoietin and the low level of BFU-E in cultures grown with erythropoietin alone was comparable as well (FIG. 7). KL did not stimulate BFU-E above levels seen with erythropoietin alone for W/W fetal liver cells, whereas as the number of KL dependent BFU-E from W/+ or +/+ liver cells were similar to those obtained with erythropoietin+IL-3. This result suggests that responsiveness of erythroid progenitors to KL is dependent on c-kit function.

Binding studies with purified KL

Purified KL was labelled with $^{125}$I by the chlorine T method to a high specific activity, i.e., to $2.8 \times 10^5$ cpm/ng. Using the labelled KL, specific binding of KL to mast cells was detected. However, with W/W mast cells, no binding was detected and good binding to mast cells of littermates was seen. After binding to mast cells, KL coprecipitated with antisera to c-kit. In addition, binding of KL to W mutant mast cells correlates with c-kit expression on the cell surface, V, 37(+) versus W(−).

Determination of the peptide sequence of the c-kit ligand

The c-kit receptor protein was isolated as described hereinabove and the sequence of the protein was determined by methods well known to those of ordinary skill in the art.

The single letter amino acid sequence of the protein from the N-terminal is:

K E I X G N P V T D N V K D I T K L V A N L P N D Y M I T L N Y V A G M X V L P, with:

K=lysine; E=glutamic acid; I=isoleucine; X=unknown; G=glycine; N=asparagine; P=proline; V=valine; T=threonine; D=aspartic acid; L=leucine; A=alanine; Y=tyrosine; and M=methionine.

Experimental Discussion

The finding that the W locus and the c-kit proto-oncogene are allelic revealed important information about the function of c-kit in developmental processes and in the adult animal. The knowledge of the function of the c-kit receptor in return provided important clues about tissues and cell types which produce the ligand of the c-kit receptor. In an attempt to identify the c-kit ligand, a growth factor was purified, designated KL, from conditioned medium of Balb/3T3 fibroblasts, a cell type suspected to produce the c-kit ligand, which has biological properties expected of the c-kit ligand with regard to mast cell biology and erythropoiesis. KL has a molecular mass of 30 kD and an isoelectric point of 3.8. KL is not a disulfide linked dimer, in contrast to CSF-1, PDGF-A and PDGF-B which have this property (70, 71). Although, the behavior of KL upon gel filtration in PBS indicated a size of 55–70 kD which is consistent with the presence of non-covalently linked dimers under physiological conditions. KL is different from other hematopoietic growth factors with effects on mast cells, such as IL-3 and IL-4, based on its ability to stimulate the proliferation of BMMC and purified peritoneal mast cells (CTMC), but not BMMCs from W mutant mice. Balb/3T3 fibroblasts are a source for the hematopoietic growth factors G-CSF, GM-CSF, CSF-1, LIF and IL-6; however, none of these have the biological activities of KL (35, 71). Furthermore, preliminary results from the determination of the protein sequence of KL indicate that KL is different from the known protein sequences.

An essential role for c-kit and its ligand in the proliferation, differentiation, and/or survival of mast cells in vivo has been inferred because of the absence of mast cells in W mutant mice (72, 73). The precise stage(s) at which c-kit function is required in mast cell differentiation are not known. Mast cells derived in vitro from bone marrow, fetal liver, or spleen with IL-3 resemble mucosal mast cells (MMC), although they may represent a precursor of both types of terminally differentiated mast cells, MMC and CTMC (66). Apparently, c-kit is not required for the generation of BMMC from hematopoietic precursors since IL-3 dependent mast cells can be generated with comparable efficiency from bone marrow or fetal liver of both normal and W mutant mice (60). The demonstration of c-kit expression in BMMC and CTMC/PMC and the corresponding responsiveness of BMMC and mature CTMC/PMC to KL suggests a role for c-kit at multiple stages in mast cell differentiation. In addition to fibroblasts, it has been shown that the combination of IL-3 and IL-4, and IL-3 and PMA, or crosslinking of IgE receptors can stimulate the proliferation of CTMC in vitro (74, 75, 76, 77, 78). In contrast to these biological response modifiers, which are mediators of allergic and inflammatory responses, KL by itself in the presence of FCS is capable of stimulating CTMC proliferation. Therefore, KL may have a mast cell proliferation and differentiation activity which is independent from these immune response for its production and action on target cells.

The defect W mutations exert on erythropoiesis indicates an essential role for c-kit in the maturation of erythroid cells (80, 68, 69). The analysis of erythroid progenitors in fetal livers of W/W fetuses compared with normal littermates suggested that in the absence c-kit function, maturation proceeds normally to the BFU-E stage, but that progression to the CFU-E stage is suppressed (35). In vitro, this defect can be overcome by the inclusion of IL-3 in the culture system, which together with erythropoietin is sufficient to facilitate the maturation of BFU-E from W/W$^V$ and +/+ bone marrow (78). In vivo, a role for IL-3 in this process is not known and therefore c-kit may serve a critical function in the progression through this stage of erythroid differentiation. The ability of KL to stimulate the formation of erythroid bursts from spleen and fetal liver cells together with erythropoietin is consistent with c-kit functioning at this stage of erythroid differentiation. Furthermore, the ability of KL to stimulate W/W BFU-E suggest that c-kit function is required for KL mediated BFU-E formation and this is similar to the requirement of c-kit function for KL mediated mast cell proliferation. A burst promoting effect of Balb/3T3 cells on the differentiation of BFU-E from fetal liver cells had been described previously (79). It is likely that KL is responsible for the burst promoting activity of Balb/3T3 cells. An interesting finding of this study is the inability of KL to stimulate day 7 BFU-E from bone marrow cells. This result suggests that BFU-E in fetal liver, adult spleen and adult bone marrow differ in their growth requirements. Recent experiments indicate that KL may stimulate an earlier erythroid-multipotential precursor in bone marrow which appears at later times in culture (day14–20). To demonstrate a direct effect of KL on BFU-E formation and to rule out the involvement of accessory cells or other endogenous growth factors, experiments with purified progenitor populations need to be performed.

In addition to the defects in erythropoiesis and mast cell development, W mutations are thought to affect the stem cell compartment of the hematopoietic system. The affected populations may include the spleen colony forming units (CFU-S) which produce myeloid colonies in the spleen of lethally irradiated mice as well as cell with long term repopulation potential for the various cell lineages (81, 46, 47, 81, 82). It will now be of interest to determine if there is an effect of KL in the self-renewal or the differentiation potential of hematopoietic stem cell populations, possibly in combination with other hematopoietic growth factors, in order to identify the stage(s) where the c-kit/W gene product functions in the stem cell compartment.

Mutations at the steel locus (S1) of the mouse produce pleiotropic phenotypes in hematopoiesis, melanogenesis and gametogenesis similar to those of mice carrying W mutations (47, 51). However, in contrast to W mutations, S1 mutations affect the microenvironment of the cellular target of the mutation and are not cell autonomous (46). Because of the parallel and complementary effects of the W and the S1 mutations, it has been suggested that the S1 gene encode the ligand of the c-kit receptor or a gene product that is intimately linked to the production and/or function of this ligand (9). In agreement with this conjecture S1/S1$^d$ embryo fibroblasts or conditioned medium from S1/S1$^d$ fibroblasts fail to support the proliferation of BMMC and mast cell progenitors, respectively, and presumably do not produce functional KL (16, 84). If KL is the ligand of the c-kit receptor, then molecular analysis will enable the determination of the identity of KL with the gene product of the S1 locus; in addition, one would predict that administration of KL to mice carrying S1 mutations would lead to the cure of at least some symptoms of this mutation.

The 1.4 kb cDNA clone is used to screen a human fibroblast or a human placenta library using the methods disclosed hereinabove. Upon isolating the gene which encodes the human c-kit ligand, the gene will be characterized using the methods disclosed hereinabove.

EXPERIMENT NUMBER 2

ISOLATION OF THE NUCLEIC ACID SEQUENCE

Experimental Materials

Mice and tissue culture

WBB6+/+, C57BL/6J, C57BL/67 W$^v$/+, WB6W/t, C3HeB/FeJ a/a Ca$^J$ S1 Hm, and M. spretus mice were obtained from The Jackson Laboratory (Bar Harbor, Me.). For the interspecific cross, female C57B1/6J and male M. spretus mice were mated; progeny of this cross were scored for inheritance of C57BL/6J or M. spretus alleles as described infra. (C57BL/6J×M. spretus) F1 female offspring were backcrossed with C57BL/6J males.

Mast cells were grown from the bone marrow of adult +/+, W$^v$/W$^v$ and W/+ mice and W/W fetal liver of day 14–15 fetuses in RPMI 1640 medium supplemented with 10% fetal cell serum (FCS), conditioned medium from WEHI-3B cells, nonessential amino acids, sodium pyruvate, and 2-mercaptoethanol (RPMI-Complete) (36, 60). BALB/c 3T3 cells (1) were obtained from Paul O'Donnell (Sloan-Kettering Institute, New York, N.Y.) and were grown in Dulbecco's modified MEM supplemented with 10% calf serum, penicillin, and streptomycin.

Purification and amino acid sequence determination of KL

KL was purified from conditioned medium of BALB/c 3T3 cells by using a mast cell proliferation assay as described elsewhere (37). Conditioned medium was then concentrated 100- to 200-fold with a Pellicon ultrafiltration apparatus followed by an Amicon stirred cell. The concentrate was then chromatographed on Blue Agarose (Bethesda Research Laboratories, Gaithersburg, Md.), and the flow-through, which contained the active material, was concentrated in dialysis tubing with polyethylene glycol 8000 and then fractionated by gel filtration chromatography on an ACA54 Ultrogel (LKB, Rockland, Md.) column. The biological activity eluted as a major and a minor peak, corresponding to 55–70 kd and 30 kd, respectively. The fractions of the main peak were pooled, dialyzed, and fractionated by FPLC on a DEAE-5PW column with an NaCl gradient. The activity eluted at 0.11 M NaCl from the FPLC column. Peak fractions were pooled and subjected to HPLC with a semipreparative C18 column and an ammonium acetate-n-propanol gradient. The active material eluted at 30% n-propanol from the semipreparative C18 column was diluted 1:1 and re-chromatographed by using an analytical C18 column. A single peak of activity eluted again at 30% n-propanol, which corresponds to a major peak of absorbance (280 nm) in the eluant profile. Similar results were obtained by using a C4 column with $H_2O$ and acetonitrile containing 0.1% TFA as solvents. N-terminal amino acid sequence was determined on an Applied Biosystems 477A on-line PTH amino acid analyzer (Hewick et al., 1961).

Iodination

KL was iodinated with chloramine T with modifications of the method of Stanley and Gilbert (1981). Briefly, the labeling reaction contained 200 ng of KL, 2 nmol of chloramine T, 10% dimethyl sulfoxide, and 0.02% polyethylene glycol 8000, in a total volume of 25 µl in 0.25 M phosphate buffer (pH 6.5). The reaction was carried out for 2 min. at 4° C. and stopped by the addition of 2 nmol of cysteine and 4 µM KI. KL was then separated from free NaI by gel filtration on a PD10 column (Pharmacia). Iodinated KL was stored for up to 2 weeks at 4° C.

Binding assay

Binding buffer contained RPMI 1640 medium, 5% BSA (Sigma), 20 mM HEPES (pH 7.5) and $NaN_3$. Binding experiments with nonadherent cells were carried out in 96-well tissue culture dishes with $2\times10^5$ cells per well in a volume of 100 µl. Binding experiments with #2 cells were carried out in 24-well dishes in a volume of 300 µl. Cells were equilibrated in binding buffer 15 minutes prior to the addition of competitor or labeled KL. To determine nonspecific binding, unlabeled KL or anti-c-kit rabbit serum was added in a 10-fold excess 30 minutes prior to the addition of $^{125}$I-KL. Cells were incubated with $^{125}$I-KL for 90 minutes, and nonadherent cells were pelleted through 150 µl of FCS. Cell pellets were frozen and counted.

Immunoprecipation and cross-linking

BMMC were incubated with $^{125}$I-KL under standard binding conditions and washed in FCS and then in PBS at 4° C. Cells were lysed as previously described (35) in 1% Triton X-100, 20 mM Tris (pH 7.4), 150 mM NaCl, 20 mM EDTA, 10% glycerol, and protease inhibitors phenylmethylsufonyl fluoride (1 mM) and leupeptin (20 µg/ml). Lysates were immunoprecipitated with normal rabbit serum, or c-kit specific sera raised by immunization of rabbits with a fragment of the v-kit tyrosine kinase domain (23); or the murine c-kit expressed from a cDNA in a recombinant vaccinia virus (36). For coprecipitation experiments, immunoprecipitates were washed three times with wash A (0.1% Triton X-100, 20 mM Tris [pH 7.4], 150 mM NaCl, 10% glycerol), solubilized in SDS sample buffer, and analyzed by SDS-PAGE and autoradiography. For cross-linking experiments, cells were incubated with disuccinimidyl substrate (0.25 mg/ml) in PBS for 30 minutes at 4° C., washed in PBS, and lysed as described above. Washing conditions following precipitation were as follows: one time in wash B (50 mM Tris, 500 mM NaCl, 5 mM EDTA, 0.2% Triton X-100), three times in wash C (50 mM Tris, 150 mM NaCl, 0.1% Triton X-100, 0.1% SDS, 5 mM EDTA), and one time in wash D (10 mM Tris, 0.1% Triton X-100).

cDNA synthesis, PCR amplification (RT-PCR), and sequence determination

The RT-PCR amplification was carried out essentially as described (53). For cDNA synthesis, 1 µg of poly(A)$^-$ RNA from confluent BALB/c 3T3 cells in 25 µl of 0.05 M Tris-HCl (pH 8.3), 0.075 M KCl, 3 mM $MgCl_2$, 10 mM dithiothreitol, 200 µM dNTPs and 25 U of RNAsin (Promega) was incubated with 50 pmol of antisense primer and 50 U of Moloney murine leukemia virus reverse transcriptase at 40° C. for 30 minutes. Another 50 U of reverse transcriptase was added, and incubation was continued for another 30 minutes. The cDNA was amplified by bringing up the reaction volume to 50 µl with 25 µl of 50 mM KCl, 10 mM Tris-HCl (pH 8.3), 1.5 mM $MgCl_2$, 0.01% (w/v) gelatin, and 200 µM dNTPs, adding 50 pmol of sense primer and 2.5 U or Taq DNA polymerase, and amplifying for 25–30 cycles in an automated thermal cycler (Perkin-Elmer Cetus). The amplified fragments were purified by agarose gel electrophoresis, digested with the appropriate restriction enzymes, and subcloned into M13mp18 and M13mp19 for sequence analysis (49).

cDNA isolation and sequencing

A mouse 3T3 fibroblast lambda g11 cDNA library obtained from Clontech was used in this work. Screening in duplicate was done with *Escherichia coli* Y1090 as a host bacterium (48); 5' end-labeled oligonucleotide was used as a probe. Hybridization was in 6X SSC at 63° C., and the final wash of the filters was in 2X SSC, 0.2% SDS at 63° C. Recombinant phage were digested with EcoRI and the inserts subcloned into M13 for sequence analysis. The nucleotide sequence of these cDNAs was determined, on both strands and with overlaps, by the dideoxy chain termination method of Sanger et al. (49) by using synthetic oligodeoxynucleotides (17-mers) as primers.

DNA and RNA analysis

Genomic DNA was prepared from tail fragments, digested with restriction enzymes, electrophoretically fractionated, and transferred to nylon membranes. For hybridization, the 1.4 kb KL cDNA and TIS Dra/SaI (a probe derived from the transgene insertion site in the transgenic line TG.EB (85) were used as probes.

BALB/c 3T3 cells were homogenized in guanidinium isothiocyanate, and RNA was isolated according the method of Chirgwin et al. (10). Total cellular RNA (10 µg) and poly(A)$^+$ RNA were fractionated in 1% agarose-formaldehyde gels and transferred to nylon membranes (Nytran, Schleicher & Schuell); prehybridization and hybridization were performed as previously described (86, 35). The 1.4 kb KL cDNA labeled with [$^{32}$P]phosphate was used as a probe for hybridization (87).

Preparation of c-kit and c-kit ligand monoclonal antibodies

For the isolation of human monoclonal antibodies, eight week old Balb/c mice are injected intraperitoneally with 50 micrograms of a purified human soluble c-kit ligand (KL) polypeptide, or a soluble fragment thereof, of the present invention (prepared as described above) in complete Freund's adjuvant, 1:1 by volume. Mice are then boosted, at monthly intervals, with the soluble ligand polypeptide or soluble ligand polypeptide fragment, mixed with incomplete Freund's adjuvant, and bled through the tail vein. On days 4, 3, and 2 prior to fusion, mice are boosted intravenously with 50 micrograms of polypeptide or fragment in saline. Splenocytes are then fused with non-secreting myeloma cells according to procedures which have been described and are known in the art to which this invention pertains. Two weeks later, hybridoma supernatants are screened for binding activity against c-kit receptor protein as described hereinabove. Positive clones are then isolated and propagated.

Alternatively, to produce the monoclonal antibodies against the c-kit receptor, the above method is followed except that the method is followed with the injection and boosting of the mice with c-kit receptor protein.

Alternatively, for the isolation of murine monoclonal antibodies, Sprague-Dawley rats or Louis rats are injected with murine derived polypeptide and the resulting splenocydes are fused to rat myeloma (y3AG 1.2.3) cells.

Experimental Results

Isolation and characterization of murine cDNAs encoding the hematopoietic growth factor KL The KL protein was purified from conditioned medium from BALB/c 3T3 cells by a series of chromatographic steps including anion exchange and reverse-phase HPLC as described hereinabove (37). As previously noted, the sequence of the N-terminal 40 amino acids of KL was determined to be:

K E I X G N P V T D N V K D I T K L V A N L P N D Y M I T L N Y V A G M X V L P (SEQ ID NO:10).

To derive a nondegenerate homologous hybridization probe, fully degenerate oligonucleotide primers corresponding to amino acids 10–16 (sense primer) and 31–36 (antisense primer) provided with endonuclease recognition sequences at their 5' ends were synthesized as indicated in FIG. 8. A cDNA corresponding to the KL mRNA sequences that specify amino acids 10–36 of KL was obtained by using the reverse transcriptase modification of the polymerase chain reaction (RT-PCR). Poly (A)$^+$ RNA from BALB/c 3T3 cells was used as template for cDNA synthesis and PCR amplification in combination with the degenerate oligonucleotide primers.

Figure 11D:
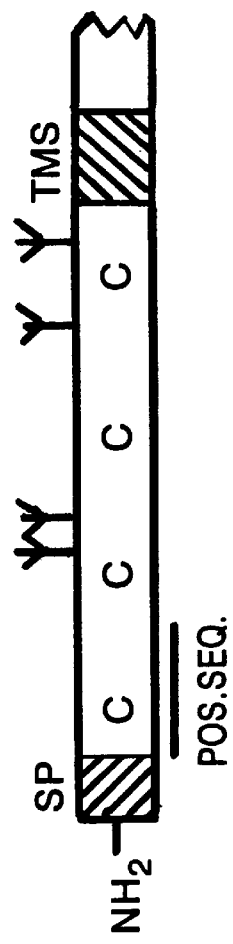
FIG. 11. Nucleotide Sequence and Predicted Amino Acid Sequence of the 1.4 kb KL cDNA clone. The predicted amino acid sequence of the long open reading frame is shown above and the nucleotide sequence using the single-letter amino acid code. The numbers at right refer to amino acids, with methionine (nucleotides 16–18) being number 1. The potential N-terminal signal sequence (SP) and the transmembrane domain (TMS) are indicated with dashed lines above the sequence, and cysteine residues in the extracellular domain are circled. A schematic of the predicted protein structure is indicated below. N-linked glycosylation sites and the location of the N-terminal peptide sequence (Pep. Seq.) are indicated. The nucleic acid sequence is also identified as SEQ ID:NO:1.

The amplified DNA fragment was subcloned into M13, and the sequences for three inserts were determined. The sequence in between the primers was found to be unique and to specify the correct amino acid sequence (FIG. 8). An oligonucleotide (49 nucleotides) corresponding to the unique sequence of the PCR products was then used to screen a λ gt11 mouse fibroblast library. A 1.4 kb clone was obtained that, in its 3' half, specifies an open reading frame that extends to the 3' end of the clone and encodes 270 amino acids (FIG. 11). The first 25 amino acids of the KL amino acid sequence have the characteristics of a signal sequence. The N-terminal peptide sequence that had been derived from the purified protein (amino acids 26–65) follows the signal sequence. A hydrophobic sequences of 21 amino acids (residues 217–237) followed at its carboxyl end by positively charged amino acids has the features of a transmembrane segment. In the sequence between the signal peptide and the transmembrane domain, four potential N-linked glycosylation sites and four irregularly spaced cysteines are found. A C-terminal segment of 33 amino acids follows the transmembrane segment without reaching a termination signal (end of clone). The KL amino acid sequence therefore has the features of a transmembrane protein: an N-terminal signal peptide, an extracellular domain, a transmembrane domain, and a C-terminal intracellular segment.

Figure 12:
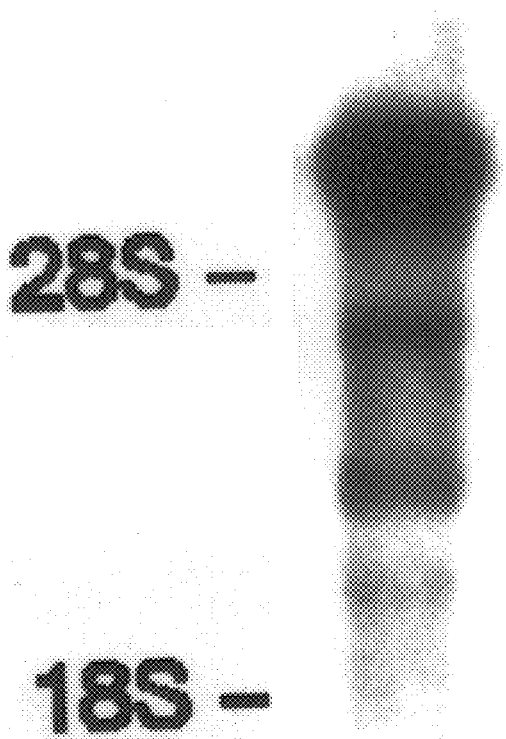
FIG. 12. Identification of KL-Specific RNA Transcripts in BALB/c 3T3 Cell RNA by Northern Blot Analysis. Poly(A)$^+$ RNA (4 $\mu$g) from BALB/c 3T3 cells was electrophoretically separated, transferred to nitrocellulose, and hybridized with $^{32}$P. labeled 1.4 kb KL cDNA. The migration of 18S and 28S ribosomal RNSs is indicated.

RNA blot analysis was performed to identify KL-specific RNA transcripts in BALB/c 3T3 cells (FIG. 12). A major transcript of 6.5 kb and two minor transcripts of 4.6 and 3.5 kb were identified on a blot containing poly(A)$^+$ RNA by using the 1.4 kb KL cDNA as a probe. Identical transcripts were detected by using an end-labeled oligonucleotide derived from the N-terminal protein sequence. This result then indicates that KL is encoded by a large mRNA that is abundantly expressed in BALB/c 3T3 cells.

The soluble form of KL is a ligand of the c-kit receptor

Figure 13A:
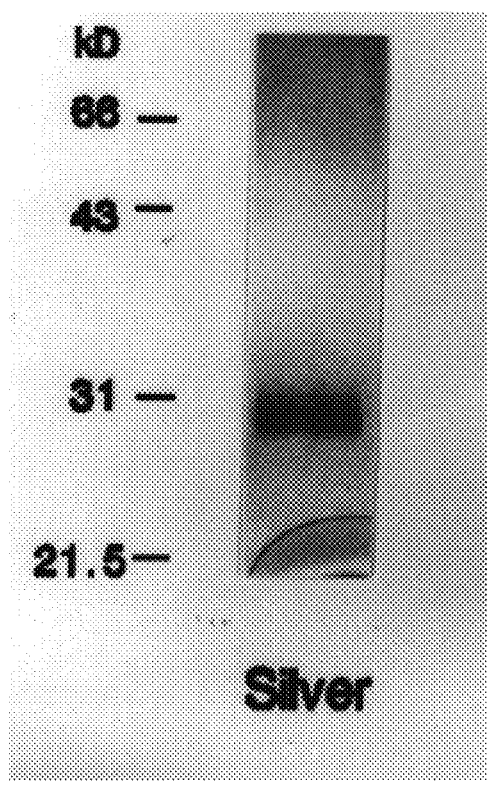
FIGS. 13A–13B. SDS-PAGE Analysis of KL.
 A. Silver staining of KL.
 B. Autoradiography of $^{125I}$-KL.
Figure 13B:
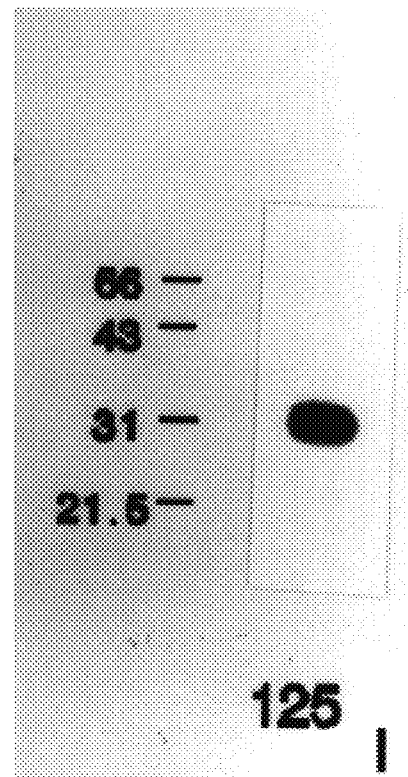
Figure 14A:
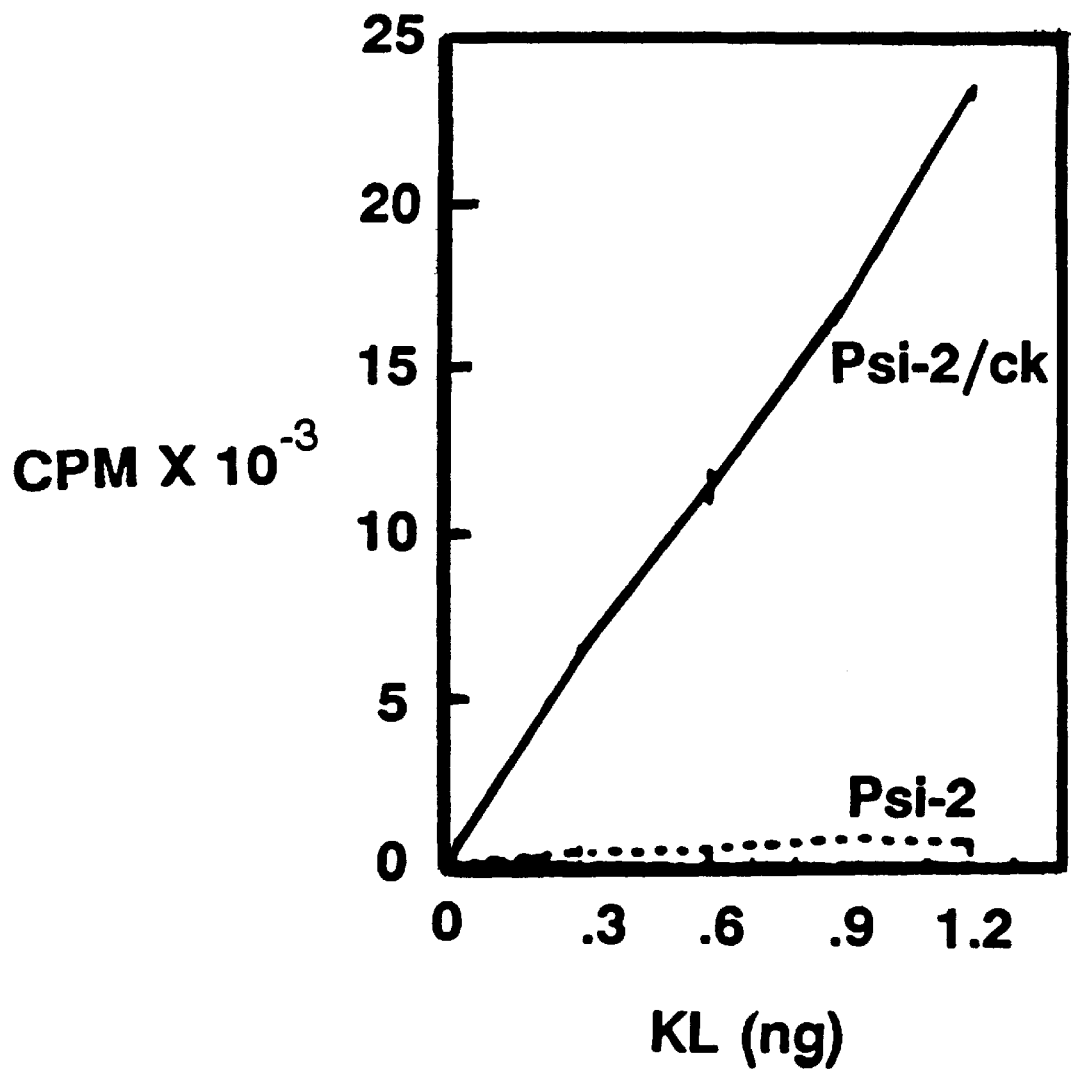
FIGS. 14A–14B. Binding of $^{125}$I-K to Mast Cells and c-kit-Expressing $\Psi$2 Cells.
 A. NIH $\Psi$2/c-kit cells containing the pLJ c-kit expression vector and expressing a high level of high c-kit protein.
 B. Mast cells derived from bone marrow of +/+ or W/W$^V$ adult mice or fetal liver cells of W/W or a normal littermate control (W/+ or +/+).
Figure 14B:
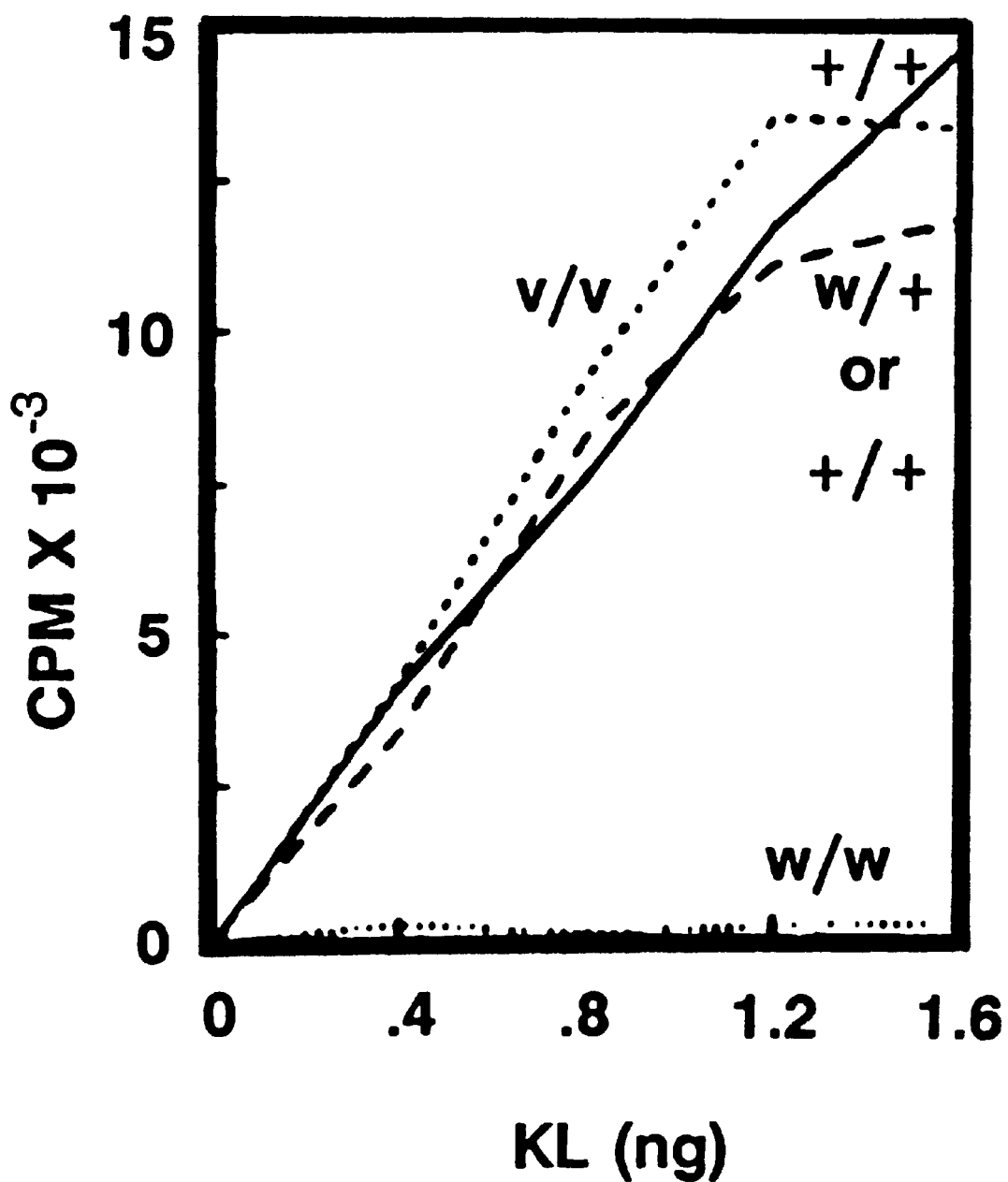

The fibroblast-derived hematopoietic growth factor KL had been shown to facilitate the proliferation of primary bone marrow mast cells and peritoneal mast cells and to display erythroid burst-promoting activity. To determine if KL is the ligand of the c-kit receptor, it was first thought to demonstrate specific binding of KL to cells that express high levels of the c-kit protein; mast cells (BMMC) and NIH #2 cells expressing the c-kit cDNA. KL was labeled to high specific activity with $^{125}$I by using the modified chloramine T method (88). Analysis of the labeled material by SDS-PAGE showed a single band of 28–30 kd (FIG. 13), and mast cell proliferation assays indicated that the labeled material had retained its biological activity. Binding of increasing concentrations of $^{125}$I-KL to NIH #2 cells expressing the c-kit cDNA, NIH #2 control cells, normal BMMC, and W/W, W/+, and W$^v$/W$^v$ BMMC at 4° C. was measured. The results shown in FIG. 14 indicated binding of labeled KL to NIH #2 c-kit cells and to +/+, W/+, and W$^v$/W$^v$ mast cells, but not to NIH #2 control cells or W/W mast cells. The W$^v$ mutation is the result of a missense mutation in the kinase domain of c-kit that impairs the in vitro kinase activity but does not affect the expression of the c-kit protein on the cell surface (36). By contrast, W results from a deletion due to a splicing defect that removes the transmembrane domain of the c-kit protein; the protein therefore is not expressed on the cell surface (36). Furthermore, binding of $^{125}$I-KL could be completed with unlabeled KL and with two different anti-c-kit antisera. These results indicated binding of $^{125}$I-labeled KL cells that express c-kit on their cell surface.

Figure 15A:
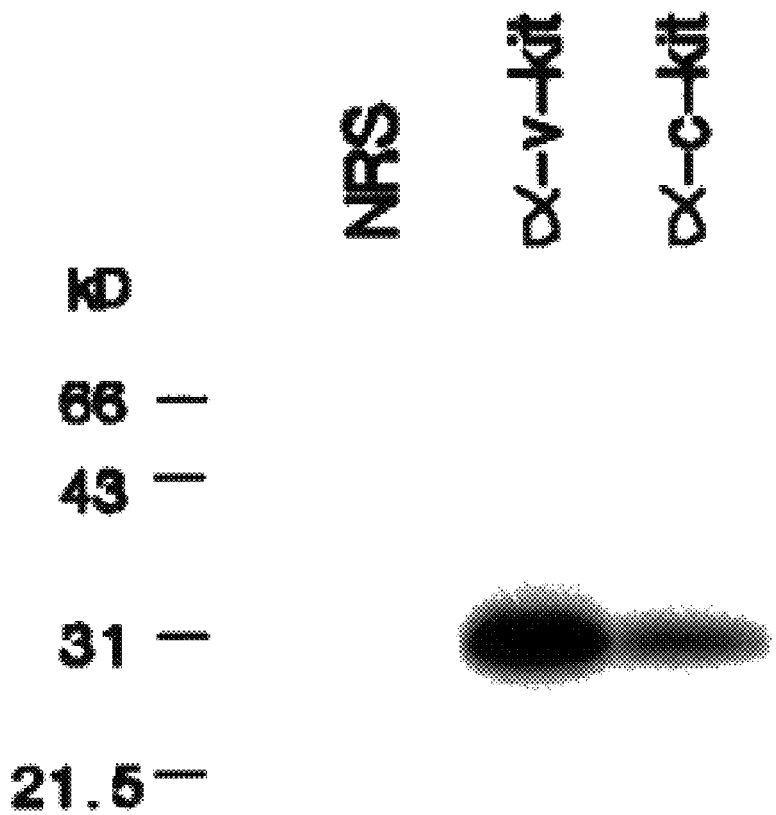
FIGS. 15A–15B. Coprecipitation and Cross-Linking of $^{125}$I-KL with the c-kit receptor on mast cells.
 A. Coprecipitation of KL with normal rabbit serum (NRS) or two anti-c-kit rabbit antisera ($\alpha$-c-kit).
 B. Cross-linking of KL to c-kit with disuccinimidyl substrate. SDS-page analysis was on either 12% or 7.5% polyacrylamide gels. Cross-linked species are labeled "KL+cK".

To obtain more direct evidence that KL is the ligand of the c-kit receptor, it was determined if receptor-ligand complexes could be purified by immunoprecipitation with c-kit antisera. This experiment requires that a KL-c-kit complex be stable and not be affected by the detergents used for the solubilization of the c-kit receptor. Precedent for such properties of receptor-ligand complexes derives from the closely related macrophage colony-stimulating factor (CSF-1) receptor and PDGF receptor systems (89). $^{125}$I-KL was bound to receptors on BMMC by incubation at 4° C. Upon washing to remove free $^{125}$I-KL, the cells were solubilized by using the Triton X-100 lysis procedure and precipitated with anti-v-kit and anti-c-kit rabbit sera conjugated to protein A-Sepharose. $^{125}$I-KL was retained in immunoprecipitates obtained by incubation with anti-kit sera but not with nonimmune controls, as shown by the analysis of the immune complexes by SDS-PAGE (FIG. 15A), where recovery of intact $^{125}$I-KL was demonstrated from the samples containing the immune complexes prepared with anti-kit sera.

Figure 15B:
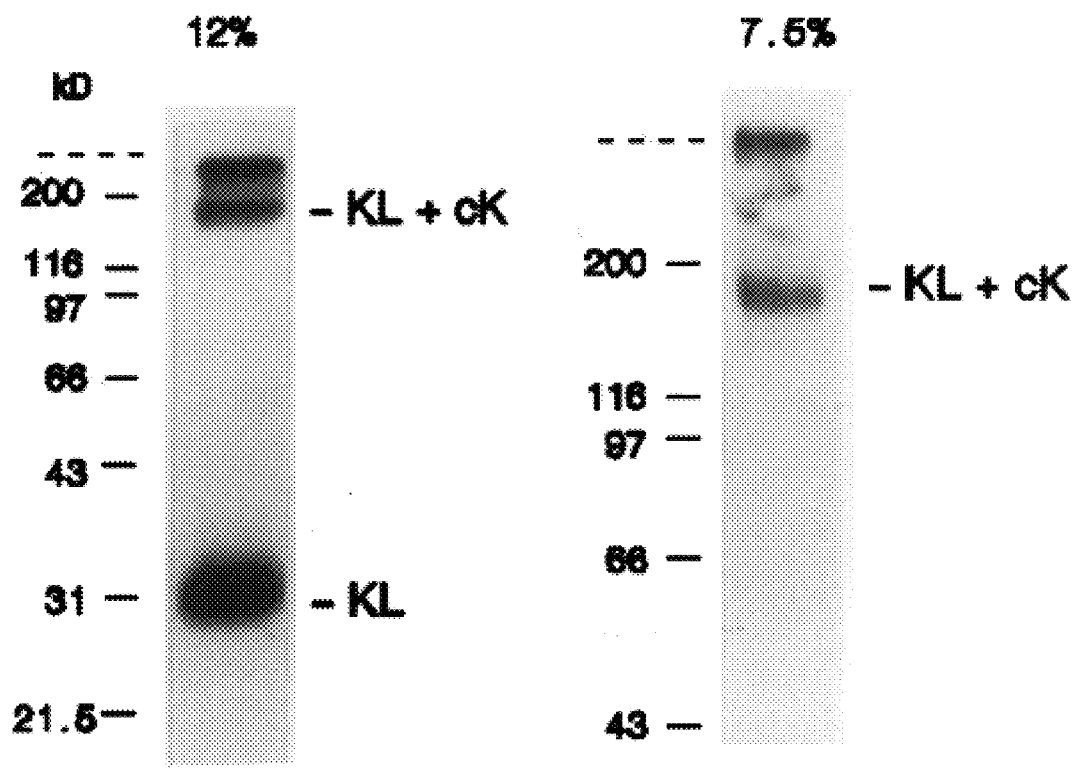

To further characterize the c-kit-KL receptor-ligand complexes, it was determined whether KL could be cross-linked to c-kit. BMMC were incubated with $^{125}$I-KL, washed and treated with the cross-linked disucciminidyl substrate. Cell lysates were then immunoprecipitated with anti-v-kit antiserum and analyzed by SDS-PAGE. Autoradiography indicated three species: one at approximately 30 kd, representing KL coprecipitated by not cross-linked to c-kit; one at 180–190 kd, corresponding to a covalently linked c-kit-KL monomer-monomer complex; and a high molecular weight structure that is at the interface between the separating and stacking gels (FIG. 15B). Molecular structures of similar size were observed if the cell lysates were separated directly on SDS-PAGE without prior immunoprecipitation. Following precipitation with nonimmune serum, no $^{125}$I-labeled molecules were observed. The formation of the high molecular weight structures was dependent on the incubation of KL with mast cells and was not observed by cross-linked KL with itself. Taken together, these results provide evidence that KL specifically binds to the c-kit receptor and is a ligand of c-kit.

Mapping of KL to the S1 locus

To test whether KL is encoded at the S1 locus, recombination analysis was used to determine the map position of KL with respect to a locus that is tightly linked to S1. This locus is the site of the transgene insertion in the transgenic line TG.EB (85). It was determined that genomic sequences cloned from the insertion site map 0.8±0.8 cM from S1. This therefore represents the closest known marker to S1.

To map KL with respect to the transgene insertion site, interspecific mapping analysis was employed utilizing crosses of C57BL/6J mice with mice of the species Mus spretus. This strategy exploits the observation that restriction fragment length polymorphism (RFLPs) for cloned DNA are observed much more frequently between mice of different species than between different inbred laboratory strains (90). Linkage between the 1.4 kb KL cDNA probe and TIS Dra/SaI, a probe from the transgene insertion site, was assessed by scoring for concordance of inheritance of their respective C57BL/6J or M. spretus alleles. These could be easily distinguished by analyzing RFLPs that are revealed by TaqI restriction digests. The results of this linkage analysis are shown in Table 2. Only one recombinant was found in 53 progeny. This corresponds to a recombination percentage of 1.9±1.9. Since this value is very close to the genetic distance measured between the transgene insertion site and S1, this result is consistent with the notion that KL maps to the S1 locus.

TABLE 2

Mapping of the Position of the KL Gene by Linkage Analysis Using an Interspecific Cross

| Probe | Nonrecominant | | Recombinant | |
|---|---|---|---|---|
| | | | Progeny | |
| 1.4 kb KL cDNA | B6 | Sp | B6 | Sp |
| TIS Dra/SaI | B6 | Sp | Sp | B6 |
| | 32 | 20 | 0 | 1 | n = 53
% recombination = 1.9 ± 1.9

The concordance of inheritance of C57B1/6J (B6) or M. spretus (Sp) alleles in progeny of an interspecific cross (see Experimental Procedures) was determined by scoring for TaqI RFLPs of the KL 1.4 kb cDNA probe and TIS Dra/SaI (a probed from a transgene insertion site that is tightly linked to S1; see Results). Percent recombination was calculated according to Green (1981).

Figure 16A:
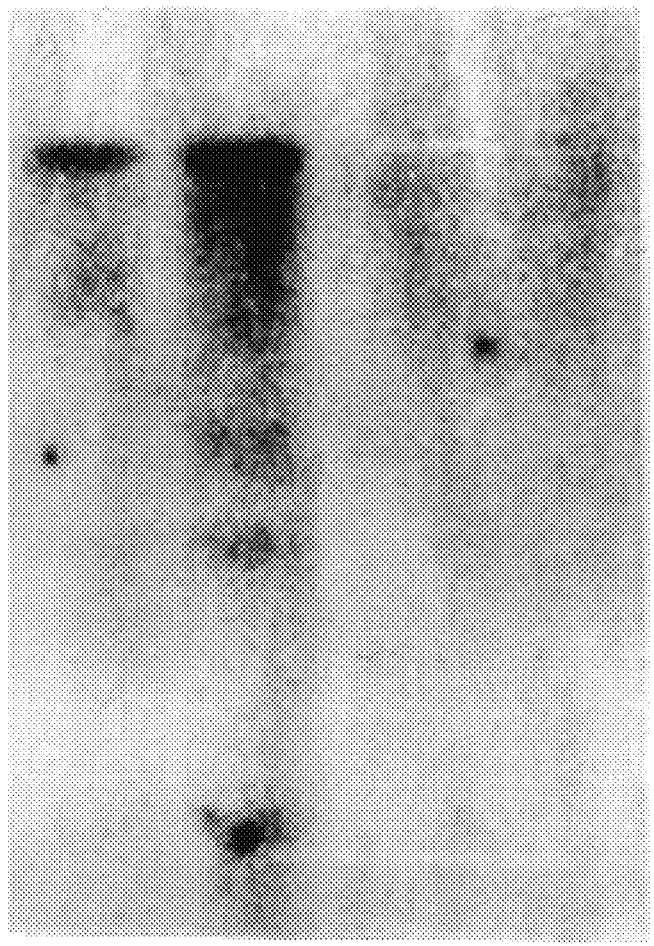
FIGS. 16A–16B. RFLP analysis of Taql-digested DNA from Sl/+ and SlISl mice. The Sl allele from C3HeB/Fej a/a CaJ Sl Hm mice was introduced into a C57BL/6J Sl Hm mice was introduced into a C57BL/6J background, and progeny of a C57BL/6J Sl$^{C3H}$xSl$^{C3H}$ cross were evaluated.
 A. Hybridazation of the 1.4 kB KL cDNA probe to DNA from two nonanemic (lanes SlI+) and two anemic (lanes SlISl) mice. No hybridization to the DNA from the SlISl mice was detected.
 B. Hybridization of the same blot to TIS Dra/SaI, a probe that is tightly linked to Sl (see Detailed Description, infra). This probe identifies a 4 kB C3HeB/FeJ-derived allele and a 2 kb C57BL/6J allele in the Sl$^{c3H}$1Sl$^{c3H}$ homozygotes.
Figure 16B:
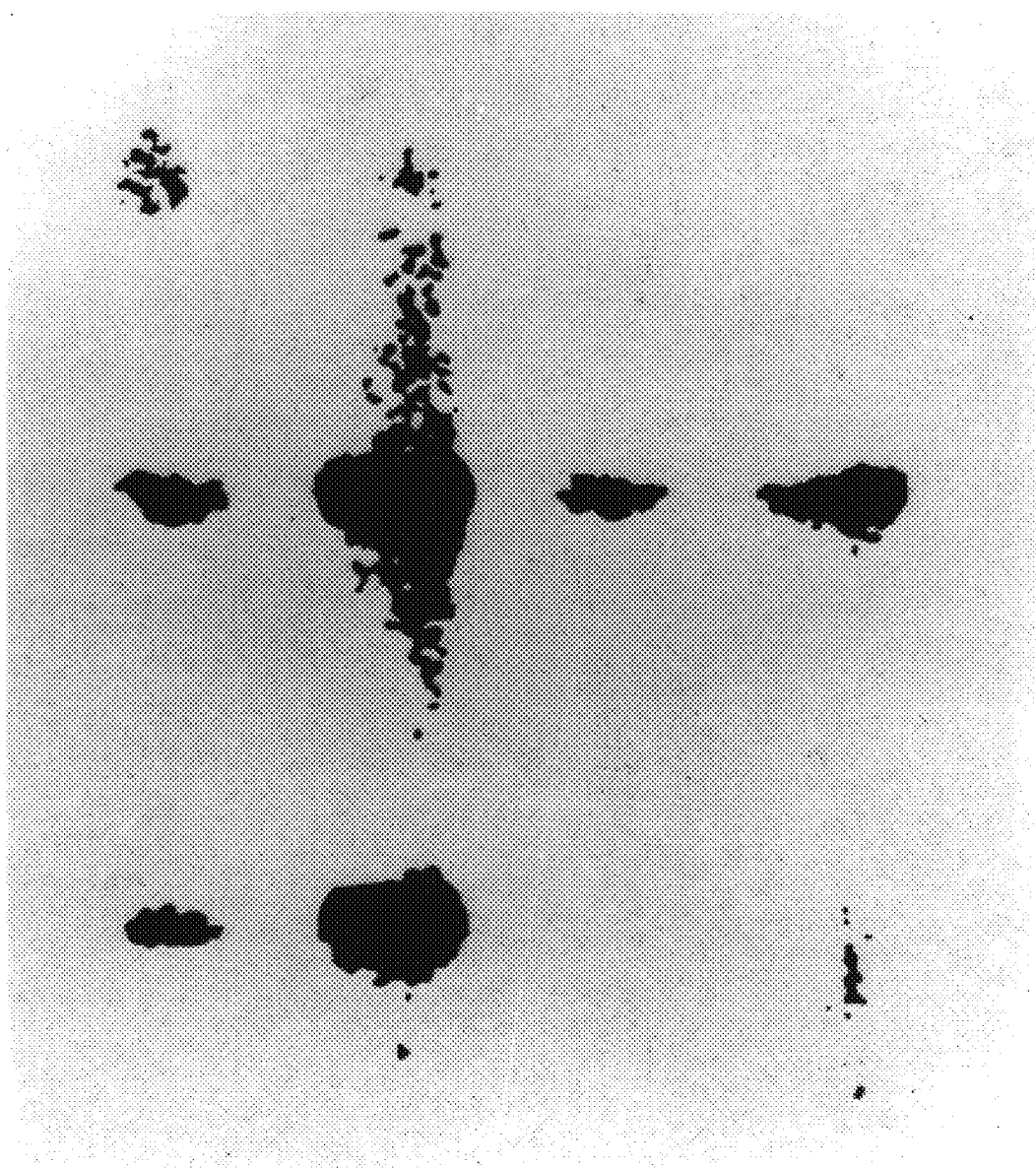

The locus identified by KL was also examined in mice that carry the original S1 mutation (50). For this purpose, the observation that the transgene insertion site locus is polymorphic in inbred strains was taken advantage of, and was utilized to determine the genotype at S1 during fetal development. C57BL/6J mice that carry the S1 mutation maintained in the C3HeB/FeJ strain were generated by mating, and F1 progeny carrying the S1 allele were intercrossed (C57BL/6J S1$^{3CH/}$+S1$^{C3H/}$+). Homozygous SIISI progeny from this mating are anemic and are homozygous for a C3HeB/FeJ-derived RFLP at the transgene integration site (FIG. 16). Nonanemic mice are either heterozygous S1I+ or wild type, and are heterozygous for the C3HeB/FeJ- and C57BL/6J-derived polymorphism or are homozygous for the C57BL/6J polymorphism, respectively. When genomic DNA from SII+ and SIISI mice was analyzed using the 1.4 kb KL cDNA probe, no hybridization to the homozygous SIISI DNA was observed (FIG. 16). It thus appears that the locus that encodes the KL protein is deleted in the S1 mutation. This finding further supports the notion that KL is the produce of the S1 gene.

Experimental Discussion

The discovery of allelism between the c-kit proto-oncogene and the murine W locus revealed the pleiotropic functions of the c-kit receptor in development and in the adult animal. Furthermore, it provided the first genetic system of a transmembrane tyrosine kinase receptor in a mammal. Mutations at the S1 locus and at the c-kit/W locus affect the same cellular targets. Because of the complementary and parallel properties of these mutations, it was proposed that the ligand of the c-kit receptor is encoded by the S1 locus.

The experiments reported herein provide evidence that the S1 gene encodes the ligand of the c-kit receptor. The evidence for this conclusion is a follows. Based on the knowledge of the function of the c-kit receptor designated KL, a putative ligand of the c-kit receptor designated KL was identified and purified (37). It was also demonstrated that specific binding of KL to the c-kit receptor, as evidence by the binding of KL to cells expressing a functional c-kit receptor and the formation of a stable complex between KL and the c-kit protein. KL-specific cDNA clones were derived and it was shown that KL maps to the S1 locus on mouse chromosome 10. In addition, it was also demonstrated that KL sequences are deleted in the genome of the S1 mouse. Taken together, these results suggest that KL is encoded by the S1 locus and is the ligand of the c-kit receptor, thus providing a molecular basis for the S1 defect.

The amino acid sequence predicted from the nucleotide sequence of the KL cDNA clone suggests that KL is synthesized as an integral transmembrane protein. The structural features of the primary translation product of KL therefore are akin to those of CSF-1. CSF-1 is synthesized as a transmembrane molecule, which is processed by proteolytic cleavage to form a soluble product that is secreted (91, 44). Presumable, like CSF-1, KL is also synthesized as a cell surface molecule that may be processed to form a soluble protein. The protein purified from conditioned medium of BALB/c 3T3 cells then would represent the soluble form of KL that was released from the cell membrane form by proteolytic cleavage. Although the post-translational processing and expression of the KL protein have not yet been characterized, a cell surface-bound form of KL may mediate the cell—cell interactions proposed for the proliferative and migratory functions of the c-kit/W receptor system. In agreement with the notion of a cell membrane-associated form of KL, a soluble c-kit receptor-alkaline phosphatase fusion protein has been shown to bind to the cell surface of BALB/c 3T3 cells but not to fibroblasts derived from SII/SI mice (14).

A most significant aspect of the identification of the ligand of the c-kit receptor lies in the fact that it will facilitate the investigation of the pleiotropic functions of c-kit. In the hematopoietic system c-kit/W mutations affect the erythroid and mast cell lineages, and an effect on the stem cell compartment has been inferred as well. In erythroid cell maturation c-kit/KL plays an essential role, and this is best seen by the anemia of mutant animals. Furthermore, the number of CFU-E in fetal livers from W/W and SlISI$^d$ animals is repressed, whereas the number of BFU-E remains normal, suggesting that c-kit/KL facilitates the progression from the BFU-E to the CFU-E stage of differentiation (90, 35). In this regard, KL has been shown to stimulate the proliferation and differentiation of BFU-E (day 7) as well as earlier erythroid multipotential precursors in bone marrow, which appear at later times in culture (day 14–20) (37).

An essential role for c-kit/KL in the proliferation, differentiation, and/or survival of mast cells in vivo has been inferred because of the absence of mast cells in W and S1 mutant mice (72, 73). The precise stage(s) at which c-kit/KL function is required in mast cell differentiation is not known. The in vitro derivation of BMMC from bone marrow or fetal liver does not require c-kit/KL function since BMMC can be generated with comparable efficiency from both normal and W mutant mice (60). Applicants' demonstration of proliferation of BMMC and connective tissue-type mast cells in response to KL indicates a role for c-kit/KL at multiple stages in mast cell proliferation and differentiation independent of IL-3 and IL-4, which are thought to be mediators of allergic and inflammatory responses (66). In the stem cell compartment the affected populations possibly include the spleen colony-forming units (CFU-S), which produce myeloid colonies in the spleen of lethally irradiated mice, as well as cells with long-term repopulation potential for the various cell lineages (80, 81, 82, 83). It will now be of interest to determine the effect of KL on the self-renewal or the differentiation potential of hematopoietic stem cell populations in vitro, possibly in combination with other hematopoietic growth factors, in order to identify the stage(s) where c-kit/KL functions in stem cells. Another possible function for c-kit might be to facilitate the transition from noncycling to cycling cells (31). The increased radiation sensitivity of SlISI$^d$ and of W/W$^v$ mice might suggest such a role in stem cell dynamics; furthermore, the related PDGF receptor is known to promote entry into the cell cycle.

In gametogenesis the W and S1 mutations affect the proliferation and the survival of primordial germ cells, and their migration from the yolk sac splanchnopleure to the genital ridges during early development. In postnatal gametogenesis c-kit expression has been detected in immature and mature oocytes and in spermatogonia A and B as well as in interstitial tissue (39). In melanogenesis c-kit/KL presumable functions in the proliferation and migration of melanoblast from the neural crest to the periphery in early development as well as in mature melanocytes. The availability of KL may now facilitate in vitro studies of the function of the c-kit receptor in these cell systems.

The microenvironment in which c-kit-expressing cells function is defective in S1 mutant mice and is the presumed site where the c-kit ligand is produced. Because of the extrinsic nature of the mutation, the precise identity of the cell types that produce KL in vivo is not known. In vitro systems that reproduce the genetic defect of the W and the S1 mutations, however, have shed some light on this question. In the long-term bone marrow culture system, SlISI$^d$ adherent cells are defective but the nonadherent hematopoietic cells are not, and in the mast cell-fibroblast coculture system, SlIISI$^d$ fibroblasts are defective but the mast cells are not (12, 16). The results from these in vitro systems then would suggest that hematopoietic stromal cells and embryonic and connective tissue fibroblasts produce KL. The BALB/c 3T3 cell line, which is of embryonic origin, expresses significant levels of KL and was the source for its purification. Knowledge of KL-expressing cell types may help to evaluate if there is a function for c-kit in the digestive tract, the nervous system, the placenta, and certain craniofacial structures, sites where c-kit expression has been documented (35, 39). No S1 or W phenotypes are known to be associated with these cell systems.

Interspecific backcrosses were used to establish close linkage between the KL gene, the S1 locus, and the transgene insertion locus Tg.EB on mouse chromosome 10. A similar approach had previously been used to map the Tg.EB locus in the vicinity of S1. The finding that the KL coding sequences are deleted in the original S1 allele, however, supports the identity of the S1 locus with the KL gene. The size of the deletion in the S1 allele at this time is not known. It will be important to determine whether its affects neighboring genes as well.

The lack of KL coding sequences in the S1 allele indicates that this allele is a KL null mutation. When homozygous for the S1 allele, most mice die perinatally of macrocytic anemia, and rare survivors lack cost pigmentation and are devoid of germ cells (5). This phenotype closely parallels that of severe c-kit/W loss-of-function mutations, in agreement with the ligand-receptor relationship of KL and c-kit. Although differences exist between SIISI and W/W homozygotes, e.g., in germ cell development, S1 may have a more pronounced effect, and in hematopoiesis S1 may cause a more severe anemia; however, it is not known if these differences are a result of different strain backgrounds or are possibly effects of the S1 deletion on neighboring genes (5).

The original W mutation is an example of a c-kit null mutation (36). When heterozygous with the normal allele, WI+ mice typically have a ventral spot but no cost dilution and no effects on hematopoiesis and gametogenesis. The weak heterozygous phenotype of WI$^+$ mice is in contrast to the phenotype of heterozygous SII$^+$ mice, which have moderate macrocytic anemia and a diluted coat pigment in addition to a ventral spot and gonads that are reduced in size. Thus 50% gene dosage of KL is limiting and is not sufficient for normal function of the c-kit receptor, yet 50% dosage of the c-kit receptor does not appear to be limiting in most situations.

The c-kit receptor system functions in immature progenitor cell populations as well as in more mature cell types in hematopoiesis, gametogenesis, and melanogenesis. Severe S1 or W mutations may block the development of these cell lineages, and therefore a function for the c-kit receptor in more mature cell populations would not be evident. S1 and W mutations in which c-kit/KL function is only partially impaired often reveal effects in more mature cell populations. Numerous weak S1 alleles are known. Their phenotypes, e.g., in gametogenesis and melanogenesis, will be of great value in the elucidation of the pleiotropic functions of the c-kit receptor system.

EXPERIMENT NUMBER 3

KL-1 AND KL-2

Experimental Materials

Mice and tissue culture

WBB6 +/+, C57BL/6J and 129/Sv-S1$^d$/+ mice were obtained from the Jackson Laboratory (Bar Harbor, Me.) (52). 129/Sv-S1$^d$/+ male, and female mice were mated and day 14 fetuses were obtained and used for the derivation of embryonic fibroblasts according to the method of Todaro and Green (54). Mast cells were grown from bone marrow of adult +/+ mice in RPMI-1640 medium supplemented with 10% fetal calf serum (FCS), conditioned medium from WEHI-3B cells, non-essential amino acids, sodium pyruvate, and 2-mercapto-ethanol (RPMI-Complete (C)) (36). Balb/3T3 cells (1) were grown in Dulbecco's Modified MEM (DME) supplemented with 10% calf serum (CS), penicillin and streptomycin. COS-1 cells (18) were obtained from Dr. Jerrard Hurwitz (SKI) and were grown in DME supplemented with 10% fetal bovine serum, glutamine, penicillin and streptomycin.

Production of anti-KL antibodies

Murine KL was purified from conditioned medium of Balb3T3 cells by using a mast cell proliferation assay as described elsewhere (37). In order to obtain anti-KL antibodies one rabbit was immunized subcutaneously with 1 μg of KL in complete Freund's adjuvant. Three weeks later the rabbit was boosted intradermally with 1 μg in incomplete Freunds adjuvant. Serum was collected one week later and then biweekly thereafter. The $^{125}$I-labelled KL used for this purpose was iodinated with chloramine T with modifications of the method of Stanley and Gilbert as described previously (38).

cDNA Library Screening

Poly(A) RNA was prepared by oligo (dT)-cellulose chromatography from total RNA of Balb/c 3T3 fibroblast. A custom made plasmid cDNA library was then prepared by Invitrogen Inc. Essentially, double-stranded cDNA was synthesized by oligo dT and random priming. Non-palindromic BstXI linkers were ligated to blunt-ended cDNA and upon digestion with BstXI the cDNA was subcloned into the expression plasmid pcDNAI (Invitrogen). The ligation reaction mixture then was used to transform E. coli MC1061/P3 by the electroporation method to generate the plasmid library. The initial size of the library was approximately $10^7$ independent colonies. For screening of the plasmid library an end-labelled oligonucleotide probe described previously was used (38). Hybridization was done in 6X SSC at 63° C. and the final wash of the filters was in 2X SSC and 0.2% SDS at 63° C. The inserts of recombinant plasmids were released by digestion with HindIII and XbaI and then subcloned into the phage M13mp18 for sequence analysis.

PCR amplification (RT-PCR) and sequence determination

Total RNA from tissues and cell lines was prepared by the guanidium isothiocyanate/CsCl centrifugation method of Chirgwin (10). The RT-PCR amplification was carried out essentially as described previously (38). The following primers were used for RT-PCR:

Primer #1: 5'-GCCCAAGCTTCGGTGCCTTTCCTTATG-3' (nt. 94–107);

Primer #2: 5'-AGTATCTCTAGAATTTTACACCTCTTGAAATTC TCT-3' (nt. 907–929); (SEQ ID NO:13)

Primer #3: 5'-CATTTATCTAGAAAACATGAACTGTTACCAGCC-3' (nt. 963–978) (SEQ ID NO:14);

Primer #4: 5'-ACCCTCGAGGCTGAAATCTACTTG-3' (nt. 1317–1333) (SEQ ID NO:15).

For cDNA synthesis, 10 μg of total RNA from cell lines or tissues in 50 μl of 0.05 mM Tris-HCl (pH 8.3), 0.75 M KCl, 3 mM MgCl$_2$, 10 mM DTT, 200 μM dNTP's and 25 U of RNAsin (BRL) was incubated with 50 pmole of antisense primer and 400 U of Moloney murine leukemia virus reverse transcriptase (BRL) at 37° C. for 1 hour. The cDNA was precipitated by adding 1/10 volume of 3 M NaOAc (pH 7.0) and 2.5 volume of absolute ethanol and resuspended in 50 μl of ddH$_2$O. PCR was carried out for 30 cycles in 100 μl of 10 mM Tris-HCl (pH 8.3), 50 mM KCl, 1.5 mM MgCl$_2$, 0.01% (w/v) gelatin, 200 μM dNTP's, 500 pmole of both sense and antisense primers and 2.5 U of Taq polymerase (Perkin-Elmer-Cetus). HindIII sites and XbaI sites were placed within the sense—and antisense primers respectively. The amplified DNA fragments were purified by agarose gel electrophoresis, digested with the appropriate restriction enzymes, and subcloned into M13mp18 and M13mp19 for sequence analysis (49). The KL-1, KL-2, KL-S and KL-S1$^d$ PCR products were digested with HindIII and XbaI and subcloned into the expression plasmids pCDM8 and pcD-NAI (Invitrogen). Miniprep plasmid DNA was prepared by the alkaline-lysis method (48) followed by phenol-chloroform extraction and ethanol precipitation. Maxiprep plasmid DNA used for the transfection of COS-1 cells was prepared by using the "Qiagen" chromatography column procedure.

RNase Protection Assay

A riboprobe for RNAse protection assays was prepared by linearizing the KL-1 containing pcDNAI plasmid with SpeI. The antisense riboprobe was then synthesized by using SP6 polymerase according to the Promega Gemini kit. Riboprobe labelled to high specific activity was then hybridized to 10 or 20 μg of total RNA in the presence of 80% formamide at 45° C. overnight. The hybridization mixture was digested with RNase A and T1 (Boehringer-Mannheim) and treated with proteinase K (48) and the protected labelled RNA fragments were analyzed on a 4% urea/polyacrylamide gel. Autoradiograms of RNAse protection assay were analyzed by densitometry and parts of the films were reconstructed on a PhosphoImage analyzer (Molecular Dynamics) for better resolution.

Transient expression of "KL" cDNAs in COS-1 cells

For transient expression of KL cDNAs COS-1 cells were transfected with the DEAE-dextran method described previously (20) with minor modifications. Briefly, COS-1 cells were grown to subconfluence one day before use and were trypsinized and reseeded on 150 mm petri dishes at a density of 6×10$^6$ cells per dish. After 24 hours, the cells had reached about 70% confluence and were transfected with 5 μg of plasmid DNA in the presence of 10% DEAE-dextran (Sigma) for 6 to 12 hours. Medium containing plasmid DNA was removed and the cells were chemically shocked with 10% DMSO/PBS$^{++}$ for exactly 1 minute. Residual DMSO was removed by washing the cells with PBS$^{++}$ twice. Transfected COS-1 cells were grown in DME plus 10% fetal calf serum, 100 mg/ml L-glutamine, and antibiotics.

Pulse chase and immunoprecipitation analysis of "KL" proteins

Transfected COS-1 cells were used for pulse-chase experiments 72 hours after the transfection. Cells were incubated with methionine-free DME containing 10% dialyzed fetal calf serum for 30 minutes and labelled with $^{35}$S-methionine (NEN) at 0.5 mCi/ml. At the end of the labelling period, the labelling medium was replaced with regular medium containing an excess amount of methionine. In order to determine the effect of phorbol 12-myristate 13-acetate (PMA) and A23187 on the proteolytic cleavage of KL, 1 µM PMA or 1 µM A23187 was added to the transfected cells at the end of the labelling period after replacement of the labelling medium with regular medium. The cells and supernatants were collected individually at the indicated times for immunoprecipitation analysis. Cell lysates were prepared as described previously (35) in 1% Triton-100, 20 mM Tris (pH 7.5), 150 mM NaCl, 20 mM EDTA, 10% glycerol and protease inhibitors phenylmethyl sulfonyl chloride (1 mM) and leupeptin (20 µg/ml). For the immunoprecipitation analysis of KL protein products the anti-mouse KL rabbit antiserum was used. The anti-KL serum was conjugated to protein-A Sepharose (Pharmacia) and washed 3 times with Wash A (0.1% Triton X-100, 20 mM Tris (pH 7.5), 150 mM NaCl, 10% glycerol). Anti-KL serum-protein A sepharose conjugate was incubated with supernatant and cell lysate at 4° C. for at least 2 hours. The immunoprecipitates then were washed once in Wash B (50 mM Tris, 500 mM NaCl, 5 mM EDTA, 0.2% Triton X-100), 3 times in Wash C (50 mM Tris, 500 mM NaCl, 0.1% Triton X-100, 0.1% SDS, 5 mM EDTA) and once in Wash D (10 mM Tris, 0.1% Triton X-100). For gel analysis immunoprecipitates were solubilized in SDS sample buffer by boiling for 5 minutes, and analyzed by SDS-PAGE (12%) and autoradiography.

Determination of biological activity of soluble KL

Mast cells were grown from bone marrow of adult WBB6 +/+ mice in RPMI-1640 medium supplemented with 10% fetal calf serum, conditioned medium from WEHI-3B cells, non-essential amino acids, sodium pyruvate and 2-mercaptoethanol (RPMI-Complete) as described previously (37). Non-adherent cells were harvested by centrifugation and refed weekly and maintained at a cell density of <7×10$^5$ cells/ml. The mast cell content of cultures was determined weekly by staining cytospin preparations with 1% toluidine blue in methanol. After 4 weeks, cultures routinely contained >95% mast cells and were used for proliferation assay. Supernatants from transfected COS-1 cells were collected from 48 to 72 hours after transfection. The biological activity of soluble KL in the supernatants was assessed by culturing BMMCs with different dilutions of COS-1 cell supernatants in the absence of IL-3. BMMCs were washed three times with complete RPMI and grown in 0.2% IL-3. The following day, cells were harvested and suspended in complete RPMI (minus IL-3) and 10$^4$ BMMCs in 100 µl/well were seeded in a 96-well plate. Equal volume of diluted supernatant was added to each well and cultures were incubated for 24 hours at 37° C., 2.5 µCi of [$^3$H]-thymidine/well was then added and incubation was continued for another 6 hours. Cells were harvested on glass fiber filters (GF/C Whatman) and thymidine incorporation was determined in a scintillation counter. Assays were performed in triplicate and the mean value is shown. Standard deviations of measurements typically did not exceed 10% of the mean values.

Experimental Results

Alternatively Spliced Transcript of KL Encodes a Truncated Transmembrane Form of the KL Protein A cDNA clone, which had been isolated from a mouse 3T3 fibroblast library and contained most of the KL coding sequences (267 amino acids), has been described herein. In an attempt to obtain the complete cDNA sequences corresponding to the 6.5 kb KL mRNA, a plasmid cDNA library was constructed by suing polyA° RNA from Balb/c3T3 fibroblasts. The plasmid vector pcDNAI which was used for this purpose is a mammalian expression vector in which cDNA inserts are expressed from a CMV promoter and contains an SC40 origin of replication for transient expression in COS cells (Invitrogen). The library was screened with oligonucleotide probes corresponding to N-terminal and C-terminal KL coding sequences as described herein. A cDNA clone which contains the complete KL coding sequences as well as 5' and 3' untranslated sequences was obtained. The nucleotide sequence of this clone (FIG. 17) is in agreement with the previously published sequences except for a single base change at position 664 which results in the substitution at serine 206 to alanine (2,38).

Figure 18A:
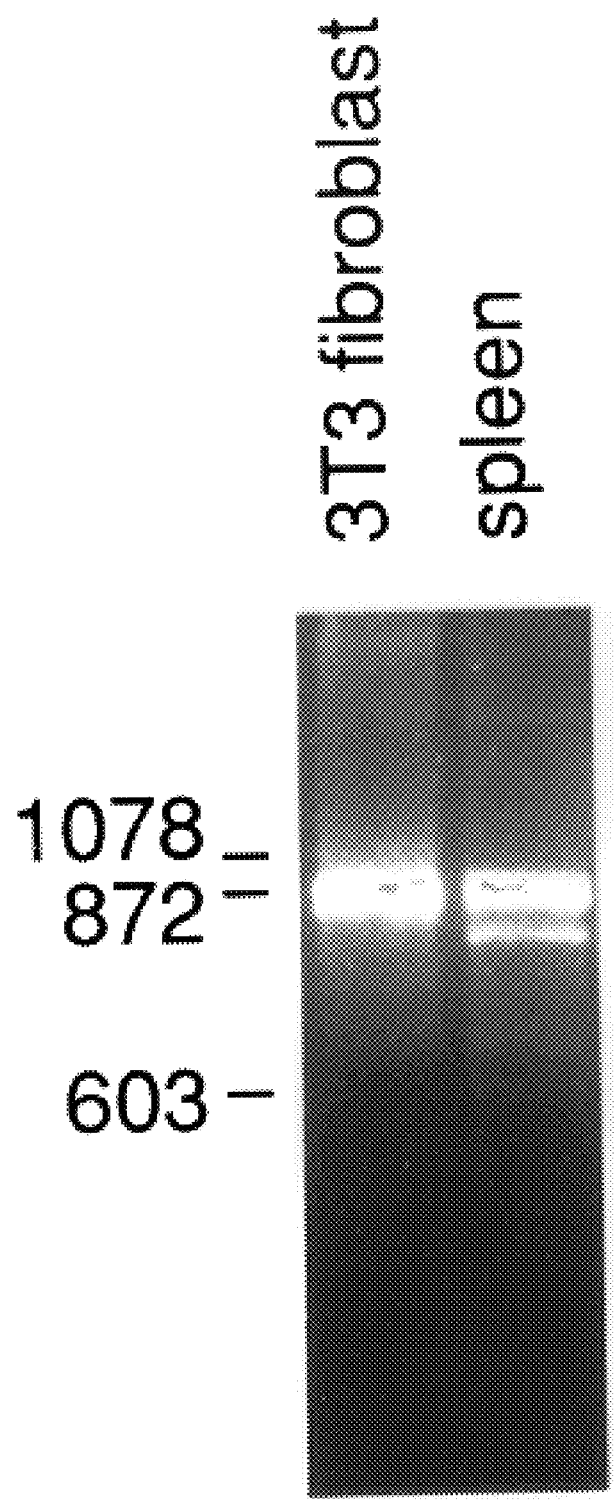
FIGS. 18A–18B. Panels A and B. Identification by RT-PCR cloning of KL cDNAs from normal tissues and Sl$^d$ mutant fibroblasts. Total RNA was obtained from different tissues of C57BI6/J mice and Sl$^d$/+ fibroblasts. RT-PCR reactions with RNA (10 $\mu$g) from normal tissues and Balb 3T3 cells were done using primers #1 and #2 and reactions with RNA from +/+ and Sl$^d$/+ fibroblasts were done by using the primer combinations #1, +#2, #1+#3 and #1+#4. The reaction products were analyzed by electrophoresis in 1% NuSieve agarose gels in the presence of 0.25 $\mu$g/ml ethidium bromide. The migration of $\phi$X174 Hae III DNA markers is indicated.
Figure 18B:
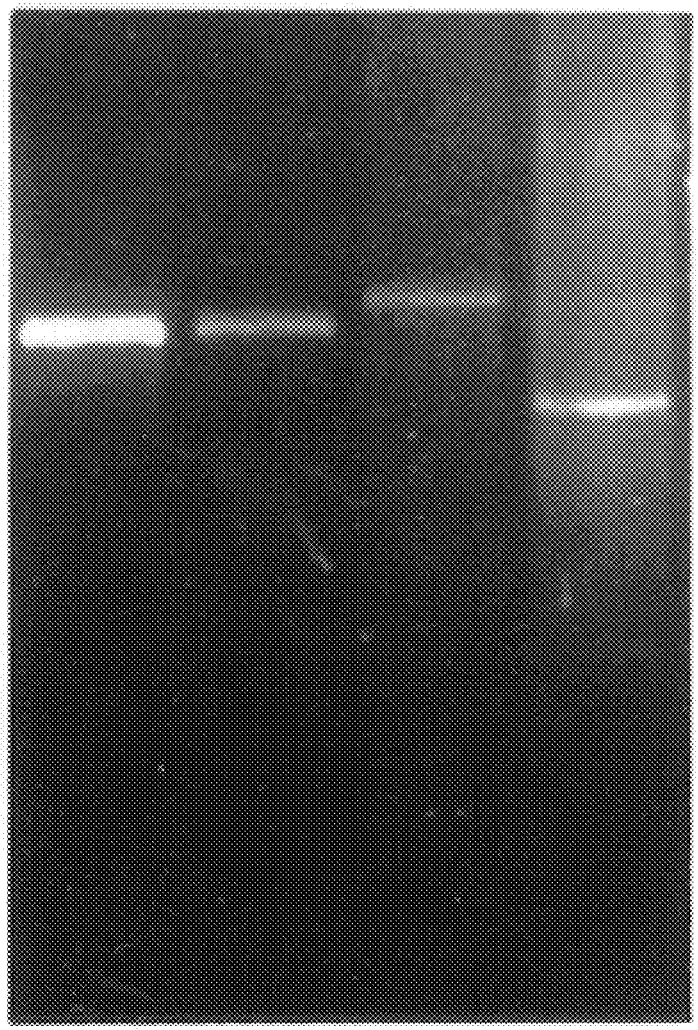
Figure 19:
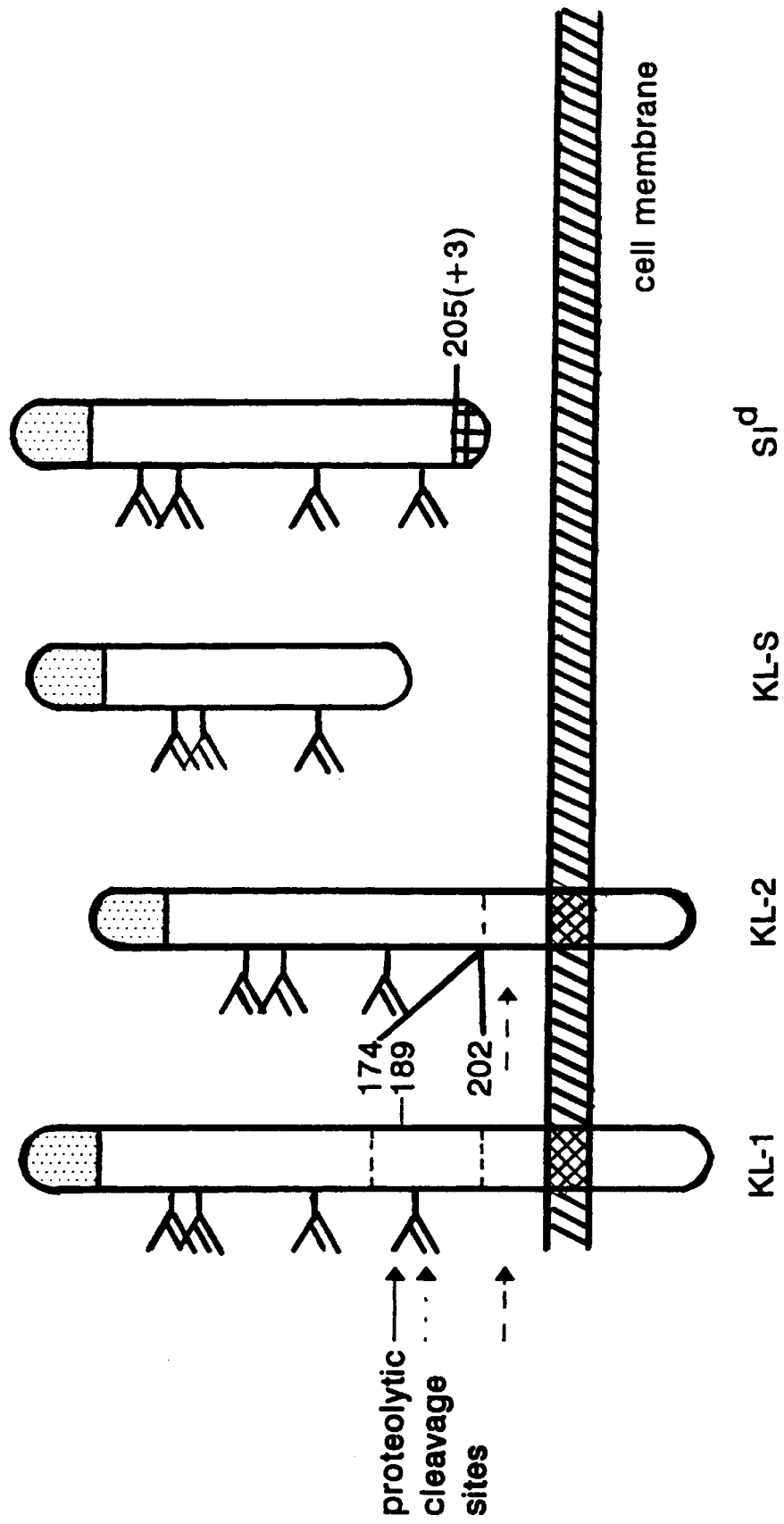
FIG. 19. Topology of different KL protein products. Shaded areas delineate N-terminal signal peptides, solid black areas transmembrane domains and Y N-linked glycosylation sites. Dotted lines indicate the exon boundaries of the alternatively spliced exon and corresponding amino acid numbers are indicated. Arrows indicate the presumed proteolytic cleavage sites. The shaded region at the C-terminus of KL-Sl$^d$ indicates amino acids that are not encoded by KL. KL-S designates the soluble form of KL produced by proteolytic cleavage or the C-terminal truncation mutation of KL.

The analysis of murine KL cDNA clones by Anderson and collaborators indicated a spliced cDNA with an inframe deletion of 48 nucleotides suggesting the presence of alternatively spliced KL RNA transcripts in KL expressing cells (2). To identify alternatively spliced KL RNA transcripts in RNA from tissues and cell lines, the RT-PCR method was used. The primers used corresponded to the 5' and 3' untranslated regions of the KL cDNA and were modified to contain unique restriction sites. Electrophoretic analysis of the RT-PCT reaction products shown in FIG. 18 indicates a single fragment of approximately 870 bp in the samples from Balk3T3 cells and brain, whereas in the samples from spleen, testis and lung two fragments were seen, approximately 870 and 750 bp in size. For further analysis the two PCR reaction products were subcloned into the mammalian expression vector pCDM8. DNA sequence analysis first indicated that the larger PCR product corresponds to the known KL cDNA sequence, subsequently referred to as KL-1. In the smaller PCR product, however, a segment of 84 nucleotides of the KL coding sequences was lacking, generating an inframe deletion. The deletion endpoints corresponded to exon boundaries in the rate and the human KL genes and it is quite likely that these boundaries are also conserved in the mouse gene (27). therefore, the smaller PCR product appeared to correspond to an alternatively spliced KL RNA transcript, designated KL-2. The exon missing in KL-2 precedes the transmembrane domain; it contains one of the four N-linked glycosylation sites and includes the known C-terminus (ala-166 and Ala-167) of the soluble form of KL (58). KL-2 therefore is predicted to encode a truncated version of KL-1 which is presumably synthesized as a transmembrane protein (FIGS. 17 and 19).

KL-2 Expressed in a Tissue Specific Manner

Figure 20:
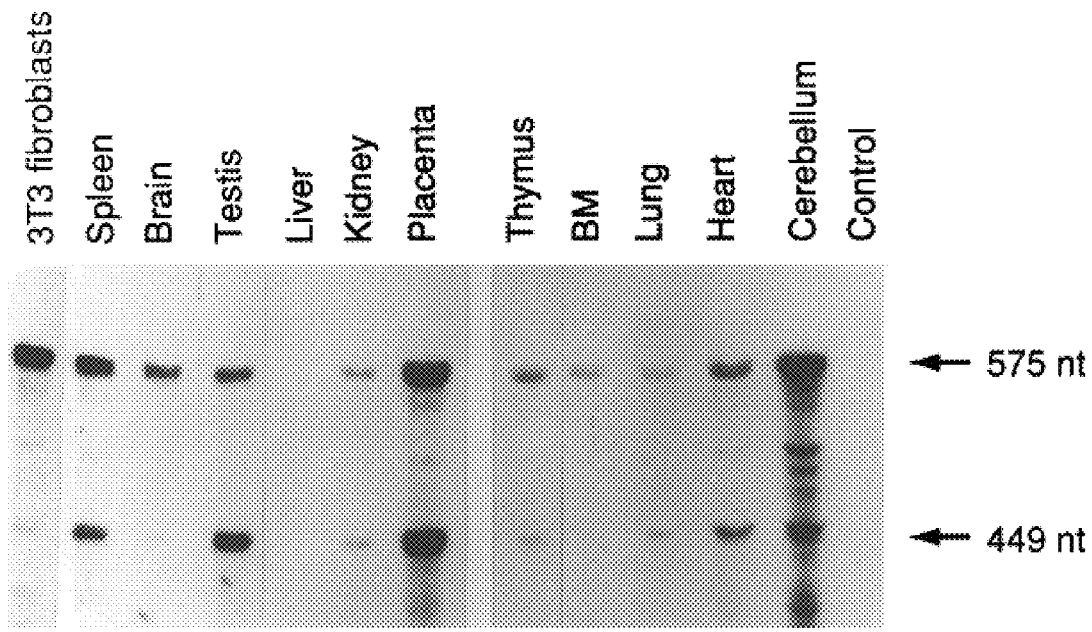
FIG. 20. Identification of KL-1 and KL-2 transcripts in different tissues by RNase protection assays. $^{32}$P-labelled antisense riboprobe (625 nt.) was hybridized with 20 $\mu$g total cell RNA from tissues and fibroblasts except for lung and heart where 10 $\mu$g was used. Upon RNase digestion, reaction mixtures were analyzed by electrophoresis in a 4% polyacrylamide/urea gel. For KL-1 and KL-2 protected fragments of 575 nts. and 449 nts., are obtained respectively. Autoradiographic exposures were for 48 or 72 hours, except for the 3T3 fibroblast RNA, which was for 6 hours.

The alternatively spliced transcript KL-2 had been detected in spleen, testis and lung RNA, but not in fibroblasts and brain RNA, suggesting that the expression of KL-2 may be controlled in a tissue specific manner. In order to address this question in more detail the steady state levels of KL-1 and KL-2 RNA transcripts in RNA were determined from a wide variety of tissues by using an RNAse protection assay. pcDNAI plasmid containing the KL-1 cDNA was linearized with SpeI in order to generate an RNA hybridization probe of 625 nucleotides by using SP6 RNA polymerase. The probe was hybridized with 20 µg of total RNA from Balb/c 3T3 fibroblasts, brain, spleen and testis of a 40 days old mouse, as well as from brain, bone marrow, cerebellum, heart, lung, livers, spleen and kidney of an adult mouse and placenta (14 days p.c.). The samples then were digested with RNAse and the reaction products analyzed by electrophoresis in a 4% urea/polyacrylamide gel. In these experiments KL-1 mRNA protected a single fragment of 575 bases, while KL-2 mRNA protected fragments of 449 and 42 nucleotides. As shown in FIG. 20, in Balb/C3T3 fibroblasts, KL-1 is the predominant transcript whereas the KL-2 is barely detectable. In brain and thymus KL-1 is the predominant transcript, but in spleen, testis, placenta, heart and cerebellum both KL-1 and KL-2 transcripts are seen in variable ratios. The ratio of the KL-1 to KL-2 in tissues determined by densiometry in brain is 26:1, in bone marrow 3:1, in spleen 1.5:1 and in testis (40 days p.n.) 1:2:6. These results suggest that the expression of KL-1 and KL-2 is regulated in a tissue-specific manner.

Biosynthetic Characteristics of KL Protein Products in COS Cells

Figure 21A:
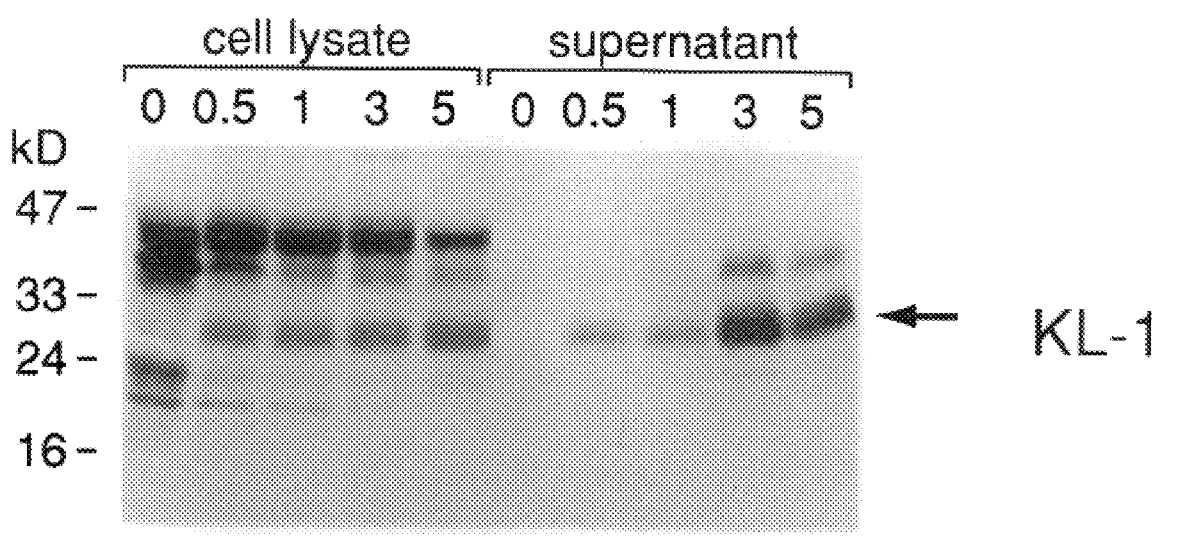
FIGS. 21A–21C. Biosynthetic characteristics of KL-1 and KL-2 protein products in COS cells. COS-1 cells were transfected with 5 $\mu$g of the KL-1 and KL-2 expression plasmids, using the DEAE-dextran method. After 72 hours the cells were labelled with $^{35}$S-Met for 30 minutes and then chased with complete medium. Supernatants and cell lysates were immunoprecipitated with anti-KL rabbit serum. Immunoprecipitates were analyzed by SDS-PAGE (12%). Migration of molecular weight markers is indicated in kilo daltons (kD).
Figure 21B:
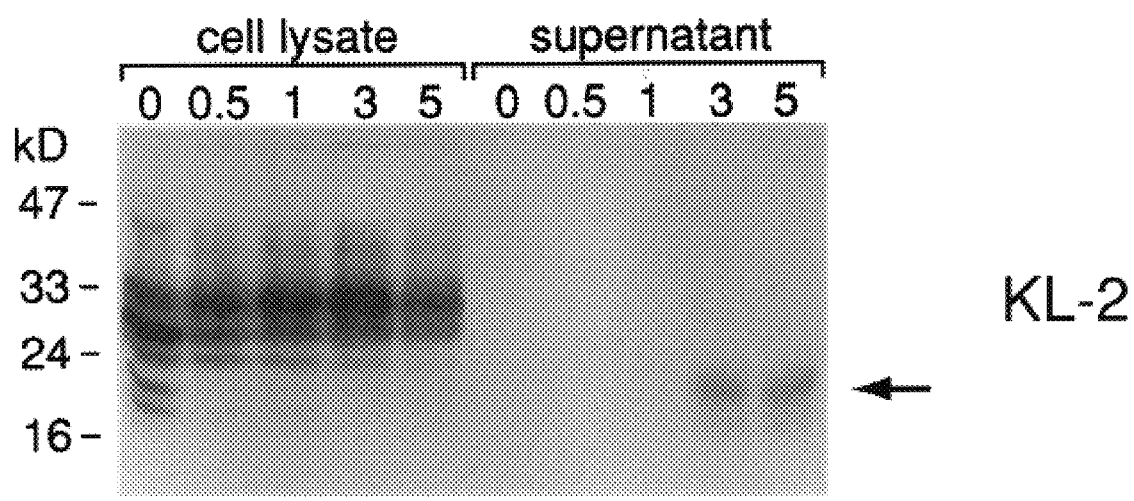
Figure 21C:
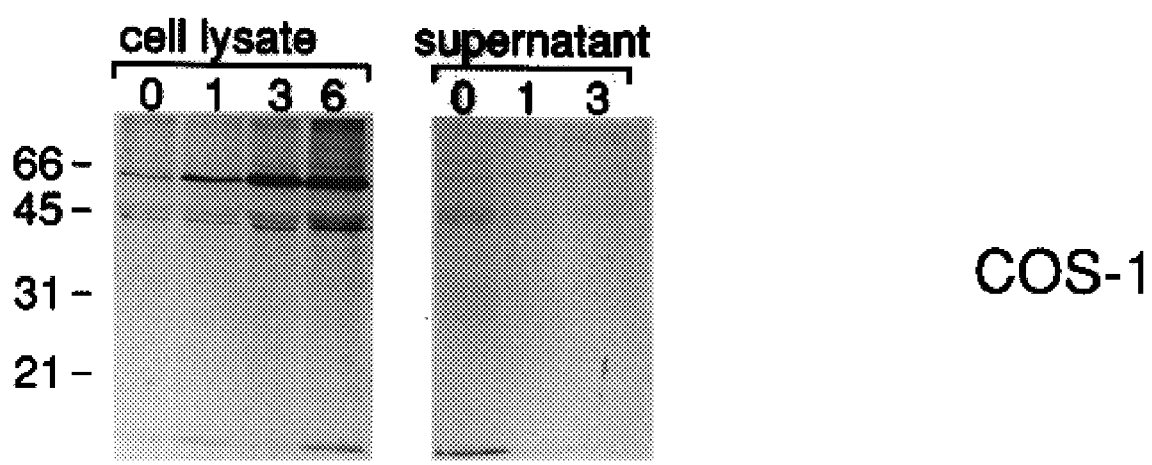

Although KL was purified from conditioned medium of Balb/c 3T3 cells and is a soluble protein, the predicated amino acid sequences for KL-1 and KL-2 suggest that these proteins are membrane-associated. In order to investigate the relationship of KL-S with the KL-1 and KL-2 protein products their biosynthetic characteristics were determined. The KL-1 and KL-2 cDNAs, prepared by RT-PCR, were subcloned into and HindIII and XbaI sites of the expression vectors pcDNAI or pCDM8 for transient expression in COS-1 cells. To facilitate transient expression of the KL-1 and KL-2 protein products COS-1 cells were transfected with the KL-1 and KL-2 plasmids by using the KEAE-dextran/DMSO protocol as described herein. KL protein synthesis in the COS-1 cells was shown to be maximal between 72 to 96 hours subsequent to the transfection. In order to determine the biosynthetic characteristics of the KL-1 and KL-2 proteins pulse-chase experiments were carried out. 72 hours subsequent to transfection, cultures were labeled with $^{35}$S-methionine (0.5 mCi/ml) for 30 minutes and then chased with regular medium. The cell lysate and supernatants then were collected at the indicated times and processed for immunoprecipitation with anti-KL antiserum, prepared by immunizing rabbits with purified murine KL, and analysis by SDS-PAGE (12%). In cells transfected with the KL-1 plasmid, at the end of the labelling period, KL specific protein products of 24, 35, 40 and 45 kD are found (FIG. 21). These proteins presumable represent the primary translation product and processed KL protein products which are progressively modified by glycosylation. Increasingly longer chase times reveal the 45 kD form as the mature KL protein product and it is quite likely that this protein represents the cell membrane form a KL. In the supernatant beginning at 30 minutes a 28 kD KL protein product is seen which, with increasing time, increases in amount. Two minor products of 38 and 24 kD were also found with increasing time. These results are consistent with the notion that KL-1 is first synthesized as a membrane-bound protein and then released into the medium probably through proteolytic cleavage.

A pulse-chase experiment of COS-1 cells transfected with the KL-2 plasmid is shown in FIG. 20. The KL-2 protein products are processed efficiently to produce products of 32 kD and 28 kD which likely include the presumed cell membrane form of KL-2. The cell membrane form of KL-2 is more stable than the corresponding KL-1 protein with a half-life of more than 5 hours. In the cell supernatant, after 3 hours, a soluble form of KL-2 of approximately 20 kD is seen. The appearance and accumulation of the soluble form of KL-2 in the cell supernatant is delayed compared with that of KL-1 in agreement with less efficient proteolytic processing of the KL-2 protein product. In KL-2, as a result of alternative splicing, sequences which include the known C-terminus of the soluble form of KL and thus the presumed cleavage site of KL-1 is missing. Proteolytic cleavage of KL-2, therefore, presumably involves a secondary cleavage site which is present in both KL-1 and KL-2, either on the N-terminal or C-terminal side of the sequences encoded by the deleted exon. A 38 kD KL-1 protein product seen in the supernatant may represent a cleavage product which involves a cleavage site near the transmembrane domain (FIG. 19).

Proteolytic Processing of KL-1 and KL-2 in COS Cells is Modulated by PMS and the Calcium Ionophore A23187

Figure 22A:
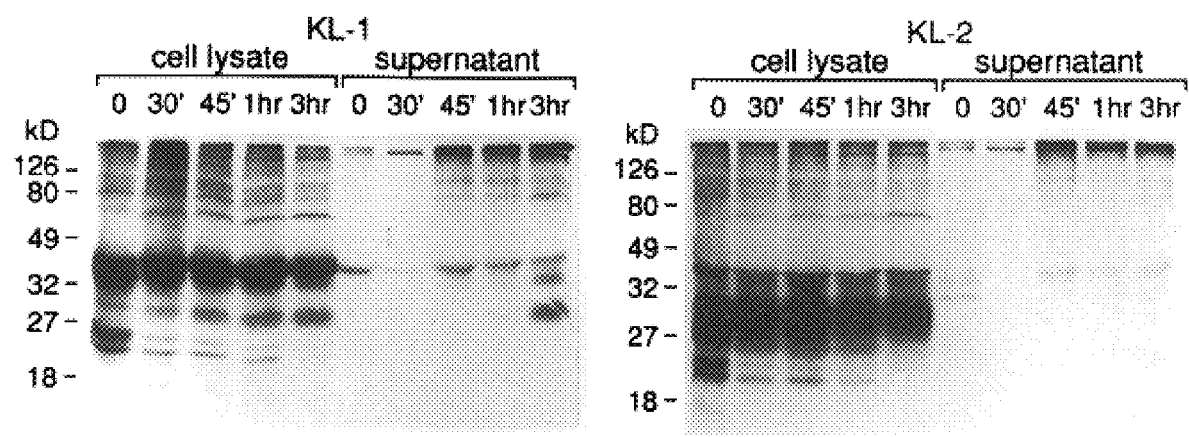
FIGS. 22A–22C. PMA induced cleavage of the KL-1 and KL-2 protein products. COS-1 cells were transfected with 5 $\mu$g of the KL-1 and KL-2 expression plasmids and after 72 hours the cells were labelled with $^{35}$S-Met for 30 minutes and then chased with medium a) in the absence of serum; b)
Figure 22B:
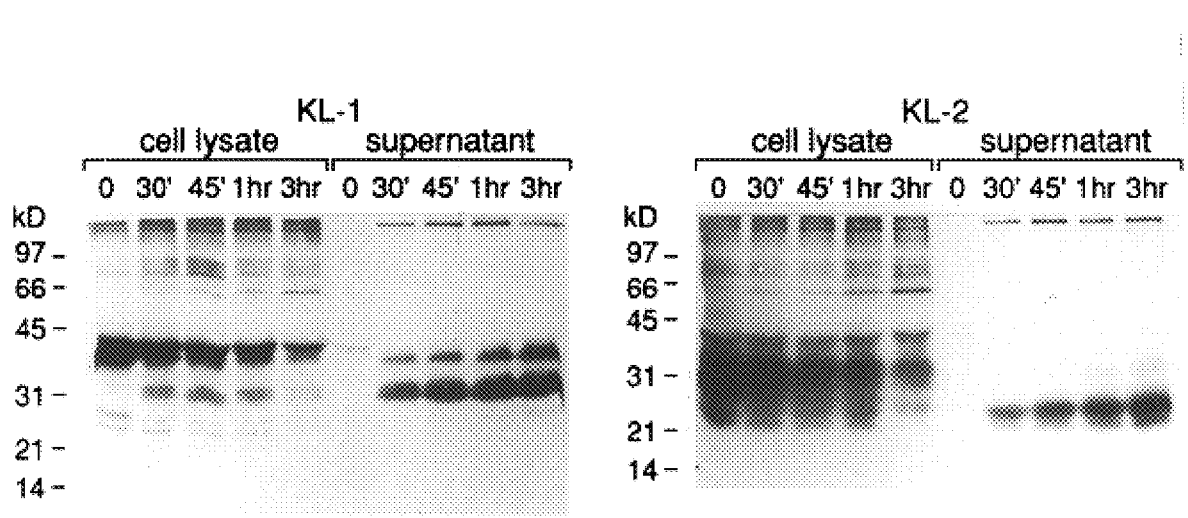
Figure 22C:
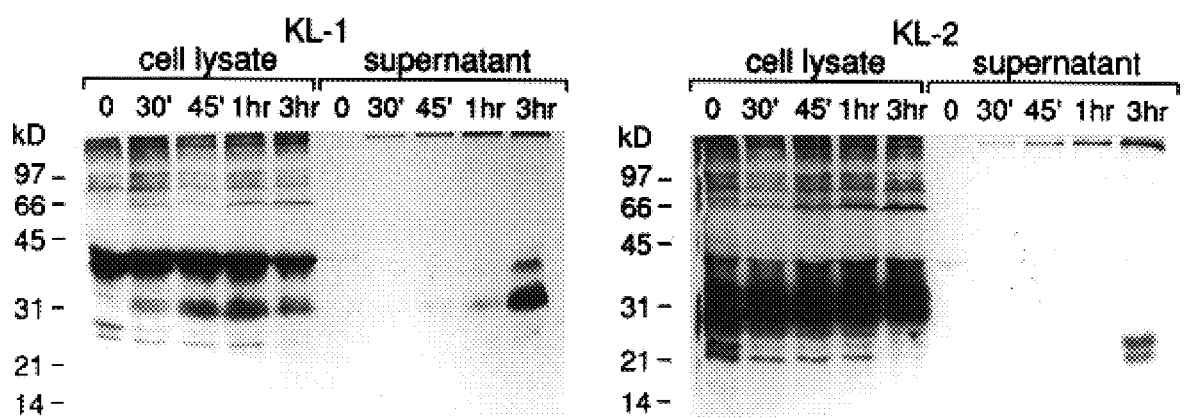

The protein kinase C inducer PMA is known to facilitate proteolytic cleavage of cell membrane proteins to produce soluble forms of the extra-cellular domain of these proteins as shown with the examples of the CSF-1 receptor, the c-kit receptor and TGF-α (13,4). The effect of PMA treatment on the biosynthetic characteristics of KL-1 and KL-2 in COS-1 cells has been determined. The pulse-chase experiments shown in FIG. 22B indicate that PMA induces the rapid cleavage of both KL-1 and KL-2 with similar kinetics and that the released KL-1 and KL-2 protein products are indistinguishable from those obtained in the absence of inducer. These results suggest that the proteolytic cleavage machinery for both KL-1 and KL-2 is activated similarly to PMA. On one hand this may mean that two distinct proteases, specific for KL-1 and KL-2 respectively, are activated by PMA or alternatively, that there is one protease which is activated to a very high level which cleaves both KL-1 and KL-2 but with different rates. The major cleavage site in KL-1 based on the known C-terminal amino acid sequence of rat KL, includes amino acids PPVA A SSL (186–193) and may involve an elastase like enzyme (22,34). The recognition sequence in KL-2, based on the arguments presented above, presumably lies C-terminal of the deleted exon and therefore might include amino acids RKAAKA (202–207) and thus could involve an enzyme with a specificity similar to the KL-1 protease, alternatively, it could be a trypsin-like protease. The effect of the calcium ionophore A23187 on KL cleavage has been determined. Both KL-1 and KL-2 cleavage is accelerated by this reagent indicating that mechanisms that do not involve the activation of protein kinase C can mediate proteolytic cleavage of both KL-1 and KL-2 (FIG. 22C).

Biological Activity of the Released KL Protein Products

To test the biological activity of the released KL protein products, the supernatants of transfected COS-1 cells were collected 72 hours after transfection and assayed for activity in the mast cell proliferation assay. Bone marrow derived mast cells (BMMC) were incubated for 24 hours with different dilutions of the collected supernatants and assayed for $^3$H-thymidine incorporation as described previously (FIG. 23). Supernatants from KL-1 transfectants produced 3 to 5 times more activity than KL-2 transfectants in agreement with the differential release of soluble KL from KL-1 and KL-2. Importantly the proteins released from both the KL-1 and the KL-2 transfectants appeared to display similar specific activities in the mast cell proliferation assay.

The Steel Dickie Allele Results From a Deletion of C-Terminal KL Coding Sequences Including the Transmembrane and the Cytoplasmic Domains Mice homozygous for the Sl$^d$ allele are viable, in contrast to mice homozygous for the Sl allele, although they lack coat pigment, are sterile and have macrocytic anemia. The c-kit receptor system in these mice, therefore, appears to display some residual activity. The $Sl^d$ mutation affects the three cell lineages to similar degrees suggesting that the mutation affects and intrinsic property of KL. Thus, to investigate the molecular basis of $Sl^d$, the KL coding sequences were first characterized in this allele by using PCR cloning technology. Primary embryo fibroblasts from an $Sl^d$/+embryo were derived by standard procedures. RNA prepared from $Sl^d$/+embryo fibroblasts and different primers then were used to amplify the $Sl^d$ KL coding region paying attention to the possibility that $Sl^d$ is a deletion mutation. RT-PCR amplification by using $Sl^d$/+total RNA and primers 1 and 2 produced one DNA fragment that migrated with a mobility identical to that of the product obtained from +/+ fibroblast RNA and sequence determination showed it to be indistinguishable from the known KL sequence. This fragment therefore presumably represented the normal allele. When primers 1 and 3 or 1 and 4 were used a faster migrating DNA fragment was amplified was well (FIG. 18). Both the 850 and 1070 bp DNA fragments obtained with primers 1+3 and 1+4 were subcloned into pCDM8 and then sequenced. In the KL-$Sl^d$ cDNA the segment from nucleotides 660 to 902 of the wild-type sequence is deleted, instead, a sequence of 67 bp was found to be inserted (FIG. 17). The deletion insertion results in a termination codon three amino acids from the 5' deletion endpoint. The predicted amino acid sequence of KL-$Sl^d$ cDNA consists of amino acids 1–205 of the known KL sequence plus 3 additional amino acids (FIGS. 17 and 19). The KL-$Sl^d$ amino acid sequence includes all four N-linked glycosylation sites and all sequences contained in the soluble form of KL, while the transmembrane and the cytoplasmic domains of wild-type KL-1 are deleted. Consequently, the KL-$Sl^d$ protein product is a secreted protein, which displays biological activity.

Biosynthetic Characteristics and Biological Activity of the KL-$Sl^d$ and KL-S Protein Products For comparison with the KL-$Sl^d$ protein product, a truncated version of KL-1 was made, designated KL-S, in which a termination codon was inserted at amino acid position 191 which is the presumed C-terrmimus of the soluble KL protein. COS-1 cells were transfected with the KL-$Sl^d$ and the KL-S plasmids and pulse-chase experiments were carried out to determine the biosynthetic characteristics of the two protein products. The KL-$Sl^d$ protein product is rapidly processed, presumably by glycosylation and then secreted into the medium, where the major 30 kD species is found after as early as 30 minutes of chase time and then increases in amount thereafter (FIG. 24). The biosynthetic characteristics of the KL-S protein products are very similar to those of KL-$Sl^d$ (FIG. 24). Again, with increasing time increasing amounts of secreted material are detected in the medium, conversely the cell associated KL-S protein products decrease with time.

To assess the biological activity of the secreted KL-$Sl^d$ and KL-S protein products, mast cell proliferation assays were performed. The medium from transfected COS-1 cells was collected 72 hours after transfection and then different dilutions were used to assess proliferative potential conferred on BMMC in the absence of IL-3. Both samples contained significant biological activity that exceeded that of KL-1 to some degree (FIG. 23). Taken together, these results demonstrate convincingly, that the KL-$Sl^d$ protein products are secreted and are biologically active.

Experimental Discussion

The demonstration of allelism between c-kit and the murine W locus brought to light the pleiotropic functions of the c-kit receptor in development and in the adult animal and facilitated the identification of its ligand KL. The recent discovery of allelism between KL and the murine steel locus, furthermore provided a molecular notion of the relationship between the W and the Sl mutations which had been anticipated by mouse geneticists based on the parallel and complementary phenotypes of these mutations. The predicated transmembrane structure of KL implicated that, both membrane-associated and soluble forms of KL play significant roles in c-kit function. In this application, experimental evidence for this conjecture is provided.

First, it is shown that the soluble form of KL is generated by efficient proteolytic cleavage from a transmembrane precursor, KL-1. Second, an alternatively spliced version of KL-1, KL-2, in which the major proteolytic cleavage site is removed by splicing, is shown to produce a soluble biologically active form of KL as well, although, with somewhat diminished efficiency. Third, cleavage of KL-1 and KL-2 in COS-1 cells is a process that can be modulated. Fourth, KL-1 and KL-2 are expressed in a tissue-specific manner. Furthermore, the viable $Sl^d$ mutation was shown to be the result of a deletion that includes the C-terminus of the KL coding sequence including the transmembrane domain generating a biologically active secreted form of KL. The phenotype of mice carrying the $Sl^d$ allele provides further support of the concept for a role for both the secreted and the cell membrane—associated forms of KL in c-kit function.

Because of the close evolutionary relationship of c-kit with CSF-1R it was reasonable to predict a relationship between the corresponding growth factors, KL and CSF-1, in regards to both structural and topological aspects. Alternatively spliced forms of CSF-1 mRNAs are known to encode protein products which differ in sequences N-terminal of the transmembrane domain, a spacer segment of 298 amino acids located in between the ligand portion and the transmembrane domain of the protein (43). In addition, alternatively spliced CSF-1 RNA transcripts differ in their 3' untranslated regions (21). Analysis of KL RNA transcripts in several tissues identified an alternatively spliced KL RNA in which, similar to the situation in CSF-1, the spacer between the presumed ligand portion and the transmembrane domain is deleted. Interestingly, the expression of this alternatively spliced RNA product is controlled in a tissue specific manner. A recent comparative analysis of the ligand portions of KL and CSF-1 indicates structural homology between the two proteins based on limited amino acid homology and the comparison of corresponding exons and matching of "exon-encoded secondary structure" (4). Furthermore, the super position o f4 α-helical domains and cysteine residues which form intra-molecular disulfide bonds implies related tertiary structures for the ligand domains of KL and CSF-1; and the homology seen in the N-terminal signal peptides, the transmembrane domains and the intracellular domains of the two proteins may indicate that these domains fullfill important related functions in the two proteins. These results strengthen the notion of an evolutionary relationship and structural homology between KL and CSF-1.

A unique feature of KL is its predicted tripartite structure as a transmembrane protein. Both forms of KL, KL-1 KL-2, are synthesized as transmembrane proteins which are processed by proteolytic cleavage to release a soluble biologically active form of KL; although, the processing step in the two forms follows differing kinetics, as determined in the COS cell system. Proteolytic cleavage of the KL-1 protein is very efficient, in contrast, the KL-2 protein is more stable or resistant to proteolytic cleavage. The sequences encoded by the deleted exon, amino acids 174–201 include the C-terminus of the soluble KL-2 protein and the presumed proteolytic cleavage site (27). A secondary or alternate proteolytic cleavage site is therefore presumably being used to generate the soluble KL-2 protein and this cleavage might involve another protease. The induction of proteolytic cleavage of KL-1 and KL-2 in COS-1 cells by the protein kinase C activator PMA and by the calcium ionophore A23187 suggests that in different cell types this process may be subject to differential regulation. Interestingly, the soluble KL-2 protein displays normal biological activity indicating that the sequences encoded by the deleted exon are not essential for this activity.

On one hand, KL-1 and KL-2 in their membrane associated versions may function to mediate their signal by cell-cell contact or, alternatively, they might function as cell adhesion molecules (19, 26). On the other hand, the soluble forms of KL are diffusible factors which may reach the target cell and its receptor over a relatively short or longer distances. But the soluble forms of KL might also become associated with, or sequestered in the extracellular matrix, in an analogous fashion to FGF, LIF or int-1, and thus function over a short distance similar to the membrane-associated form (8,33,42). When the cell membrane-associated, KL may be able to provide or sustain high concentrations of a localized signal for interaction with receptor-carrying target cells. In turn the soluble form of KL may provide a signal at lower and variable concentrations. c-kit is thought to facilitate cell proliferation, cell migration, cell survival and post-mitotic functions in various cell systems. By analogy with the CSF-1 receptor system, the cell survival function and cell migration might require lower concentrations of the factor than the cell proliferation function (55). The cell membrane-associated and the soluble forms of KL then may serve different aspects of c-kit function. Both the CSF-1 receptor and c-kit can be down-regulated by protein kinase C mediated proteolytic release of the respective extracellular domains (13). The functional significance of this process is not known but it has been hypthesized that the released extracellular domain of these receptors may neutralize CSF-1 and KL, respectively, in order to modulate these signals. In some ways proteolytic cleavage of KL results in a down modulation of c-kit function and the processes, therefore, may be considered as complementary or analogous. In summary, the synthesis of variant cell membrane-associated KL molecules and their proteolytic cleavage to generate soluble forms of KL provide means to control and modulate c-kit function in various cell types during development and in the adult animal.

A unique opportunity to evaluate the role of the soluble form of KL during development and in adult animals was provided through the characterization of the molecular basis of the $Sl^d$ mutation. The $Sl^d$ allele encodes a secreted version of the KL protein and no membrane associated forms as result of a deletion which includes the transmembrane domain and the C-terminus of KL. The biological characteristics of $Sl^d/Sl^d$ and $Sl/Sl^d$ mice, therefore should give clues about the role of the soluble and the membrane-associated forms of KL. $Sl/Sl^d$ mice produce only the $Sl^d$ protein, since the Sl allele is a KL null-mutation (11,38). These mice are viable and are characterized by a severe macrocytic anemia, lack of tissue mast cells, lack of coat pigmentation and infertility. In most aspects of their mutant phenotype, these mice resemble $W/W^v$ mice (47,51). However some significant differences exist. The anemia of $Sl/Sl^d$ mice appear to be more sensitive to hypoxia than $W/W^v$ mice (46,47). In regards to gametongenesis in $W/W^v$ mice primordial germ cells do not proliferate, and their migration is retarded (32). In $Sl/Sl^d$ embryos primordial germ cells similar to $W/W^v$ embryos do not proliferate, however the remaining cells appear to migrate properly and they reach the gonadal ridges at the appropriate time of development (29,51). From these experiments one might hypothesize that the $Sl^d$ KL protein product is able to sustain cell migration but not cell proliferation and consequently the cell membrane form of KL therefore may play a critical role in the proliferative response of c-kit. Furthermore, $Sl/Sl^d$ fibroblasts do not support the proliferation and maintenance of bone marrow mast cells in the absence of IL-3, in contrast to normal embryo fibroblasts which have this property (16). Provided that the $Sl/Sl^d$ fibroblast indeed synthesize the $Sl^d$ protein products, the inability of the $Sl/Sl^d$ fibroblasts to support the proliferation of mast cells, on one hand, may indicate that the amount of soluble $KL$-$Sl^d$ protein which is released by these cells is not sufficient to facilitate proliferation; on the other hand, these results may suggest that there is a critical role for the cell membrane associated form of KL in this process.

KL in Combination with IL-1, IL-3, G-CSF, GM-CSF

We have used murine KL (recombinant murine c-kit ligand) in normal murine bone marrow cultures and observed very few myeloid colonies stimulated with KL alone, but a substantial increase in both colony number and size was seen with combinations of KL and G-CSF, GM-CSF, and IL-3, but not with M-CSF (103). In HPP-CFC assays using marrow 24 hours post 5-FU treatment, increasing colony stimulation was seen with combinations of cytokines. KL plus either G-CSF, GM-CSF, IL-3, IL-7, or IL-6 was effective and combinations of three or four factors were even more effective in stimulating HPP-CFC, CSF's or IL-3 combined with IL-1, IL-6, and KL were maximally effective. FIG. 25 shows HPP-CFC stimulated by cytokine combinations in cultures of 4-day post 5-FU murine marrow. In dual cytokine combinations, IL-1 plus GM-CSF or IL-3 stimulated comparable numbers of HPP-CFC, as did KL plus IL-1 or KL plus IL-3, but three factor combinations of IL-1 plus KL and either G-CSF, or IL-3 were maximally effective.

Delta or secondary CFU assay for early hematopoietic cells: Murine studies. The delta assay involves the short-term (7-day) suspension culture of bone marrow depleted of committed progenitors and enriched for early stem cells in the presence of various cytokines to promote survival, recruitment, differentiation, and expansion of stem cells and progenitor cells is measured in a secondary clonogenic assay. 5-FU-resistant stem cells are assayed in a primary HPP-CFC assay multiple cytokine stimuli as well as in conventional CFU-GM assays with single CSF stimuli. After suspension culture secondary HPP-CFC and CFU-GM assays are performed. Three parameters are routinely measured. First is the amplification of lineage-restricted progenitors determined by the total CFU-GM responsive to a single CSF species (eg, G-CSF) in the primary culture (input) divided into total number of secondary CFU-GM responsive to the same CSF species in the secondary culture (output). Second is the ratio of HPP-CFC input divided into the total number of CFU-GM progenitors in the secondary assay. Because the CFU-GM are presumed to derive from earlier precursors, i.e., HPP-CFC, this ratio gives the indication of stem cell to progenitor cell differentiation. Finally, the ratio of HPP-CFC input divided into the total number of secondary HPP-CFC is determined. This parameter is the best measure of stem cell self-renewal, particularly if the HPP-CFC stimulus is the primary and secondary cultures is a combination of IL-1, IL-3 and KL.

In earlier studies (before the availability of KL), varying degrees of expansion in the number of CFC-GM responsive to single CSF species, and in HPP-CFC-1 and 2, were seen when IL-1 was combined with M-CSF (20- and 30-fold increases), with G-CSF (50- to 100-fold increases), with 200-fold increases) IL-3 and GM-CSF produced a limited degree of progenitor cell expansion whereas M-CSF and G-CSF did not. IL-6 was less effective than IL-1 in synergizing with M-CSF, GM-CSF, or G-CSF but was equally effective in synergizing with IL-3. IL-1 plus IL-6 showed additive or supradditive interactions with the three CSF's and IL-3. When KL (prepared as described herein or alternatively prepared as described in PCT International Publication No. WO 92/00376, entitled "Mast Cell Growth Factor" published on Jan. 9, 1992 and assigned to the Immunex Corporation or alternatively in European Patent Application No 423 980, entitle "Stem Cell Factor" published Apr. 24, 1992 and assigned to Amgen Inc) was present in the suspension culture phase only a minor amplification of progenitor cell production occurred (FIG. 26) but when combined with GM-CSF, IL-3, or IL-1, 200- to 800-fold amplification occurred. The combination of IL-1, KL and either GM-CSF or IL-3 was even more effective in amplifying progenitors, and the four factor combination of IL1+KL+IL-6 with either IL-3 or GM-CSF produced up to 2,500-fold increases in progenitor cells. Calculations of progenitor cell generation based on CFU-GM output. HPP-CFC input showed that three factor combinations (IL-1+KL+IL-3 or CSF's) generated ratios of 6,000 to 10,000 and four factor combinations (including IL-6) generated ratios of 8,000 to 15,000. As measure of self-renewal the generation of secondary HPP-CFC-1 as a ration of HPP-CFC input reached values of 50 to 700 with two factor combinations of KL with IL-1, IL-3 or CFS's and 700 to 1,300 with three factor combinations of IL-1 +KL with IL-6, IL-3, or CSFs.

Based on the total differentiating cells produced in a 7-day culture of enriched HPP-CFC exposed to a combination of IL-1 plus IL-3 plus KL, FIG. 27 illustrates the dramatic proliferation obtained. This includes a self-renewal component measured by secondary HPP-CFC-1 generation, a progenitor cell production measured by low proliferative potential CFU-GM, and morphologically identifiable differentiating myeloid cells. The cell population doubling time required to generate these cells from a single precursor reaches the limits of known mammalian cell proliferation rates. If this proliferative was sustained by an earlier even more infrequent cell than the HPP-CFC, an even shorter population doubling time would be required. The amplification of HPP-CFC in this short-time culture is unlikely to be reflected in a comparable expansion in long-term reconstituting cells, and the majority of HPP-CFC, an even shorter population doubling time would be required. The amplification of HPP-CFC is unlikely to be reflected in a comparable expansion in long-term reconstituting cells, and the majority of HPP-CFC generated are more likely to representative of later stages within the stem cell hierarchy. Assay of D12 CFU-S also showed an absolute increase in numbers after 7 days suspension culture of IL-1 plus IL-3 or KL. Other investigators have shown that in similar suspension cultures, precursors of CFU-GEMM (possibly long-term reconstituting stem cells) also amplified in the presence of IL-1 plus IL-3 but not with IL-6 and IL-3 or GM-CSF combinations.

Delta or secondary CFU assay for early hematopoietic cells: Human Studies. In humans, 4-HC treatment of bone marrow has been shown to deplete the majority of progenitors capable of responding directly to GM-CSF by in vitro colony formation while preserving stem cells capable of colony formation while preserving stem cells capable of hematopoietic reconstitution in the context of bone marrow transplantation. In primitive transplantation studies, CD34$^+$ selection also enriched for marrow cells capable of long-term reconstitution. Following combine 4 -HC treatment and selection of CD34$^+$ cells by immunocytoadherence, primary colony formation in response to G-CSF or GM-CSF was extremely low. However, 7 days of suspension culture followed by secondary recloning with GM-CSF showed that exposure of treated marrow cells for 7 days in suspension to combination of IL-1 and IL-3 consistently generated the highest number of secondary CFU-GM. IL-3 and IL-6 was no less effective than IL-3 alone and other cytokine combinations were significantly less effective. Secondary colony formation in this assay was maximally stimulated by combinations of IL-1 and KL, KL and IL-3, and combinations of all three cytokines was most effective in amplifying progenitor cell generation.

Interactions Between c-kit Ligand (KL) and IL-1S, IL-6 and Other Hematopoietic Factors The in vivo purging of BM with 5-FU is a simple technique for the enrichment of quiescent hematopoietic progenitor cells. A single dose of 5 -FU can, within 24 hours, reduce the numbers of early-appearing CFU-S and the more mature CFU-C populations by greater than 99%, while enriching the BM for more primitive progenitors. Late-appearing CFU-S are also sensitive to BM purging with 5-FU, further suggesting that these cells are not he same as stem cell responsible for long-term BM reconstitution. In contrast, BM reconstituting stem cells have been shown to be refractory to the cytotoxic effects of 5-FU (105). Bradley and Hodgson, using 5-FU purged BM, identified a compartment of progenitor cells, HPP-CFC, that are capable of forming large highly cellular colonies in agar cultures.

We have investigated the interactions of IL-1, IL-6 and KL on primitive murine progenitor cell compartments (104). We present evidence, using clonal cultures, for synergistic and additive effects of these factors alone or in conjunction with CSF's. Our results suggest that IL-1, IL-6 and KL act uniquely in their stimulation of early hematopoiesis. The finding with the clonal cultures are further substantiated using a short-term liquid culture assay, the $^\Delta$-assay, that has been previously described. We demonstrate the ability of IL-1, IL-6 and KL and regulate the expansion of early and late hematopoietic progenitor compartments.

Materials and Methods

Mice. Male and female (C57BL/6X SBA/2)F$_1$ (B 6D2F1) mice were purchased from The Jackson Laboratory (Bar Harbor, Me.). The mice were maintained under laminar-flow conditions, and were provided with acidified and/or autoclaved drinking water. Sentinel mice, housed along with the colony, were observed for specific pathogens. All mice used were of at least 8 weeks of age.

Marrow Preparation and Tissue Culture Conditions. BM from normal (NBM) or 5-FU treated mice was obtained from femora and sometimes tibia of at least 3 mice per experiment. Mice were treated with 5 -FU by intravenous injection of 150 mg/kg in a volume of 150 to 250 µl. BM was washed twice by centrifugation before culturing. Unless otherwise noted, all handling and cultures of BM was done in culture medium containing IMDM (Gibco, Grand Island, N.Y.) supplemented with 20% FCS (HyClone Laboratories Inc., Logan, Utah) and 0.05% mg/ml gentamicin (Gibco). BM cells were enumerated using a Coulter counter model ZBI (coulter Electronics, Hialeah, Fla.). All plasticware used was of tissue culture grade.

Cytokines and Antibodies. Purified rhIL-1β, sp act=1.32× $10_7$ U/mg, (Syntex Laboratories, Inc.,: Palo Alto, Calif.) was used at 100 U/ml. Partially purified and purified rhIL-6 was kindly provided by Steven Gillis (Immunex Corporation, Seattle, wash.); partially purified IL-6 was used at 3000 CESS U/ml and purified IL-6 was used at 500 ng/ml. Purified KL (prepared as described herein or alternatively prepared as described above. Purified rhF-CSF (Amgen Biologicals, Thousand Oaks, Calif.) was used at 100 U/ml (sp act=1×108 U/mg). Purified rhM-CSF was used at 1000 U/ml (Immunex). Conditioned media containing rmIL-3 was prepared from transiently transfected COS-7 cells, and like all other growth factors was used at concentrations resulting in maximal CFU-C stimulation. Rat anti-mouse IL-6 monoclonal antibody was purchased from Genzyme (Cambridge, Mass.).

CFU-C Assay. LPP-CFC was assayed in 35 mm petri dishes containing 1 ml of $5 \times 10_4$ NBM suspended in culture medium containing cytokines and 0.36% agarose (Seaplaque; FMC, Rockland, Me.). Such cultures were incubated for 7 days at 37° C. in a fully humidified 5% CO2 atmosphere. HPP-CFC were assayed using a double-layer agarose system previously described. Sixty mm petri dishes containing a 2 ml underlayer consisting of culture media, cytokines and 0.5% agarose was overlayed with 1 ml of 5 -FU 1 to 8 days prior (d1–d8 5-FU BM) was assayed for HPP-CFC at cell concentrations ranging from $1 \times 10^3$ to $1 \times 10^5$ cells/culture. Double-layer cultures were grown for 12 days at 37° C. in a fully humidified, 5% CO2, and 7%O2 atmosphere. Dishes were scored for low proliferative colonies containing at least 50 cells (LPP-CFC) and highly cellular high proliferative colonies with diameters of at least 0.5 mm (HPP-CFC). All CFU-C were enumerated from triplicate cultures.

CFU-Assay. Mice were irradiated with 1250 Gy from a 137Cs γ-ray source at a dose rate of approximately 90 Gy/minute. The 1250 Gy was given as a split dose of 800 Gy plus 450 Gy separated by 3 hours. BM cells were injected intravenously 2–3 hours after the final irradiation. Late-appearing CFU-5 were counted on spleens fixed in Bouin's solution 12 days after BM transplantation.

Delta ($\Delta$) Assay. Suspension cultures were performed as previously described. Quadruplicate 1 ml $\Delta$-cultures consisting of $2.5 \times 10_5$ d1 5-FU BM cells/ml were established in 24 well cluster plates and incubated in the presence of growth factors for 7 days at 37° C. in fully humidified 5% CO2 atmosphere/ Non-adherent cells from week old cultures were harvested after vigorous pipetting. Resuspended BM cells from quadruplicate $\Delta$-cultures were pooled and 1 ml was used for the determination of culture cellularity. The remaining 3 ml of cells were washed by centrifugation through and underlayer of 5 ml FCS. Washed cells were assayed for secondary LPP-CFC, HPP-CFC and CFU-S. Secondary LPP-CFC responsive to G-CSF, GM-CSF and IL-3 were measured in 7 day CFU-C cultures. Secondary HPP-CFC and LPP-CFC responsive to IL-1 and IL3 were enumerated after 12 days under the conditions described for growth of HPP-CFC. Cell from $\Delta$-cultures were diluted from 20 to 2,000-fold for the determination of secondary CFU-C. The numbers of CFU-S present in $\Delta$-cultures after one week's growth were determined by transplanting mice with 2 to 200-fold dilutions of washed cells.

The fold increases in BM progenitor populations after the $\Delta$-culture has been termed the $\Delta$-value. The numbers of primary LPP-CFC, HPP-CFC and CFU-S present in the staring d1 5-FU BM population were measured in parallel to the suspension cultures. Delta-values were determined by dividing the total output of secondary LPP-CFC, HPP-CFC and CFU-S by the input of primary LPP-CFC, HPP-CFC and CFU-S respectively.

Adherent-Cell Depleted $\Delta$-Assay. Delta-cultures, of 12.5 ml of $2.5 \times 10^5$ d1 5-FU BM cells/ml, were established in 25 $cm^2$ tissue culture flasks. Before the onset of culture, BM was depleted of adherent cell populations by a single 4 hours incubation at 37° C. in culture medium. Non-adherent cells were transferred to a second 25 $cm^2$ flask, and both cell populations were maintained under the conditions described above for $\Delta$-cultures.

Assays for Cytokine Activity. Delta-culture supernatants, from cultures grown in 25 $cm^2$ tissue culture flasks, were collected by centrifugation. Supernatants were collected from cultures established with d1 5-FU BM, adherent cell depleted BM and BM adherent cells. IL-6 activity was measured using the murine hybridoma 9 cell proliferation assay as previously described. Cytokine activity was also measured using the growth dependent hematopoietic cell line NFS-60. Proliferation of NFS-60 cells in response to growth factor activity was measured as previously described.

Statistics. Significance was determined using the two-way paired Student's t-test.

Results

Figure 1:
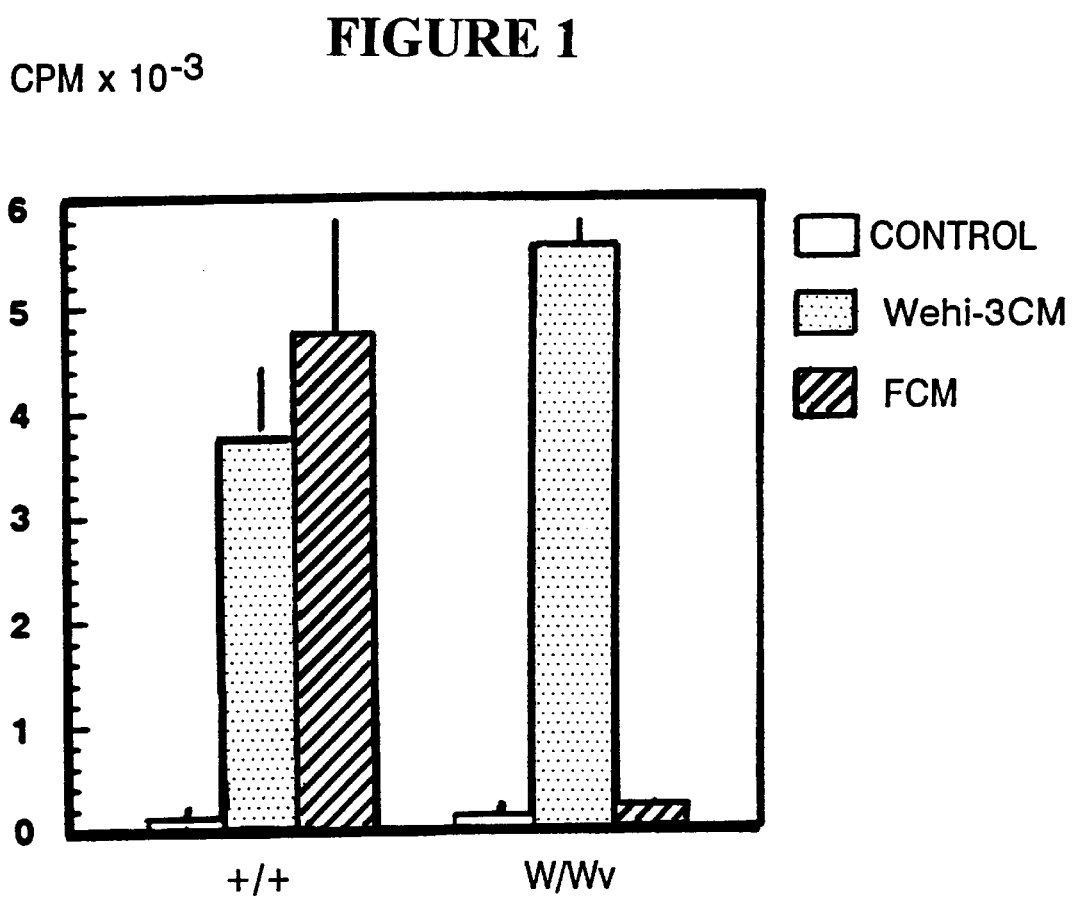
FIG. 1. Proliferative response of +/+ and $W/W^V$ BMMC to fibroblast conditioned medium and IL-3. Mast cells derived from +/+ or $W/W^V$ bone marrow were cultured in the presence of 1% 3 CM, 10% FCM (20× concentrated), or medium alone. Incorporation of $^3$H-thymidine was determined from 24–30 hours of culture.

Activities of IL-1, IL-6, and KL on NBM. The effects of G-CSF, M-CSF, GM-CSF and IL-3 in combination of IL-1, IL-6 and KL on colony formation from NBM is shown in FIG. 1. Colony formation in response to IL-1, IL-6, KL and IL-1 plus IL-6 was minimal. Combining the stimulus of IL-1 with M-CSF, GM-CSF or IL-4 increased colony formation over that observed with the CSF's alone, most notably the greater than additive effects of IL-1 and M-CSF stimulation which was consistently seen in repeated studies. The addition of IL-6 to CSF-containing cultures increased colony formation in an additive fashion. The combined stimulus of IL-1 plus IL-6, alone or in combination with the CSF's, did not noticeably affect colony growth in a greater than additive fashion. The addition of KL to IL-1, IL-6, G-CSF, GM-CSF or IL-3 containing cultures stimulated CFU-C in a synergistic manner. KL did note synergize with M-CSF. The addition of CSF-to IL-1 plus KL or IL-6 plus KL-stimulated cultures demonstrated additive or less than additive colony growth.

Activities of IL-1, IL-6 and KL on 5-FU BM. The recovery of HPP-CFC and LPP-CFC from 1 to 7 days after a single administration of 5-FU to mice is shown in FIGS. 2 and 3. Few colonies grew in response to IL-1 and/or IL-6 stimulation, although several HPP-CFC as well as LPP-CFC were consistently detected. The lineage restricted CSF's , G-CSF and M-CSF, had little ability to stimulate HPP-CFC, whereas GM-CSF and IL-3 were able to stimulate both HPP-CFC and LPP-CFC. The greatest stimulation of HPP-CFC required combinations of growth factors.

Kit-Ligand had almost no detectable colony-stimulating activity, with only an average of 1.3 HPP-CFC and 2.7 LPP-CFC being stimulated from $1 \times 10^4 d7$ 5-FU BM cells (FIG. 30). The concentration of KL used throughout most of this study was 20 ng/ml. This concentration of KL to promote high proliferative colony formation in the presence of IL-1 and IL-6. At 1 ng/ml KL an average of 6.7 colonies were observed, whereas from 10 to 100 ng/ml KL colony numbers reached a plateau in the range of 120 to 147 HPP-CFC per $2.5 \times 10^4$ d4 5-FU BM cells (data not shown). The addition of KL to G-CSF containing cultures resulted in increased numbers of HPP-CSF in d1 5-FU BM as well as increase number of LPP-CFC in both d1 and d7 5-FU BM populations. Synergism among KL and G-CSF in stimulating HPP-CFC was pronounce in cultures of d4 5-FU BM (data not shown). The combination of KL plus M-CSF did not result in any super-additive colony formation. However KL showed strong synergism in stimulating HPP-CFC in the presence of GM-CSF and IL-3. IL-3 plus KL was a more effective stimulus of large colony formation that IL-1 plus IL-3 in both d1 and d7 5-FU BM populations; addition of KL to IL-3 containing cultures increased the numbers of HPP-CFC by 6 to 35 fold in d1 and d7 5-FU BM respectively.

Although IL-1, IL-6 or KL have no appreciable CSF activity, the addition of KL to IL-1, IL-6 or IL-1 plus IL-6 containing cultures results in dramatize synergism among these factors in promoting the growth of HPP-CFC (FIG. 30). Combining KL with IL-6 or IL-1 stimulated an average of 4.0 and 13.7 high proliferative colonies of $1 \times 10^5$ d1 5-FU BM cells respectively. Moreover, in response to all three cytokines an average of 42.0 HPP-CFC per $1 \times 10^5$ cells were stimulated. These results clearly demonstrate the existence of a subpopulation of HPP-CFC that require stimulation of IL-1, IL-6 plus KL for large colony formation. The response of d7 5-FU BM to these growth factor combinations was similar to d1 5-FU BM. However, the proportion of HPP-CFC stimulated with IL-1, IL-6 plus KL in d7 5-FU BM was less than a tenth of the maximum number of HPP-CFC that could be stimulated by the further addition of GM-CSF to this three factor combination. The difference in the d1 5-FU BM population was less dramatic with the maximum number of HPP-CFC stimulated by four cytokines being only a little more than twice the number stimulated by IL-1, IL-6 plus KL.

The addition of IL-6 to cultures containing combinations of KL and CSF's did not enhance large colony formation above the numbers that could be accounted for by the additive effects of two factor combinations of IL-6, KL and CSF (FIG. 30). For instance, the combination of IL-6, KL plus GM-CSF resulted in approximately 30 high proliferative colonies per $1 \times 10^5$ d1 5-FU BM cells. The bulk of these 30 HPP-CFC could be accounted for by the combined number of colonies observed in IL-6 plus KL plus GM-CSF-stimulated cultures (4 and 20 HPP-CFC respectively), suggesting that IL-6, KL plus CSF do not combine to recruit any additional HPP-CFC to proliferative.

In contrast to the above results with IL-6, the addition of IL-1 to cultures containing KL and CSF did demonstrate synergism (FIG. 30). This synergism was most evident in the cultures of d7 5-FU BM grown in combinations of IL-1, KL plus G-CSF. Any two factor combination of these three cytokines stimulated 5 or less HPP-CFC, whereas the combination of IL-1, KL plus G-CSF resulted in an average of 100 HPP-CFC per $1 \times 10^4$ BM cells. Although not as pronounced, synergism was evident among IL-1, KL plus GM-CSF or IL-1 in stimulating d7 5-FU BM. These super-additive effects were also apparent in the d1 5-FU BM population with combinations of IL-1, KL plus G-CSF or M-CSF. The large number of HPP-CFC present in d1 5-FU BM stimulated by combinations of IL-1, KL plus GM-CSF or IL-3 could, however, be attributed to additive effects of these growth factors on different populations of HPP-CFC.

As mentioned above, the greatest number of HPP-CFC were stimulated by combinations of four growth facts, with the stimuli IL-B 1, IL-6, KL plus GM-CSF or IL-3 being optimal (FIG. 30). The combination of IL-1, IL-6, KL plus GM-CSF was capable of stimulating over 3%T of d7 5-FU BM cells to form high proliferative colonies. Only with the cytokine mixture of IL-1, IL-6, KL plus M-CSF did the observed increase in HPP-CFC appear to be due synergism of all four growth factors in promoting additional large colony growth observed with combinations of fewer cytokines. The addition of IL-6 to the cytokine combinations of IL-1, KL plus G-CSF, GM-CSF or IL-3 did not result in superadditive colony formation. The number of high proliferative colonies stimulated by IL-1, IL-6, KL plus G-CSF, GM-CSF, or IL-3 were in most cases, not significantly greater than the number of HPP-CFC stimulated with the combinations IL-1, KL plus G-CSF, GM-CSF, or IL-3.

Expansion of 5-FU BM in $^\Delta$-Cultures. The numbers of non-adherent cells recovered after 7 days of growth in $^\Delta$-cultures reflected the pattern of response observed with various combinations of cytokines in the clonal cultures of 5-FU BM (FIG. 31). Control cultures of d1 5-FU BM receiving no cytokine stimulation had an average 39% decline in culture cellularity, with the predominant surviving cell population being monocyte/marcophage. The addition of IL-1, IL-6 or KL alone did not increase the recovery of cells above the input level. Except for slight increases in response to GM-CSF and IL-3, only those cultures stimulated with multiple cytokines expanded their cell numbers. The greatest proliferation resulted from cultures stimulated with IL-1, KL plus GM-CSF or IL-3, the further addition of IL-6 to these cultures did not increase the recovery of cells significantly. The appearance of immature myeloid cells correlated with the observed proliferation of the $^\Delta$-cultures. In one experiment, IL-3 stimulated cultures contained about 50% mature segmented neutrophils and macrophages, 25% metamyelocytes, 20% myelocyte and 3% blast cells. The percentage of blast cells increase with the addition of IL-1 (22%), IL-6 (18%), KL (24%), IL-1 plus IL-6 (12%), IL-1 plus KL (51%), IL-6 plus KL (43%) and IL-1, IL-6 plus KL (46%) to IL-3 containing cultures. The greatest total number of blast cells, $6.1 \times 10^5$ cells, was recovered from cultures stimulated with IL-1, KL and IL-3, representing on the order of a 200 fold increase over the starting d1 5-FU BM population.

Control $^\Delta$-cultures, grown without the addition of cytokines, did not increase LPP-CFC progenitor cell populations over input values (FIG. 32). Expansion was evident with the addition of the colony-stimulating factors G-CSF, M-CSF, GM-CSF and IL-3 (mean $^\Delta$-values of 3.4, 2.4, 23 and 140 respectively). IL-1 alone stimulated over a sixty-fold increase in LPP-CFC, and combining the stimuli of IL-1 and CSF's resulted in synergistic expansions of LPP-CFC. For example, IL-1 plus IL-3 had a mean $^\Delta$-value of 520 as compared to the predicted additive $^\Delta$-value of 140 (IL-3)+63 (IL1)=203. IL-6 stimulated a small but significant expansion of LPP-CFC ($^\Delta$-value=3.4; p<0.01). Greater than additive effects were evident in the combination of IL-6 plus G-CSF and IL-6 plus IL-3. KL did not significantly increase the recovery of LPP-CFC from $^\Delta$-cultures (p=0.08). The combined stimuli of KL and CSF's was, however, greater than additive in all cases. The combination KL plus IL-3 was as effective as IL-1 plus IL-3 in expanding LPP-CFC (mean $^\Delta$-value=485 and 520 respectively; p=0.21). Delta-cultures stimulated with IL-1 plus IL-6 in combination with CSF's had higher $^\Delta$-values in all cases than cultures stimulated with IL-1 or IL-6. The increased LPP-CFC expansion was additive in all combinations of IL-1, IL-6 plus CSF except in cultures stimulated with IL-1, IL-6 plus M-CSF ($^\Delta$-value=

300, compared to IL-1 plus M-CSF, $^\Delta$value=140, or IL-6 plus M-CSF, $^\Delta$-value=2.8). IL-6 plus KL was synergistic in stimulating the expansion of LPP-CFC over 200-fold, however the addition of these two cytokines to CSF containing cultures resulted in only additive increases in progenitor cells. Together, IL-1 and KL were synergistic in stimulating over a 1,00-fold expansion in LPP-CFC. The addition of G-CSF, GM-CSF or IL-3 to IL-1 plus KL-containing cultures further increased the expansion of LPP-CFC (mean $^\Delta$-values of 1100, 1200 and 1400 respectively). The greatest expansion of LPP-CFC was achieved with combinations of IL-1, IL-6, KL plus CSF's. Delta-cultures stimulated with IL-1, IL-6, KL plus IL-3 had over and 1,800-fold expansion of LPP-CFC. Although increasing the $^\Delta$-values, the addition of IL-6 to IL-1 plus KL containing $^\Delta$-cultures did not significantly add to the observed progenitor cell expansion p>0.05).

Expansion of HPP-CFC in $^\Delta$-Cultures. The ability of different cytokine combinations to stimulate the expansion of HPP-CFC was tested (FIG. 33). As was the case with the expansion of LPP-CFC, the greatest increases in HPP-CFC evident in $^\Delta$-cultures stimulated with the combinations of IL-1, KL plus CSF. Alone, the CSF's stimulated only a modest increase in HPP-CFC. IL-6 stimulated an increase in HPP-CFC, furthermore the combined stimulation of IL-6 plus IL-3 was more effecting in expanding HPP-CFC than IL-3 alone. In contrast to IL-6, IL-1 demonstrated synergism in combination with all four CSF's. KL, in combination with all four CSF's, also stimulated the expansion of HPP-CFC in a greater than additive fashion. The combination of IL-1 plus IL-6, with or without CSF's, was more effective in expanding HPP-CFC than either IL-1 or IL-6 alone. The clearest case of synergism using IL-1 plus IL-6 was in combination with M-CSF (mean $^\Delta$-values of 1.0 with IL-6+M-CSF, 13.2 with IL-1+M-CSF and 65.7 with IL-1+IL-6+m-csf). The addition of IL-1 or IL-6 to $^\Delta$-cultures containing KL, alone or in combination with CSF's resulted in greater than additive increase in HPP- CFC. Although increasing the $^\Delta$-values in each case, the addition of CSF's to cultures containing KL with either IL-2 or IL-6 did not significantly increase the expansion of HPP-CFC. The greatest expansion of HPP-CFC was in cultures stimulated with IL-1, IL-6 plus KL ($^\Delta$-value of 705).

Secondary HPP-CFC produced in $^\Delta$-cultures are routinely assayed in clonal assays stimulated with IL-1 plus IL-3 (FIG. 33). Other combination of cytokines, such as IL-1 plus GM-CSF or IL-1 plus M-CSF, have been tested for their ability to stimulate secondary HPP-CFC. The enumeration of secondary HPP-CFC grown in the presence of IL-1 plus M-CSF or GM-CSF was hindered due to the abundance of secondary LPP-CFC, relative to the number of HPP-CFC, stimulated by these cytokine combinations. The effectiveness of IL-1 and KL as a stimulus for secondary HPP-CFC was also tested (FIG. 34). In contrast to any other combination of cytokines tested, IL-1 plus KL-responsive progenitor cells did not expand dramatically in $^\Delta$-cultures that did stimulate the expansion of IL-1 plus IL-3-responsive HPP-CFC and LPP-CFC.

Expansion of CFU-S in $^\Delta$Cultures. In an effort to further characterize the populations of BM cells that emerge after $^\Delta$-cultures, we examined the increase in CFU-S in response to cytokine stimulation in $^\Delta$-cultures (FIG. 35). Cultures grown in the presence of IL-1, IL-3, IL-1 plus IL-3 or IL-3 plus KL demonstrated increases in HPP-CFC and LPP-CFC consistent with the results presented in FIGS. 32 and 33. These cultures also exhibited increases in CFU-S that were greater than the increases in HPP-CFC. IL-1 plus IL-3 and IL-1 plus KL stimulated over 100-fold expansion in the number of late-appearing CFU-S. These results were compared to the expansion of HPP-CFC and CFU-S that are known to occur in mice recovering from 5-FU treatment; the in vivo expandion ($^\Delta$ in vivo) was measured by dividing the total femoral HPP-CFC, LPP-CFC and CFU-S in d8 5-FU BM by the total numbers of colonies observed per d1 5-FU femur. The in vivo expansion of progenitor cells was similar to that observed in in vitro $^\Delta$-cultures, with the exception that the increase in LPP-CFC in vivo was less than those observed in vitro.

DISCUSSION

These studies substantiate the roles of IL-1, IL-6 and KL as regulators of primitive hematopoietic cells. Alone, these cytokines have a limited ability to stimulate the proliferation of murine hematopoietic progenitor cells in our clonal culture assays (FIGS. 29–30). However, synergism among IL-1, IL-6 and KL was evident in the stimulation of colony growth. By systematic analysis in combinations of IL-1, IL-6, KL plus colony-stimulating factors we were able to discriminate populations of HPP-CFC and LPP-CFC present in 5-FU purged BM. The ability of IL-1, IL-6 and/or KL to regulate colony formation by primitive hematopoietic cells was also supported by experiments employing short-term liquid cultures of d1 5-FU BM. The $^\Delta$-assay, which is capable of measuring the flux in progenitor populations in response to cytokine stimulation, demonstrated that the greatest expansion of LPP-CFC and HPP-CFC was dependent upon the synergistic interactions of IL-1, IL-6, KL and CSF's on early hematopoietic progenitors (FIGS. 32–35).

The importance of IL-1 as a regulator of early hematopoiesis has been known since its identification as the synergistic activity, Hemopoietin-1, present in the conditioned medium of the bladder carcinoma cell line 5637. Consistent with previously reported results, we have shown IL-1 to synergize with G-CSF, M-CSF GM-CSF, IL-1 or KL in the stimulation of HPP-CFC (FIGS. 29 and 30). The ability of IL-1 to promote the proliferation of primitive hematopoietic cells was also observed in the $^\Delta$-assay (FIGS. 31–33). The synergistic activity of IL-1, in combination with G-CSF, M-CSF, GM-CSF, IL-3 or KL, was manifest in its ability to promote the expansion of the total number of cells, the number of myeloid blast cells, the number of LPP-CFC and the number of HPP-CFC in liquid culture. Several studies have suggested that the cytokine combination IL-1 plus IL-3 G-CSF, M-CSF, GM-CSF. In $^\Delta$-cultures, the stimulus IL-1 plus IL-3 was capable of expanding LPP-CFC and HPP-CFC by 520 and 83-fold respectively, this expansion of progenitor populations was greater than those stimulated by IL-1 plus G-CSF, M-CSF or GM-CSF. However, the synergism observed between IL-1 and KL was a more effective stimulus than IL-1 plus IL-3 in the expansion of d1 5-FU BM.

Delta-cultures stimulated with IL-1 plus KL increased the number of LPP-CFC by over 1000-fold and the number of HPP-CFC by 280 fold.

The hematopoietic activities of IL-6 were found to differ from those of IL-1. The combinations IL-6 plus IL-3 or KL were found to be synergistic in the stimulation of HPP-CFC from d1–d7 5-FU BM (FIG. 30). IL-6 and KL were also synergistic in the stimulation of CFU-C from NBM (FIG. 28). In the $^\Delta$-assay, synergism was evident between IL-6 and either IL-3 or KL in the expansion of LPP-CFC and HPP-CFC (FIGS. 5 and 6). IL-6 plus IL-3 was not as effective as IL-1 plus IL-3 in the expansion of HPP-CFC ($^\Delta$-values=40 and 83 respectively). The three factor combination of IL-1, IL-6 and M-CSF was found to be synergistic in stimulating HPP-CFC from d1–d7 5-FU BM. Furthermore, the $^\Delta$-assay also demonstrated synergism in the expansion of LPP-CFC and HPP-CFC populations in response to IL-1, IL-6 plus M-CSF. The cytokine combination of IL-1, IL-6 plus KL was synergistic in stimulating the growth of HPP-CFC from d1 and d7 5-FU BM. The addition of IL-1, IL-6 plus KL to $^\Delta$-cultures also resulted in the greatest observed expansion of HPP-CFC ($^\Delta$-value=705). These patterns of synergistic interactions among IL-1, IL-6, KL and CSF's demonstrate the unique roles of IL-1, IL-6 and KL in the regulation of pluripotential hematopoietic progenitors.

The stimulatory effects of KL upon early hematopoietic progenitors observed in this study are in accord with the stem cell growth activity that was instrumental in the cloning of the KL gene. The response of NBM progenitors to IL-1, IL-6, G-CSF, GM-CSF or IL-1 demonstrated synergism in combination with KL (FIG. 28). As previously reported, KL did not enhance colony formation in response to M-CSF from NBM. The same pattern of response was observed using 5-FU BM; KL was synergistic with IL-1, IL-6, G-CSF, GM-CSF or IL-3, but not with M-CSF (FIG. 30). The dramatic synergism in the stimulation of HPP-CFC observed with IL-1 plus KL could be further augmented by the addition of CSF's. Most notable was the synergism observed among IL-1, KL and G-CSF in cultures of d1 and d7 5-FU BM. The optimal hematopoietic response was observed with the four cytokine combinations of IL-1, IL-6, KL plus CSF. Only with the combination of IL-1, IL-6, KL plus M-CSF was the four growth factor stimulation of HPP-CFC synergistic. The combinations IL-1, IL-6, KL plus GM-CSF or IL-3 stimulated the most HPP-CFC, the greatest proliferation of cells in $^\Delta$-cultures and the largest expansion of LPP-CFC in $^\Delta$-cultures (FIGS. 31–33). These results demonstrate the importance of KL in the regulation of the proliferation of early hematopoietic cells.

HPP-CFC represent a hierarchy of cells that can be distinguished based on their growth factor requirements and/or physical separation techniques. The identification of two compartments of early hematopoietic cells, HPP-CFC-1 and HPP-CFC-2, correlates with the separation of progenitor cells based on their retention of the mitochondrial dye rhodamine-123. Rhodamine-123 dull cells represent the more primitive HPP-CFC-1 compartment of cells that require the synergistic interactions of IL-1, IL-3 and M-CSF for their proliferation, whereas the HPP-CFC-2 compartment of cells do not require stimulation by IL-1. The more primitive nature of IL-1 plus CSF stimulated progenitor cells is in agreement with the synergistic interaction observed with IL-1 and CSF's in the expansion of LPP-CFC and HPP-CFC in the $^\Delta$-assay (FIGS. 32 and 33). Furthermore, the regulation of primitive hematopoietic cells is also governed by the growth factors IL-6 and KL. The ability of IL-6 and KL to expand HPP-CFC in $^\Delta$-cultures is suggestive of their role in the stimulation of progenitor cells that are considered to be HPP-CFC-1. These data support the contention that quiescent stem cells, that are spared by 5-FU purging of BM, require stimulation by multiple growth factors for their proliferation. The maturation of these progenitor cells, from HPP-CFC-1 to HPP-CFC-1, is followed by a restriction in the requirement for multiple-cytokine stimulated proliferation. Consistent with the concept of a hierarchy of HPP-CFC is the observation that over 3% of d7 5-FU BM cells are capable of forming HPP-CFC in response to IL-1, IL-6, KL plus GM-CSF stimulation (FIG. 30), an incidence far higher than the estimate frequency of totipotential stem cells present in the BM.

The increase of HPP-CFC in $^\Delta$-cultures is suggestive of an expansion of multipotential hematopoietic progenitors. However, the placement of these post $^\Delta$-culture HPP-CFC in the hierarchy of HPP-CFC is unclear. The observed increases in late-appearing CFU-S in $^\Delta$-cultures supports the contention that the number of multipotential hematopoietic progenitors are expanded under the conditions of the $^\Delta$-assay (FIG. 35). CFU-S were increased over 100-fold in response to IL-1 plus IL-3 or KL plus IL-1 or IL-3 stimulated suspension cultures of purified rhodamine-123 bright or dull progenitor cells. Our results are contrary to the reported decline in CFU-S in liquid cultures of D5 5-FU BM stimulated wit IL-6 plus IL-3 or KL may be more advantageous in gen therapy protocols. Our results also suggest that the expansion of progenitor cells with the cytokines IL-1 plus IL-3 or KL may be beneficial in bone marrow transplantation protocols. HPP-CFC responsive to IL-1 plus KL were minimally expanded by combinations of the growth factors IL-1, IL-3, IL-6 and KL in $^\Delta$-cultures (FIG. 34). The ability of IL-1 plus KL to promote the growth of HPP-CFC from 5-FU BM as well as stimulate large increases in progenitor cells in the $^{66}$-assay is indicative of the ability of IL-1 plus KL to act upon a pool or primitive multipotential progenitors. The limited expansion of IL-1 plus KL responsive HPP-CFC is suggestive of a limited ability of the growth factors IL-1, IL-3, IL-6 and KL to stimulate the self-renewal of early hematopoietic progenitors and stem cells in the $^\Delta$-assay.

IL-1 and KL Induced Proliferation and the Influence of TGP$\beta$ and MIP1$\alpha$ TGF$\beta$ and MIP1$\alpha$ Macrophage Inflammatory Protein-1$\alpha$ have been previously reported to inhibit progenitors. Such reports have suggested that either of these cytokines might act as a negative regulator of hematopoietic stem cell proliferation, although the two have not previously been compared directly in recognized stem cell assays. The murine HPP colony assay assesses stem cell properties by depleting later progenitors with 5-fluorouracil and scoring only colonies with high proliferative potential as assessed by size (>0.5 mm). IL-1 and KL preferentially stimulate early hematopoietic progenitors. We therefore chose to evaluate the effects of TGF$\beta$ and MIP1$\alpha$ on HPP proliferation induced by IL-1 and KL. Results from two separate experiments, each performed in triplicate, are expressed as HPP colony numbers induced by the growth factor combinations shown relative to those induced by GM-CSF (GM) alone:

|  | GM | IL-1 + GM | KL + GM | IL-1 + KL + GM | IL-1 + KL |
|---|---|---|---|---|---|
| Control | 1.0 ± .1 | 7.0 ± 1.3 | 3.9 ± .8 | 47.3 ± 6.5 | 9.7 ± 1.5 |
| TGFB1 | 1.2 ± .2 | 1.3 ± 0.5 | 1.4 ± .2 | 2.0 ± 0.2 | 0 ± 0 |
| TGFB3 | 1.0 ± .2 | 1.3 ± 0.1 | 1.1 ± .3 | 1.4 ± 0.2 | 0 ± 0 |
| MIP1α | 0.9 ± .2 | 6.9 ± 0.7 | 6.3 ± .6 | 50.8 ± 6.5 | 15.8 ± 2.1 |

(TGF$\beta$1 and TGF$\beta$3: 10 ng/ml; MIP1$\alpha$: 200 ng/ml) (Means±S.E.M.)

These results demonstrate that TGF$\beta$ abrogates the synergistic proliferation of HPP colonies promoted by IL-1 and/or KL with GM-CSF, whereas MIP1$\alpha$ has no such effect. Furthermore TGF$\beta$ eliminated HPP colonies induced by IL-1+k1, whereas MIP1$\alpha$ actually promoted HPP colony formation under these conditions. We conclude that TGF$\beta$, but not MIP1$\alpha$, acts as a negative regulator of the hematopoietic progenitor populations assessed here. This has important implications for the design of chemotherapy protection protocols.

Human Studies of KL in Combination with IL-3, EPO or GM-CSF 11 patients with Diamond Blackfan Anemia, all prednisone resistant or requiring high doses, had decreased mean BFU-E frequency with rhEpo and rhIL-3 stimulation. With the exception of one prednisone sensitive patient, these values were below the 95% confidence limit obtained from 4 normal adult bone marrows. When recombinant murine cKit ligand (rmKL) was either added to or substituted for rhIL-3 all patients showed significant increase in BFU-E size and hemoglobinization. Moreover, the combination of rhEPO, rhIL-3 and rmKL at least double mean BFU-E frequency in 8 or 11 patients (range: 2 to 16 fold). RhIL-3 induced myeloid colonies were also decreased to <95% confidence limit in 5 of the 11 patients. The addition of KL increased mean myeloid colony frequency 2 fold or greater in 6 patients.

BFU-E stimulated with rhEpo plus rhIL-3 and/or rmKL were undetectable in 6 Fanconis Anemia patients with various degrees of bone marrow insufficiency. Myeloid colonies were also undetectable in 4 cases, and significantly decreased in 2 with either rhIL-3 or rhGM-CSF stimulation. The addition of rmKL or rhIL-3 increased mean frequency in the latter. RhIL3 plus rmKL induced myeloid colonies in a third patient with DC, one with more sever aplasia had no erythroid or myeloid colonies with either rhIL-3 or rhGM-CSF alone or with rmKL, the second patient had a decreased mean BFU-E frequency with rhEpo and rhIL-3 (13% of normal control). BFU-E from the latter patient increased in size, hemoglobinization and number with the addition of rmKL. RhIL-3 or rhGM-CSF-stimulated myeloid colonies were slightly decreased and KL induced an appropriate increase in mean colony frequency.

Interaction Between c-Kit Ligand (KL) GM-CSF and Tumor NECROSIS Factorα in the Development of Human Pre-Dendritic and Dendritic Cells Dendritic cells are the most potent antigen-presenting cells for induction of primary antigen specific T cell responses in vivo and in vitro. Dendritic cells generated in vitro could be used after antigen pulse for an immunization boost in the context of vaccine therapy against HIV and tumors. We have developed an in vitro systems for generation of human dendritic cells from CD34+ populations of human marrow, peripheral blood and cord blood. Here, the presence of GM-CSF and TNF alpha are necessary for dendritic differentiation in suspension culture and clonogenic assay and c-kit ligand synergistically increases the numbers of dendritic cells/dendritic cell colonies. Table 3a, shows that with adult human marrow CD÷+ cells in clonogenic assay KL is absolutely required for the development of dendritic cell colonies in synergy with GM-CSF and TNFα. In blood CD34+ populations GM-CSF plus TNFα alone induced dendritic cell colony formation but the frequency of colony formation was increased by addition of KL (Table 3b) Comparison of multiple cytokines shows that dendritic colony cell generation was maximally stimulated by a combination of KL, GM-CSF and TNFα (Table 3c). In suspension culture systems, IL-1+KL+IL-3 expanded pre-dendritic cells over one hundred fold in 14 days and with addition of GM-CSF+KL+TNF these cells differentiated to dendritic cells capable of antigen presentation in the context of an allogeneic mixed leukocyte reaction and CD3 T lymphocyte mitogenesis. KL provided a unique amplifying stimulus for the generation of pre-dendritic and dendritic cells for primitive bone marrow progenitors/stem cells.

TABLE 3a

DENDRITIC CELL DIFFERENTIATION OF BONE MARROW CD34+ CELLS IN CLONOGENIC ASSAY
COLS/$10^5$

| STIMULUS | DENDRITIC COLS | MYELOID COLS |
|---|---|---|
| IL-1 + KL + IL-3 + Epo | 0 | 2,567 ± 312 |
| GM-CSF | 0 | 0 |
| GM-CSF + 1.0 ng TNFα | 0 | 83 ± 17 |
| GM-CSF + 2.5 ng TNFα | 0 | 100 ± 15 |
| GM-CSF + 5.0 ng TNFα | 0 | 50 ± 0 |
| GM-CSF + 10.0 ng TNFα | 0 | 50 ± 0 |
| GM-CSF + KL | 0 | 83 ± 17 |
| GM-CSF + KL + 1.0 ng TNFα | 230 ± 12 | 103 ± 4 |
| GM-CSF + KL + 2.5 ng TNFα | 312 ± 10 | 155 ± 6 |
| GM-CSF + KL + 5.0 ng TNFα | 175 ± 12 | 100 ± 8 |
| GM-CSF + KL + 10.0 ng TNFα | 150 ± 30 | 50 ± 10 |

CD34+ cell isolated by immunomagnetic bead separation from normal human bone marrow mononuclear cell fractions. IL-1, KL, IL-3 and GM-CSF used at 10 ng/ml. Cells plated at $2 \times 10^3$ cells/ml and scored for dendritic cell colonies after 14 days.

TABLE 3b

DENDRITIC CELL DIFFERENTIATION OF CORD BLOOD CD34+ CELLS IN CLONOGENIC ASSAY
COLS/$10^5$

| STIMULI | DENDRITIC | MYELOID/ ERYTHROID |
|---|---|---|
| IL-1 + IL-3 + kl + Epo | 0 | 4,817 ± 180 |
| GM-CSF | 0 | 0 |
| GM-CSF + TNFα 1.0 ng | 650 ± 45 | 217 ± 15 |
| GM-CSF + TNFα 2.5 ng | 907 ± 23 | 160 ± 15 |
| GM-CSF + TNFα 5.0 ng | 840 ± 40 | 93 ± 4 |
| GM-CSF + TNFα 10.0 ng | 1,067 ± 44 | 0 ± 0 |
| GM-CSF + KL | 0 ± 0 | 683 ± 44 |
| GM-CSF + KL + TNFα 1.0 ng | 1,995 ± 126 | 855 ± 54 |
| GM-CSF + KL + TNFα 2.5 ng | 2,288 ± 57 | 762 ± 18 |
| GM-CSF + KL + TNFα 5.0 ng | 2,320 ± 61 | 580 ± 15 |
| GM-CSF + KL + TNFα 10.0 ng | 2,597 ± 117 | 570 ± 26 |

CD34+ cells isolated by immunomagnetic bead separation and cultured at $10^3$ cells per ml in IMDM+20% fetal calf serum and 0.36% agarose for 14 days. Dendritic cell colonies identified by morphology at day 14. rhKL, rhIL-3 and rhGM-CSF used at 10 ng/ml.

TABLE 3c

DENDRITIC CELL DIFFERENTIATION OF CORD BLOOD CD34+ CELLS IN CLONOGENIC ASSAY
COLS/$10^5$

| STIMULI | DENDRITIC | MYELOID |
|---|---|---|
| IL-1 + KL + IL-3 | 0 | 13,767 ± 842 |
| GM-CSF | 0 | 1,233 ± 240 |
| G-CSF | 0 | 1,100 ± 327 |
| IL-3 | 0 | 1,833 ± 393 |
| M-CSF | 0 | 67 ± 33 |
| PIXY (GM-CSF/IL-3) | 0 | 2,500 ± 208 |
| GM-CSF + KL | 0 | 7,233 ± 120 |
| G-CSF + KL | 0 | 6,500 ± 666 |
| M-CSF + KL | 0 | 7,400 ± 680 |
| PIXY + KL | 608 ± 103 | 2,467 ± 350 |
| GM + KL + TNFα 10 ng | 8,214 ± 162 | 7,492 ± 800 |
| G + KL + TNFα 10 ng | 1,040 ± 40 | 2,053 ± 40 |
| IL-3 + KL + TNFα 10 ng | 985 ± 182 | 2,427 ± 80 |
| M-CSF + KL + TNFα 10 ng | 413 ± 20 | 5,582 ± 1,030 |
| PIXY + KL + TNFα 10 ng | 1,047 ± 64 | 4,186 ± 254 |

CD34+ cells isolated by immunomagnetic bead separation and cultured at $10^3$ cells per ml. rhKL, rhIL-3, rhGM-CSF, rhG-CSF rhM-CSF and rhPIXY used at 10 ng/ml. Dendritic cells identified by morphology at day 14.

References

1. Aaronson, S. A. and Todaro, G. (1968) J. Cell Physiol., 72, 141–148.
2. Anderson, D. M., Lyman, S. D., Baird, A., Wignall, J. M., Eisenman, J., Rauch, C., March, C. J., Boswell, H. S., Gimpel, S. D., Cosman, D. and Williams, D. E. (1990) Cell 63, 235–243.
3. Andre, C., D'Auriol, L., Lacombe, C., Gisselbrecht, S. and Galibert, F. (1989) Oncogene 4, 1047–1049.
4. Bazan, F. (1991) Cell 65, 9–10.
5. Bennett, D. (1956) J. Morphol. 98, 199–234.
6. Bernstein, S. E. (1960) 23, 33–34.
7. Besmer, P., Murphy, P. C., George, P. C., Qiu, F., Bergold, P. J., Lederman, L., Snyder, H. W., Brodeur, D., Zuckerman, E. E. and Hardy, W. D. (1986) Nature 320, 415–421.
8. Bradley, R. S. and Brown, A. M. C. (1990) EMBO J. 9, 1569–1575.
9. Chabot, B., Stephenson, D. A., Chapman, V. M., Besmer P. and Bernstein, A. (1988) Nature 335, 88–89.
10. Chirgwin, J. M., Przbyla, A. E., MacDonald, J. R. and Rutter, W. J. (1979) Biochemistry 18, 5924–5299.
11. Copeland, N. G., Gilbert, D. J., Cho, B. C., Donovan, P. J., Jenkins, N. A., Cosman, D., Anderson, D., Lyman, S. D. and williams, D. E. (1990) Cell 63, 175–183.
12. Dexter, T. M. and Moore, M. A. S. (1977) Nature 269, 412–414.
13. Downing, J. R., Roussel, M. F. and Sherr, C. J. (1989) Mol. Cell. Biol. 9, 2890.
14. Flanagan, J. G. and Leder, P. (1990). Cell 63, 185–194.
15. Flanagan, J. G., Chan, D. and Leder, P. (1991) Cell 64, 1125–1135.
16. Fujita, J., Onoue, H., Ebi, Y., Nakayama, H., Kanakura, Y. and Kitamura, Y. (1989) Proc. Natl. Acad. Sci. U.S.A. 86, 2888–2891.
17. Geissler, E. N., Ryan, M. A. and Housman, D. E. (1988) Cell 55, 185–192.
18. Gluzman, Y. (1981) Cell 23, 175–182.
19. Gordon, M. Y. (1991) Cancer Cells 3, 127–133.
20. Kriegler, M. (1990) Gene transfer and expression: A laboratory manual. (New York; Stockton Press)
21. Ladner, M. B., Martin, G. A., Noble, J. A., Nikoloff, D. M., Tal, R., Kawasaki, E. S. and White, T. J. (1987) EMBO J. 6, 2693–2698.
22. Lee D. C., Rose, T. M., Webb, N. R. and Todaro, G. J. (1985) Nature 313, 489–491.
23. Majumder, S., Brown, K., Qiu, F.-H. and Besmer, P. (1988) Mol. Cell. Biol. 8, 4896–4903.
24. Manova, K., Nocka, K., Besmer P. and Bachvarova, R. F. (1990) Development 110, 1057–1069.
25. Manova, K., Bachvarova, R. F. (1991) Devel. Biol. in press.
26. Massague, J. (1991) J. Biol. Chem. 265, 21393–21396.
27. Martin, F. H., Suggs. S. V. Langley, K. E., Lu, H. S., Ting, J., Okino, K. H., Morris, C. F., McNiece, I. K., Jacobsen, F. W., Mendiaz, E. A., Birkett, N. C., SMith, K. A., Johnson, M. J., Parker, V. P., Flores, J. C., Patel, A. C., Fisher, E. F., Erjavec, H. O., Herrera, C. J., Wypych, J., Sachdev, R. K., Pope, J. A., Leslie, I., Wen, D., Lin, C. H., Cuplles, R. L. and Zsebo, K. M. (1990) Cell 63, 203–211.
28. Mayer, T. C. and Green, M. C. (1968) Dev. Biol. 18, 62–75.
29. McCoshen, J. A. and McCallion, D. J. (1975) Experientia 31, 589–590.
30. McCulloch, E. A., Siminovitch, L., Till, J. E., Russel, E. S., and Bernstein, S. E. (1965) Blood 26, 399–410.
31. McCulloch, E. A. (1970) In Regulation of hematopoiesis, A. S. Gordon, ed. (New York: Appleton), pp. 649–675.
32. Mintz, B. and Russell, E. S. (1957) J. Exp. Zool. 134, 207–237.
33. Morrison-Graham, K. and Weston, J. A. (1989) Trends Genet. 5, 116–121.
34. Naughton, M. A. and Sanger, F. (1961) Biochem. J. 78, 156–162.
35. Nocka, K., Majumder, S., Chabot, B., Ray, P., Cervone, M., Bernstein, A. and Besmer, P. (1989) Genes & Dev. 3, 816–826.
36. Nocka, K., Tan, J., Chiu, E., Chu, T. Y., Ray P., Traktman, P. and Besmer, P. (1990a) EMBO J. 9, 1805–1813.
37. Nocka, K., Buck, J., Levi, E. and Besmer, P. (1990b) EMBO J. 9, 3287–3294.
38. Nocka, K., Huang, E., Beier, D. R., Chu, T. Y., Buck, J., Lahm, H. W., Wellner, D., Leder, P. and Besmer, P. (1990). Cell63, 225–233.
39. Orr-Urtreger, A., Avivi, A., Zimmer, Y., Givol, D., Yarden Y. and Lonai, P. (1990) Development 109, 911–923.
40. Pandialla, A. and Massague, J. (1991) Proc. Natl. Acad. Sci. USA 88, 1726–1730.
41. Qiu, F., Ray, P., Brown, K., Barker, P. E., Jhanwar, S., Ruddle, R. H. and Besmer, P. (1988) EMBO J. 7, 1003–1011.
42. Rathjen, P. D., Toth, S., Willis, A., Heath, J. K. and Smith, A. G. (1990) Cell 62, 1005–1114.
43. Rettenmier, C. W. (1989) Curr. Top. Micro. Immun. 149, 129–141.
44. Rettenmier, C. W. and Roussel, M. F. (1988) Mol. Cell. Biol. 8, 5026–5034.
45. Rettenmier, C. W. Roussel, M. F. Ashmun, R. A., Ralph, P., Price, K. and Sherr, C. J. (1987) Mol. Cell. Biol. 7, 2378–2387.
46. Russel, E. S. (1970) Abnormalities of erythropoiesis associated with mutant genes in mice. In Regulation of hematopoiesis, A. S. Gordon, ed. (New York: Appleton), pp. 649–675.
47. Russel, E. S. (1979) Adv. Gen 20, 357–459.
48. Sambrook, J., Fritsch, E. F. and Maniatis, T. (1989) Molecular Cloning, 2nd ed. Cold Spring Harbor Laboratory Press, Cold Spring Harbor, N.Y.
49. Sanger, F., Nicklen, S. and Coulson, A. R. (1977) Proc. Natl. Acad. Sci. USA 74, 5463–5467.
50. Sarvella, P. A. and Russel, L. B. (1956) Hered. 47, 123–128.
51. Silver, W. K. (1979) White-spotting, patch and rump-white. In the Coat Colors of Mice: A model for Gene Action and Interaction (New York: Springer-Verlag), pp. 206–241.
52. Stevens, L. C. (1979) Inbred Strains of mice. 11, 39.
53. Tan, J. C. Nocka, K., Ray, P., Traktman, P. and Besmer, P. (1990) Science 247, 209–212.
54. Todaro, G. J. and Green, H. (1963) J. Cell Biol. 17, 299–313.
55. Tushiniski, R. J., Oliver, I. T., Guilbert, L. J., Tynan, P. W., Warner, J. R. and Stanley, E. R. (1982) Cell 28, 71–81.
56. Williams, D. E., Eisenman, J., Baird, A., Rauch, C., Ness, K. V., March, C. J., Park, L. S., Martin, U., Mochizuki, D. Y., Bosell, H. S., Burgess, G. S., Cosman, D. and Stewart, D. L. (1990) Cell 63, 167–174.

57. Yarden, Y., Kuang, W. J., Yang-Feng, T., Coussens, L., Munemitsu, S., Dull, T. J., Chen, E., Schlessinger, J., Francke, U. and Ullrich, A. (1987) EMBO J. 6, 3341–3351.
58. Zsebo, K. M., Wypych, J., McNece, I. K., Lu, H. S., Smith, K. A., Karkare, S. B., Sachdev, R. K., Yuschenokoff, V. N., Birkett, N.C., Williams, L. R., Satyagal, V. N., Tung, W., Bosselman, R. A., Mendiaz, E. A. and Langley, K. E. (1990a) Cell 63, 195–201.
59. Zsebo, K. M., Williams, D. A., Geissler, E. N., Broudy, V. C., Martin, F. H., Atkins, H. L., Hsu, R. Y., Birkett, N. C., Okino, K. H., Murdock, D. C., Jacobsen, F. W., Langley, K. E., Smith, K. A., Takeishi, T., Cattanach, B. M., Galli, S. J. and Suggs. S. V. (1990B) Cell 63, 213–214.
60. Yung, Y. P. and Moore, M. A. S. (1982) J. Immunol. 129, 1256–1261.
61. Yurt, R. W., Leid, R. W., Austen, K. F. and Silbert, J. E. (1977) J. Biol. Chem. 252, 518–521.
62. Enerback, L., (1974) Histochem. 42, 301–313.
63. Dexter, T. M. and Moore, M. A. S. (1977). Nature 269, 412–414.
64. Little, C. C. and Cloudman, A. M. (1937) Proc. Natl. Acad. Sci. USA 23, 535–537.
65. Geissler, E. N., McFarland, E. C. and Russell, E. S. (1981) Genetics 97, 337–361.
66. Stevens, R. L., Lee, T. D., Seldin, D. C., Austen, K. F., Befus, A. D. and Bienenstock, J. (1986) J. Immunol. 147, 291–295.
67. Levi-Schaffer, F., Austen, K. F., Caulfield, J. P., Hein, A. Bloes, W. F. and Stevens, R. L. (1985) J. Immunol. 135, 3454–3462.
68. Gregory, C. J. and Eaves, A. C. (1978) Blood 51, 527–537.
69. Iscove, N. N. (1978b). In Aplastic Anemia, S. Hibino, S. Takaku and N. T. Shahidi, eds. (Tokyo: University of Tokyo Press), pp. 31–36.
70. Das, S. K. and Stanley, E. R. (198) J. Biol. Chem. 257, 13679.
71. Gough, N. M. and Williams, L. R. (1989) Cancer Cells 1, 77–80.
72. Kitamura, Y., Go, S., and Hatnaka, K. (1978).
73. Kitamura, Y., and Fujita, J. (1989). Blood 53, 492–497.
74. Nakahata, T., Koboyashi, T., Ishiguro, A., Tsuji, K., Jaganuma, K., Ando, O., Yagi, Y., Tadokoro, K. and Akabane, T. (1986) Nature 324, 65–67.
75. Tsuji, K., Natahata, T., Takagi, M., Kobayashi, T., Ishiguro, A., Kikuchi, T., Naganuma, K., Koiki, K., Miyajima, A., Arai. K., Akabane, T. (1990a) J. Immunol. 144, 678–684.
76. Tsui, K., Nakahata, T., Takagi, M., Kobayashi, T., Ishiguro, A., Kikuchi, T., Naganuma, K., Koike, K., Miyajima, A., Arai, K., Akabene, T., (1990b) Blood 75, 421–427.
77. Takagi M., Nakahata, T., Koike, K., Koboyashi, T., Tsuji, K., Kojima, S., Hirano, T., Miyajima, A., Arai. K. and Akabene, T. (1989) J. Exp Med 170, 233–244.
78. Iscove, N. N. (1978a). In Hematopoietic cell differentiation, D. W. Golde, M. J. Cline, D. Metcalf and F. C. Fox, edgs. (New York: Academic Press), pp. 37–52.
79. Hamaguchi, Y., Kanakura, Y., Fujita, J., Takeda, S., Nakano, T., Tarui, S., Honjo, T., Kitamura, Y. (1987) J. Exp. Med. 165, 268.
80. Russell, E. S. (1970) In Regulation of hematopoiesis, A. S. Gordon, Ed. (New York: Appleton), pp. 649–675.
81. McCulloch, E. A., Siminovitch, L., Till, J. E., Russell, E. S., and Bernstein, S. E. (1985). Blood 26, 399–410.
82. Harrison, D. E. (1980) Blood 55, 77–81.
83. Barker, J. E., and McFarland, E. C. (1988). J. Cell, Physiol. 135, 533–538.
84. Jarobe, D. L., Marshall, J. S., Randolph, T. R., Kukolja, A. and Huff, T. F. (1989) J. Immunol. 142, 2405–2417.
85. Schmidt, E. V., Paterngale, P. K., Weir, L. and Leder, P. (1988). Proc. Natl, Acad. Sci. USA 85, 6047–6051.
86. Lehrach, H., Diamond, D., Wozney, J. M., and Boedite, H. (1977). RNA molecular weight determinations by gel electrophoresis under denaturing conditions-a critical reexamination. Biochemistry 16, 4743.
87. Feinberg, A. P., and Vogeistein, B. (1963). Anal. Biochem. 132, 6–13.
88. Stanley, E. R., and Guilbert, L. J. (1961). J. Immunol. Meth. 42, 263–264.
89. Scherr, C. J., Rettenmier, C. W., Sacca, R., Roussel, M. F., Look, A. T. and Stanley, E. R. (1965). Cell 41, 666–676.
90. Chui, D. K., Liato, S. K., and Walker, K. (1978). Blood 51, 539–547.
91. Avner, P., Amar. L., Dandolo, L., and Guenet, J. L. (1968). Trends Gene, 4, 18–23.
92. Yung, et al. (1981) J. Immunol. 127, 794–799.
93. Stevens, R. L. and Austen, K. F. (1989), Immunol. Today 10, 381–386.
94. Schrader, J. W. (1981) J. Immunol. 126, 452–460.
95. Smith, C. A. and Rennick, D. M. (1986) P.N.A.S. U.S.A. 83, 1857–1861.
96. Brown, M. A. et al. (1987) Cell 50, 809–818.
97. Plaut, M. et al. (1989) Nature 339, 64–67.
98. Levi-Schaffer, F. et al. (1986) P.N.A.S. U.S.A. 83, 6485–6488.
99. Fujita, J. et al. (1988) J. Cell. Physiol. 134, 78–84.
100. Tan, J. C. et al. (1990) Science 247, 209–212.
101. Reith et al. (1990) Genes Dev. 4, 390–400.
102. Schwartz, L. B. & Huff, T. F. "Mast Cells" in The Lung (ed. Crystal, R. G. et al.) 1991 p. 601–616.
103. Moore, M. A. S. (1991) Blood 78, 1–19 and reference therein.
104. Muench, M. O. et al. (1992) Exp. Hematology, 20:339–349
105. Lerner C and Harrison DE (1990) 5-Fluorouracil spares hematopoietic stem cells responsible for long-term repopulation. Exp. Hematol 18:114

What is claimed is:

1. A composition which comprises c-kit ligand, TNF-α, and a hematopoeitic factor, the amount of each in the composition being such that the composition is effective to expand and differentiate progenitor cells into dendritic cells.

2. The composition of claim 1, wherein the hematopoeitic factor is G-CSF.

3. The composition of claim 1, wherein the hematopoeitic factor is M-CSF.

4. The composition of claim 1, wherein the hematopoeitic factor is IL-3.

5. The composition of claim 1, wherein the hematopoeitic factor is PIXY.

6. The composition of claim 1, wherein the hematopoeitic factor is IL-1.

7. A method of expanding and differentiating progenitor cells into dendritic cells ex vivo comprising treating progenitor cells with a composition which comprises c-kit ligand, TNF-α, and a hematopoeitic factor, the amount of each in the composition being such that the composition is effective to expand and differentiate progenitor cells into dendritic cells.

8. The method of claim 7, wherein the hematopoeitic factor is G-CSF.

9. The method of claim 7, wherein the hematopoeitic factor is M-CSF.

10. The method of claim 7, wherein the hematopoeitic factor is IL-3.

11. The method of claim 7, wherein the hematopoeitic factor is PIXY.

12. The method of claim 7, wherein the hematopoeitic factor is IL-1.

13. A method of expanding peripheral blood cells ex vivo comprising treating peripheral blood cells with a composition which comprises c-kit ligand, TNF-α, and a hematopoeitic factor, the amount of each in the composition being such that the composition is effective to expand peripheral blood cells.

14. The method of claim 13, wherein the hematopoeitic factor is GM-CSF.

15. The method of claim 13, wherein the hematopoeitic factor is G-CSF.

16. The method of claim 13, wherein the hematopoeitic factor is M-CSF.

17. The method of claim 13, wherein the hematopoeitic factor is IL-3.

18. The method of claim 13, wherein the hematopoeitic factor is PIXY.

19. The method of claim 13, wherein the hematopoeitic factor is IL-1.

* * * * *

UNITED STATES PATENT AND TRADEMARK OFFICE
CERTIFICATE OF CORRECTION

| | | |
|---|---|---|
| PATENT NO. | : 6,159,461 | Page 1 of 1 |
| APPLICATION NO. | : 08/898982 | |
| DATED | : December 12, 2000 | |
| INVENTOR(S) | : Peter Besmer et al. | |

It is certified that error appears in the above-identified patent and that said Letters Patent is hereby corrected as shown below:

In the specification at column 1, line 15: should read;

The invention described herein was made in the course of work under Grant Nos. RO1-CA-32926, RO1-CA-32929 and ACS MV246D from the National Institute of Health and American Cancer Society, respectively. The United States Government has certain rights in this invention.

Signed and Sealed this

Seventh Day of October, 2008

JON W. DUDAS
*Director of the United States Patent and Trademark Office*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:1:

```
CCCATATAAA TATAACCCCA TATAGTTATA G                               31
```

(2) INFORMATION FOR SEQ ID NO:2:

(i) SEQUENCE CHARACTERISTICS:
        (A) LENGTH: 63 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:2:

```
CCCATATAAC CCCCCCATAT AATAATTACA CCAATGCCCA AGCTTCGGTG CCTTTCCTTA    60

TGT                                                                 63
```

(2) INFORMATION FOR SEQ ID NO:3:

(i) SEQUENCE CHARACTERISTICS:
        (A) LENGTH: 72 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:3:

```
CCCATATAAC CCCCCCATAT AATAATTACA CCAATAGTAT CTCTAGAATT TTACACCTCT    60

TGAAATTCTC TT                                                       72
```

(2) INFORMATION FOR SEQ ID NO:4:

(i) SEQUENCE CHARACTERISTICS:
        (A) LENGTH: 69 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:4:

```
CCCATATAAC CCCCCCATAT AATAATTACA CCAATCATTT ATCTAGAAAA CATGAACTGT    60

TACCAGCCT                                                           69
```

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:5:

```
CCCATATAAC CCCCCCATAT AATAATTACA CCAATACCCT CGAGGCTGAA ATCTACTTGT          60
```

(2) INFORMATION FOR SEQ ID NO:6:

(i) SEQUENCE CHARACTERISTICS:
        (A) LENGTH: 116 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:6:

```
CCCATATAAA TATAACCCCA TATAAAGCTT GATAATGTAA AAGACATTAC AAAACTGGTG          60

GCAAATCTTC CAAATGACTA TATGATAACC TCAATTACGT GGCCGGAATG GGATCC            116
```

(2) INFORMATION FOR SEQ ID NO:7:

(i) SEQUENCE CHARACTERISTICS:
        (A) LENGTH: 54 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:7:

```
CCCATATAAA TATAACCCCA TATCGCCAA GCTTGATAAT GTAAAGATA TTAC                 54
```

(2) INFORMATION FOR SEQ ID NO:8:

(i) SEQUENCE CHARACTERISTICS:
        (A) LENGTH: 52 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:8:

```
CCCATATAAA TATAACCCCA TATATTAATA CAGCGGCCGT ACCCTAGGGG CC                 52
```

(2) INFORMATION FOR SEQ ID NO:9:

(i) SEQUENCE CHARACTERISTICS:
        (A) LENGTH: 849 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:9:

```
CCCATATAAA TATAACCCCA TATAGCGGTG CCTTTCCTTA TGAAGAAGAC ACAAACTTGG          60

ATTATCACTT GCATTTATCT TCAACTGCTC CTATTTAATC CTCTCGTCAA AACCAAGGAG        120

ATCTGCGGGA ATCCTGTGAC TGATAATGTA AAAGACATTA CAAAACTGGT GGCAAATCTT        180

CCAAATGACT ATATGATAAC CCTCAACTAT GTCGCCGGGA TGGATGTTTT GCCTAGTCAT        240

TGTTGGCTAC GACATATGGT AATACAATTA TCACTCAGCT TGACTACTCT TCTGGACAAG        300

TTCTCAAATA TTTCTGAAGG CTTGAGTAAT TACTCCATCA TAGACAAACT TGGGAAAATA        360

GTGGATGACC TCGTGTTATG CATGGAAGAA ACGCACCGA AGAATATAAA AGAATCTCCG         420

AAGAGGCCAG AAACTAGATC CTTTACTCCT GAAGAATTCT TTAGTATTTT CAATAGATCC        480

ATTGATGCCT TTAAGGACTT TATGGTGGCA TCTGACACTA GTGACTGTGT GCTGTCTTCA        540
```

```
ACATTAGGTC CCGAGAAAGA TTCCAGAGTC AGTGTCACAA AACCATTTAT GTTACCCCCT      600

GTTGCAGCCA GCTCCCTTAG GAATGACAGC AGTAGCAGTG ATAGGAAAGC CGCAAAGTCC      660

CCTGAAGACT CGGGCCTACA ATGGACAGCC ATGGCATTGC CGGCTCTCAT TTCGCTTGTA      720

ATTGGCTTTG CTTTTGGAGC CTTATACTGG AAGAAGAAAC AGTCAAGTCT ACAAGGGCA       780

GTTGAAAATA TACAGATTAA TGAAGAGGAT AATGAGATAA GTATGCTGCA ACAGAAAGAG      840

AGAGAATTT                                                              849
```

(2) INFORMATION FOR SEQ ID NO:10:

(i) SEQUENCE CHARACTERISTICS:
        (A) LENGTH: 1344 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 106..925
        (D) OTHER INFORMATION:

(xi) SEQUENCE DESCRIPTION: SEQ ID NO:10:

```
GGGACTATCT GCAGCCGCTG CTGGTGCAAT ATGCTGGAGC TCCAGAACAG CTAAACGGAG       60

TCGCCACACC GCTGCCTGGG CTGGATCGCA GCGCTGCCTT TCCTT ATG AAG AAG         114
                                                Met Lys Lys
                                                  1

ACA CAA ACT TGG ATT ATC ACT TGC ATT TAT CTT CAA CTG CTC CTA TTT       162
Thr Gln Thr Trp Ile Ile Thr Cys Ile Tyr Leu Gln Leu Leu Leu Phe
      5                  10                  15

AAT CCT CTT GTC AAA ACC AAG GAG ATC TGC GGG AAT CCT GTG ACT GAT       210
Asn Pro Leu Val Lys Thr Lys Glu Ile Cys Gly Asn Pro Val Thr Asp
 20                  25                  30                  35

AAT GTA AAA GAC ATT ACA AAA CTG GTG GCA AAT CTT CCA AAT GAC TAT       258
Asn Val Lys Asp Ile Thr Lys Leu Val Ala Asn Leu Pro Asn Asp Tyr
                 40                  45                  50

ATG ATA ACC CTC AAC TAT GTC GCC GGG ATG GAT GTT TTG CCT AGT CAT       306
Met Ile Thr Leu Asn Tyr Val Ala Gly Met Asp Val Leu Pro Ser His
             55                  60                  65

TGT TGG CTA CGA GAT ATG GTA ATA CAA TTA TCA CTC AGC TTG ACT ACT       354
Cys Trp Leu Arg Asp Met Val Ile Gln Leu Ser Leu Ser Leu Thr Thr
         70                  75                  80

CTT CTG GAC AAG TTC TCA AAT ATT TCT GAA GGC TTG AGT AAT TAC TCC       402
Leu Leu Asp Lys Phe Ser Asn Ile Ser Glu Gly Leu Ser Asn Tyr Ser
     85                  90                  95

ATC ATA GAC AAA CTT GGG AAA ATA GTG GAT GAC CTC GTG TTA TGC ATG       450
Ile Ile Asp Lys Leu Gly Lys Ile Val Asp Asp Leu Val Leu Cys Met
100                 105                 110                 115

GAA GAA AAC GCA CCG AAG AAT ATA AAA GAA TCT CCG AAG AGG CCA GAA       498
Glu Glu Asn Ala Pro Lys Asn Ile Lys Glu Ser Pro Lys Arg Pro Glu
                120                 125                 130

ACT AGA TCC TTT ACT CCT GAA GAA TTC TTT AGT ATT TTC AAT AGA TCC       546
Thr Arg Ser Phe Thr Pro Glu Glu Phe Phe Ser Ile Phe Asn Arg Ser
            135                 140                 145

ATT GAT GCC TTT AAG GAC TTT ATG GTG GCA TCT GAC ACT AGT GAC TGT       594
Ile Asp Ala Phe Lys Asp Phe Met Val Ala Ser Asp Thr Ser Asp Cys
        150                 155                 160

GTG CTC TCT TCA ACA TTA GGT CCC GAG AAA GAT TCC AGA GTC AGT GTC       642
Val Leu Ser Ser Thr Leu Gly Pro Glu Lys Asp Ser Arg Val Ser Val
```

```
                     165                 170                 175
ACA AAA CCA TTT ATG TTA CCC CCT GTT GCA GCC AGC TCC CTT AGG AAT            690
Thr Lys Pro Phe Met Leu Pro Pro Val Ala Ala Ser Ser Leu Arg Asn
180                 185                 190                 195

GAC AGC AGT AGC AGT AAT AGG AAA GCC GCA AAG GCC CCT GAA GAC TCG            738
Asp Ser Ser Ser Ser Asn Arg Lys Ala Ala Lys Ala Pro Glu Asp Ser
                200                 205                 210

GGC CTA CAA TTG ACA GCC ATG GCA TTG CCG GCT CTC ATT TCG CTT GTA            786
Gly Leu Gln Leu Thr Ala Met Ala Leu Pro Ala Leu Ile Ser Leu Val
            215                 220                 225

ATT GGC TTT GCT TTT GGA GCC TTA TAC TGG AAG AAG AAA CAG TCA AGT            834
Ile Gly Phe Ala Phe Gly Ala Leu Tyr Trp Lys Lys Lys Gln Ser Ser
        230                 235                 240

CTT ACA AGG GCA GTT GAA AAT ATA CAG ATT AAT GAA GAG GAT AAT GAG            882
Leu Thr Arg Ala Val Glu Asn Ile Gln Ile Asn Glu Glu Asp Asn Glu
    245                 250                 255

ATA AGT ATG TTG CAA CAG AAA GAG AGA GAA TTT CAA GAG GTG T                  925
Ile Ser Met Leu Gln Gln Lys Glu Arg Glu Phe Gln Glu Val
260                 265                 270

AATTGTGGAC GTATCAACAT TGTTACCTTC GCACAGTGGC TGGTAACAGT TCATGTTTGC         985

TTCATAAATG AAGCAGCCTT AAACAAATTC CCATTCTGTC TCAAGTGACA GACCTCATCC        1045

TTACCTGTTC TTGCTACCCG TGACCTTGTG TGGATGATTC AGTTGTTGGA GCAGAGTGCT        1105

TCGCTGTGAA CCCTGCACTG AATTATCATC TGTAAAGAAA AATCTGCACG GAGCAGGACT        1165

CTGGAGGTTT TGCAAGTGAT GATAGGGACA AGAACATGTG TCCAGTCTAC TTGCACCGTT        1225

TGCATGGCTT GGGAAACGTC TGAGTGCTGA AAACCCACCC AGCTTTGTTC TTCAGTCACA        1285

ACCTGCAGCC TGTCGTTAAT TATGGTCTCT GCAAGTAGAT TTCAGCCTGG ATGGTGGGG         1344

(2) INFORMATION FOR SEQ ID NO:11:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:11:

Met Lys Lys Thr Gln Thr Trp Ile Ile Thr Cys Ile Tyr Leu Gln Leu
1               5                   10                  15

Leu Leu Phe Asn Pro Leu Val Lys Thr Lys Glu Ile Cys Gly Asn Pro
                20                  25                  30

Val Thr Asp Asn Val Lys Asp Ile Thr Lys Leu Val Ala Asn Leu Pro
            35                  40                  45

Asn Asp Tyr Met Ile Thr Leu Asn Tyr Val Ala Gly Met Asp Val Leu
        50                  55                  60

Pro Ser His Cys Trp Leu Arg Asp Met Val Ile Gln Leu Ser Leu Ser
65                  70                  75                  80

Leu Thr Thr Leu Leu Asp Lys Phe Ser Asn Ile Ser Glu Gly Leu Ser
                85                  90                  95

Asn Tyr Ser Ile Ile Asp Lys Leu Gly Lys Ile Val Asp Asp Leu Val
            100                 105                 110

Leu Cys Met Glu Glu Asn Ala Pro Lys Asn Ile Lys Glu Ser Pro Lys
        115                 120                 125

Arg Pro Glu Thr Arg Ser Phe Thr Pro Glu Glu Phe Phe Ser Ile Phe
    130                 135                 140
```

```
Asn Arg Ser Ile Asp Ala Phe Lys Asp Phe Met Val Ala Ser Asp Thr
145                 150                 155                 160

Ser Asp Cys Val Leu Ser Ser Thr Leu Gly Pro Glu Lys Asp Ser Arg
            165                 170                 175

Val Ser Val Thr Lys Pro Phe Met Leu Pro Pro Val Ala Ala Ser Ser
            180                 185                 190

Leu Arg Asn Asp Ser Ser Ser Asn Arg Lys Ala Ala Lys Ala Pro
        195                 200                 205

Glu Asp Ser Gly Leu Gln Leu Thr Ala Met Ala Leu Pro Ala Leu Ile
        210                 215                 220

Ser Leu Val Ile Gly Phe Ala Phe Gly Ala Leu Tyr Trp Lys Lys
225                 230                 235                 240

Gln Ser Ser Leu Thr Arg Ala Val Glu Asn Ile Gln Ile Asn Glu Glu
            245                 250                 255

Asp Asn Glu Ile Ser Met Leu Gln Gln Lys Glu Arg Glu Phe Gln Glu
            260                 265                 270

Val
```

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:12:

GCCCAAGCTT CGGTGCCTTT CCTTATG                                      27

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:13:

AGTATCTCTA GAATTTTACA CCTCTTGAAA TTCTCT                          36

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:14:

CATTTATCTA GAAAACATGA ACTGTTACCA GCC                                33

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:15:

ACCCTCGAGG CTGAAATCTA CTTG                                                      24